(12) United States Patent
Belmares et al.

(10) Patent No.: US 7,919,584 B1
(45) Date of Patent: Apr. 5, 2011

(54) METHODS AND COMPOSITIONS FOR DIAGNOSIS AND TREATMENT OF ASTHMA

(75) Inventors: Michael P. Belmares, San Jose, CA (US); Dave Garman, San Jose, CA (US)

(73) Assignee: Arbor Vita Corporation, Sunnyvale, CA (US)

( * ) Notice: Subject to any disclaimer, the term of this patent is extended or adjusted under 35 U.S.C. 154(b) by 564 days.

(21) Appl. No.: 11/404,458

(22) Filed: Apr. 14, 2006

Related U.S. Application Data

(60) Provisional application No. 60/671,940, filed on Apr. 15, 2005.

(51) Int. Cl.
*C07K 14/00* (2006.01)

(52) U.S. Cl. ........................ 530/350; 530/300

(58) Field of Classification Search ................. None
See application file for complete search history.

(56) References Cited

OTHER PUBLICATIONS

Nakanishi et al. (2001) PNAS 98: 5175-5180.*
Gruber et al. American J. Physiol 276: (cell physiol. 45:C1261-C1270).*

\* cited by examiner

*Primary Examiner* — Michael Pak

(57) ABSTRACT

This invention relates to methods of reducing inflammatory effects in mammalian cells by treatment with compounds that interfere with calcium activated chloride channel function. The invention discloses methods of treating these disorders by administering inhibitors that disrupt protein-protein interactions involved in these disorders, screening methods to identify such inhibitors and specific compositions useful for treating these disorders.

9 Claims, No Drawings

SEQUENCE LISTING

```
<160> NUMBER OF SEQ ID NOS: 40

<210> SEQ ID NO 1
<211> LENGTH: 118
<212> TYPE: PRT
<213> ORGANISM: Homo sapiens

<400> SEQUENCE: 1

His Leu Arg Leu Leu Asn Ile Ala Cys Ala Ala Lys Ala Lys Arg Arg
1               5                   10                  15

Leu Met Thr Leu Thr Lys Pro Ser Arg Glu Ala Pro Leu Pro Phe Ile
            20                  25                  30

Leu Leu Gly Gly Ser Glu Lys Gly Phe Gly Ile Phe Val Asp Ser Val
        35                  40                  45

Asp Ser Gly Ser Lys Ala Thr Glu Ala Gly Leu Lys Arg Gly Asp Gln
    50                  55                  60

Ile Leu Glu Val Asn Gly Gln Asn Phe Glu Asn Ile Gln Leu Ser Lys
65                  70                  75                  80

Ala Met Glu Ile Leu Arg Asn Asn Thr His Leu Ser Ile Thr Val Lys
                85                  90                  95

Thr Asn Leu Phe Val Phe Lys Glu Leu Leu Thr Arg Leu Ser Glu Glu
            100                 105                 110

Lys Arg Asn Gly Ala Pro
        115

<210> SEQ ID NO 2
<211> LENGTH: 110
<212> TYPE: PRT
<213> ORGANISM: Homo sapiens

<400> SEQUENCE: 2

Met Gly Leu Gly Val Ser Ala Glu Gln Pro Ala Gly Gly Ala Glu Gly
1               5                   10                  15

Phe His Leu His Gly Val Gln Gly Asn Ser Pro Ala Gln Gln Ala Gly
            20                  25                  30

Leu Glu Pro Tyr Phe Asp Phe Ile Ile Thr Ile Gly His Ser Arg Leu
        35                  40                  45

Asn Lys Glu Asn Asp Thr Leu Lys Ala Leu Leu Lys Ala Asn Val Glu
    50                  55                  60

Lys Pro Val Lys Leu Glu Val Phe Asn Met Lys Thr Met Arg Val Arg
65                  70                  75                  80

Glu Val Glu Val Val Pro Ser Asn Met Trp Gly Gly Gln Gly Leu Leu
                85                  90                  95

Gly Ala Ser Val Arg Phe Cys Ser Phe Arg Arg Ala Ser Glu
            100                 105                 110

<210> SEQ ID NO 3
<211> LENGTH: 110
<212> TYPE: PRT
<213> ORGANISM: Homo sapiens
```

-continued

```
<400> SEQUENCE: 3

Leu Asn Val Tyr Val Asn Pro Lys Lys Leu Thr Val Ile Lys Ala Lys
1               5                   10                  15

Glu Gln Leu Lys Leu Leu Glu Val Leu Val Gly Ile Ile His Gln Thr
            20                  25                  30

Lys Trp Ser Trp Arg Arg Thr Gly Lys Gln Gly Asp Gly Glu Arg Leu
        35                  40                  45

Val Val His Gly Leu Leu Pro Gly Gly Ser Ala Met Lys Ser Gly Gln
    50                  55                  60

Val Leu Ile Gly Asp Val Leu Val Ala Val Asn Asp Val Asp Val Thr
65                  70                  75                  80

Thr Glu Asn Ile Glu Arg Val Leu Ser Cys Ile Pro Gly Pro Met Gln
                85                  90                  95

Val Lys Leu Thr Phe Glu Asn Ala Tyr Asp Val Lys Arg Glu
            100                 105                 110

<210> SEQ ID NO 4
<211> LENGTH: 5
<212> TYPE: PRT
<213> ORGANISM: Artificial
<220> FEATURE:
<223> OTHER INFORMATION: GST-PDZ linker for fusion protein

<400> SEQUENCE: 4

Gly Ile Pro Gly Asn
1               5

<210> SEQ ID NO 5
<211> LENGTH: 5
<212> TYPE: PRT
<213> ORGANISM: Artificial
<220> FEATURE:
<223> OTHER INFORMATION: polyglycine linker

<400> SEQUENCE: 5

Gly Gly Gly Gly Ser
1               5

<210> SEQ ID NO 6
<211> LENGTH: 14
<212> TYPE: PRT
<213> ORGANISM: Artificial
<220> FEATURE:
<223> OTHER INFORMATION: Beta sheet facilitating polylinker

<400> SEQUENCE: 6

Glu Gly Lys Ser Ser Gly Ser Gly Ser Glu Ser Lys Val Asp
1               5                   10

<210> SEQ ID NO 7
<211> LENGTH: 18
<212> TYPE: PRT
<213> ORGANISM: Artificial
<220> FEATURE:
<223> OTHER INFORMATION: Beta sheet facilitating polylinker

<400> SEQUENCE: 7

Lys Glu Ser Gly Ser Val Ser Ser Glu Gln Leu Ala Gln Phe Arg Ser
1               5                   10                  15

Leu Asp

<210> SEQ ID NO 8
<211> LENGTH: 11
```

```
<212> TYPE: PRT
<213> ORGANISM: Artificial
<220> FEATURE:
<223> OTHER INFORMATION: Tat fragment

<400> SEQUENCE: 8

Tyr Gly Arg Lys Lys Arg Arg Gln Arg Arg
1               5                   10

<210> SEQ ID NO 9
<211> LENGTH: 20
<212> TYPE: PRT
<213> ORGANISM: Artificial
<220> FEATURE:
<223> OTHER INFORMATION: Tat fragment

<400> SEQUENCE: 9

Tyr Gly Arg Lys Lys Arg Arg Gln Arg Arg Arg Ile Gly Glu Leu Gln
1               5                   10                  15

Leu Ser Ile Ala
            20

<210> SEQ ID NO 10
<211> LENGTH: 20
<212> TYPE: PRT
<213> ORGANISM: Artificial
<220> FEATURE:
<223> OTHER INFORMATION: Tat fragment-9aa peptide

<400> SEQUENCE: 10

Tyr Gly Arg Lys Lys Arg Arg Gln Arg Arg Arg Glu Met Gln Val Thr
1               5                   10                  15

Leu Gly Leu His
            20

<210> SEQ ID NO 11
<211> LENGTH: 20
<212> TYPE: PRT
<213> ORGANISM: Artificial
<220> FEATURE:
<223> OTHER INFORMATION: PL peptide

<400> SEQUENCE: 11

Tyr Gly Arg Lys Lys Arg Arg Gln Arg Arg Arg Glu Met Gln Val Thr
1               5                   10                  15

Leu Gly Leu His
            20

<210> SEQ ID NO 12
<211> LENGTH: 20
<212> TYPE: PRT
<213> ORGANISM: Artificial
<220> FEATURE:
<223> OTHER INFORMATION: PL peptide

<400> SEQUENCE: 12

Tyr Gly Arg Lys Lys Arg Arg Gln Arg Arg Arg Gly Ala Ser Ala Asp
1               5                   10                  15

Ser Thr Gln Ala
            20

<210> SEQ ID NO 13
<211> LENGTH: 20
<212> TYPE: PRT
<213> ORGANISM: Artificial
<220> FEATURE:
```

```
<223> OTHER INFORMATION: PL peptide

<400> SEQUENCE: 13

Lys His Ser Arg Lys Ser Ser Tyr Ser Ser Ser Thr Thr Val
1               5                   10                  15

Lys Thr Ser Tyr
            20

<210> SEQ ID NO 14
<211> LENGTH: 20
<212> TYPE: PRT
<213> ORGANISM: Artificial
<220> FEATURE:
<223> OTHER INFORMATION: PL peptide

<400> SEQUENCE: 14

Tyr Gly Arg Lys Lys Arg Arg Gln Arg Arg Asn Asp Asn Ile Ala
1               5                   10                  15

Leu Leu Val Gln
            20

<210> SEQ ID NO 15
<211> LENGTH: 20
<212> TYPE: PRT
<213> ORGANISM: Artificial
<220> FEATURE:
<223> OTHER INFORMATION: PL peptide

<400> SEQUENCE: 15

Tyr Gly Arg Lys Lys Arg Arg Gln Arg Arg Glu Met Gln Val Thr
1               5                   10                  15

Leu Gly Leu His
            20

<210> SEQ ID NO 16
<211> LENGTH: 20
<212> TYPE: PRT
<213> ORGANISM: Artificial
<220> FEATURE:
<223> OTHER INFORMATION: PL peptide

<400> SEQUENCE: 16

Tyr Gly Arg Lys Lys Arg Arg Gln Arg Arg Ser Glu Gly Val Pro
1               5                   10                  15

Asp Leu Leu Val
            20

<210> SEQ ID NO 17
<211> LENGTH: 20
<212> TYPE: PRT
<213> ORGANISM: Artificial
<220> FEATURE:
<223> OTHER INFORMATION: PL peptide

<400> SEQUENCE: 17

Asp Phe Arg Pro Ser Phe Lys His Ile Leu Phe Arg Arg Ala Arg Arg
1               5                   10                  15

Gly Phe Arg Gln
            20

<210> SEQ ID NO 18
<211> LENGTH: 19
<212> TYPE: PRT
<213> ORGANISM: Artificial
<220> FEATURE:
```

<223> OTHER INFORMATION: PL peptide

<400> SEQUENCE: 18

Ser Ser Lys Ser Lys Ser Ser Glu Glu Ser Gln Thr Phe Phe Gly Leu
1               5                   10                  15

Tyr Lys Leu

<210> SEQ ID NO 19
<211> LENGTH: 20
<212> TYPE: PRT
<213> ORGANISM: Artificial
<220> FEATURE:
<223> OTHER INFORMATION: PL peptide

<400> SEQUENCE: 19

Gly Arg Trp Thr Gly Arg Ala Met Ser Ala Trp Lys Pro Thr Arg Arg
1               5                   10                  15

Glu Thr Glu Val
            20

<210> SEQ ID NO 20
<211> LENGTH: 20
<212> TYPE: PRT
<213> ORGANISM: Artificial
<220> FEATURE:
<223> OTHER INFORMATION: PL peptide

<400> SEQUENCE: 20

Ile Leu Asn Ser Ile Gln Val Met Arg Ala Gln Met Asn Gln Ile Gln
1               5                   10                  15

Ser Val Glu Val
            20

<210> SEQ ID NO 21
<211> LENGTH: 20
<212> TYPE: PRT
<213> ORGANISM: Artificial
<220> FEATURE:
<223> OTHER INFORMATION: PL peptide

<400> SEQUENCE: 21

Lys His Ser Arg Lys Ser Ser Tyr Ser Ser Ser Ser Thr Thr Val
1               5                   10                  15

Lys Thr Ser Tyr
            20

<210> SEQ ID NO 22
<211> LENGTH: 20
<212> TYPE: PRT
<213> ORGANISM: Artificial
<220> FEATURE:
<223> OTHER INFORMATION: PL peptide

<400> SEQUENCE: 22

Tyr Gly Arg Lys Lys Arg Arg Gln Arg Arg Lys Leu Ser Ser Ile
1               5                   10                  15

Glu Ser Asp Val
            20

<210> SEQ ID NO 23
<211> LENGTH: 20
<212> TYPE: PRT
<213> ORGANISM: Artificial
<220> FEATURE:
<223> OTHER INFORMATION: PL peptide

<400> SEQUENCE: 23

His Asp Phe Arg Arg Ala Phe Lys Lys Ile Leu Ala Arg Gly Asp Arg
1               5                   10                  15

Lys Arg Ile Val
            20

<210> SEQ ID NO 24
<211> LENGTH: 20
<212> TYPE: PRT
<213> ORGANISM: Artificial
<220> FEATURE:
<223> OTHER INFORMATION: PL peptide

<400> SEQUENCE: 24

Pro Ile Pro Ala Gly Gly Cys Thr Phe Ser Gly Ile Phe Pro Thr Leu
1               5                   10                  15

Thr Ser Pro Leu
            20

<210> SEQ ID NO 25
<211> LENGTH: 20
<212> TYPE: PRT
<213> ORGANISM: Artificial
<220> FEATURE:
<223> OTHER INFORMATION: PL peptide

<400> SEQUENCE: 25

His His Leu Val Ala Gln Arg Asp Ile Arg Gln Phe Gln Leu Gln His
1               5                   10                  15

Trp Leu Ala Ile
            20

<210> SEQ ID NO 26
<211> LENGTH: 20
<212> TYPE: PRT
<213> ORGANISM: Artificial
<220> FEATURE:
<223> OTHER INFORMATION: PL peptide

<400> SEQUENCE: 26

Phe His Ser Lys Thr Ala Gly Ala Asn Thr Thr Asp Lys Glu Leu Glu
1               5                   10                  15

Val Leu Ser Leu
            20

<210> SEQ ID NO 27
<211> LENGTH: 20
<212> TYPE: PRT
<213> ORGANISM: Artificial
<220> FEATURE:
<223> OTHER INFORMATION: PL peptide

<400> SEQUENCE: 27

Leu Asn Ser Cys Ser Asn Arg Arg Val Tyr Lys Lys Met Pro Ser Ile
1               5                   10                  15

Glu Ser Asp Val
            20

<210> SEQ ID NO 28
<211> LENGTH: 19
<212> TYPE: PRT
<213> ORGANISM: Artificial
<220> FEATURE:
<223> OTHER INFORMATION: PL peptide

```
<400> SEQUENCE: 28

Thr Thr Asn Asn Asn Pro Asn Ser Ala Val Asn Ile Lys Lys Ile Phe
1               5                   10                  15

Thr Asp Val

<210> SEQ ID NO 29
<211> LENGTH: 20
<212> TYPE: PRT
<213> ORGANISM: Artificial
<220> FEATURE:
<223> OTHER INFORMATION: PL peptide

<400> SEQUENCE: 29

Leu Ser Glu Lys Lys Thr Ser Gln Ser Pro His Arg Phe Gln Lys Thr
1               5                   10                  15

Ala Ser Pro Ile
            20

<210> SEQ ID NO 30
<211> LENGTH: 20
<212> TYPE: PRT
<213> ORGANISM: Artificial
<220> FEATURE:
<223> OTHER INFORMATION: PL peptide inhibitor

<400> SEQUENCE: 30

Tyr Gly Arg Lys Lys Arg Arg Gln Arg Arg Gly Ala Ser Ala Asp
1               5                   10                  15

Ser Thr Gln Ala
            20

<210> SEQ ID NO 31
<211> LENGTH: 20
<212> TYPE: PRT
<213> ORGANISM: Artificial
<220> FEATURE:
<223> OTHER INFORMATION: PL peptide inhibitor

<400> SEQUENCE: 31

Tyr Gly Arg Lys Lys Arg Arg Gln Arg Arg Ile Gly Glu Leu Gln
1               5                   10                  15

Leu Ser Ile Ala
            20

<210> SEQ ID NO 32
<211> LENGTH: 20
<212> TYPE: PRT
<213> ORGANISM: Artificial
<220> FEATURE:
<223> OTHER INFORMATION: PL peptide inhibitor

<400> SEQUENCE: 32

Tyr Gly Arg Lys Lys Arg Arg Gln Arg Arg Ile Gly Glu Leu Gln
1               5                   10                  15

Leu Ser Ile Val
            20

<210> SEQ ID NO 33
<211> LENGTH: 20
<212> TYPE: PRT
<213> ORGANISM: Artificial
<220> FEATURE:
<223> OTHER INFORMATION: PL peptide inhibitor
```

```
<400> SEQUENCE: 33

Tyr Gly Arg Lys Lys Arg Arg Gln Arg Arg Ile Gly Glu Leu Gln
1               5                   10                  15

Leu Ser Trp Ala
            20

<210> SEQ ID NO 34
<211> LENGTH: 20
<212> TYPE: PRT
<213> ORGANISM: Artificial
<220> FEATURE:
<223> OTHER INFORMATION: PL peptide inhibitor

<400> SEQUENCE: 34

Tyr Gly Arg Lys Lys Arg Arg Gln Arg Arg Glu Met Gln Val Thr
1               5                   10                  15

Leu Gly Trp His
            20

<210> SEQ ID NO 35
<211> LENGTH: 20
<212> TYPE: PRT
<213> ORGANISM: Artificial
<220> FEATURE:
<223> OTHER INFORMATION: PL peptide inhbiitor

<400> SEQUENCE: 35

Tyr Gly Arg Lys Lys Arg Arg Gln Arg Arg Glu Met Gln Val Thr
1               5                   10                  15

Leu Ser Trp His
            20

<210> SEQ ID NO 36
<211> LENGTH: 20
<212> TYPE: PRT
<213> ORGANISM: Artificial
<220> FEATURE:
<223> OTHER INFORMATION: PL peptide inhibitor

<400> SEQUENCE: 36

Tyr Gly Arg Lys Lys Arg Arg Gln Arg Arg Ile Gly Glu Leu Gln
1               5                   10                  15

Leu Ser Leu Ala
            20

<210> SEQ ID NO 37
<211> LENGTH: 20
<212> TYPE: PRT
<213> ORGANISM: Artificial
<220> FEATURE:
<223> OTHER INFORMATION: PL peptide inhibitor

<400> SEQUENCE: 37

Tyr Gly Arg Lys Lys Arg Arg Gln Arg Arg Ile Gly Glu Leu Gln
1               5                   10                  15

Leu Thr Ile Ala
            20

<210> SEQ ID NO 38
<211> LENGTH: 20
<212> TYPE: PRT
<213> ORGANISM: Artificial
<220> FEATURE:
<223> OTHER INFORMATION: PL peptide inhibitor
```

-continued

```
<400> SEQUENCE: 38

Tyr Gly Arg Lys Lys Arg Arg Gln Arg Arg Glu Met Gln Val Thr
1               5                   10                  15

Leu Thr Leu His
            20

<210> SEQ ID NO 39
<211> LENGTH: 20
<212> TYPE: PRT
<213> ORGANISM: Artificial
<220> FEATURE:
<223> OTHER INFORMATION: PL peptide inhibitor

<400> SEQUENCE: 39

Tyr Gly Arg Lys Lys Arg Arg Gln Arg Arg Ile Gly Glu Leu Gln
1               5                   10                  15

Leu Ser Ile Leu
            20

<210> SEQ ID NO 40
<211> LENGTH: 20
<212> TYPE: PRT
<213> ORGANISM: Artificial
<220> FEATURE:
<223> OTHER INFORMATION: PL peptide inhibitor

<400> SEQUENCE: 40

Tyr Gly Arg Lys Lys Arg Arg Gln Arg Arg Glu Met Gln Val Thr
1               5                   10                  15

Leu Ser Ile Ala
            20
```

METHODS AND COMPOSITIONS FOR DIAGNOSIS AND TREATMENT OF ASTHMA

CROSS-REFERENCE TO RELATED APPLICATIONS

This application claims the benefit of U.S. Provisional application 60/671,940, filed Apr. 15, 2005, herein incorporated by reference in its entirety.

FIELD OF THE INVENTION

This invention relates to methods of treating pulmonary diseases including asthma, chronic obstructive pathway disease, including emphysema and chronic bronchitis, and disorders associated with improper mucus secretion. The invention discloses methods of treating these disorders by administering inhibitors that disrupt protein-protein interactions involved in these disorders, screening methods to identify such inhibitors, and specific compositions useful for treating these disorders.

BACKGROUND OF THE INVENTION

Ion transport across the plasma membrane is critical for maintaining the normal physiology of the cell. Ion transport across the plasma membrane is mediated by a variety of membrane bound proteins which act as channels and pumps. Dysfunctional ion channels or pumps will lead to a disease state. Cystic fibrosis is a disease resulting from a defect in a cAMP-mediated chloride channel, CFTR (Welsh et al. (1993) Cell 73:1251-1254). The physiological manifestation of cystic fibrosis includes airway obstruction resulting from thick secretions of mucus into the airways of the lung and gastrointestinal tract and the subsequent colonization of the lung airways by pathogenic microorganisms (Clarke et al. (1992) Science 257:1125-1128; Clarke et al. (1994) Proc Natl Acad Sci USA 91:479-483; Eng et al. (1996) Ped Pulmonol 21:77-83) and mucus plugging of pancreatic ducts of the gastrointestinal tract (WO 01/54685).

Mucus is a thin film of protective viscoelastic liquid which lines the airways, gastrointestinal tract, and other organs containing mucus membranes. Mucus is an aqueous solution in which the major component is a glycoconjugate, known as mucin. Mucin secretion may be constitutive, regulated, or in response to external stimuli, in particular irritants.

The association of cystic fibrosis with aberrant ion transport has led investigators to hypothesize that dysfunctional ion transport might be related to other diseases with similar symptoms. Thus, dysfunctional ion transport has been implicated in diseases such as asthma and chronic obstructive pathway disease (COPD), i.e., emphysema and chronic bronchitis.

The Calcium-activated Chloride Channels (CaCC), also known as Chloride Channels, Calcium-Activated (CLCA) proteins, are emerging as a new class of channel proteins that mediate $Ca^{2+}$-activated $Cl^-$ conductance in a variety of tissues. It has been reported that the stimulation of chloride secretion results in the secretion of mucin from goblet cells in the intestinal epithelium. (Halm, et al. (1995) Am. J. Physiol. 269:929-942.) Members of the CLCA family have been cloned, isolated, and partially characterized from human, bovine, and murine species. These proteins demonstrate a high degree of homology in their size, sequence, and predicted structure yet can vary considerably in tissue distribution.

Members of this family include: bovine lung endothelial cell adhesion molecule, Lu-ECAM-1 (Elble, et al. (1997) J. Biol. Chem. 272:27853-27861); bovine $Ca^{2+}$-activated $Cl^-$, CaCC or bCLCA1 (Cunningham, et al. (1995) J. Biol. Chem. 270:31016-31026); murine CLCA1, mCLCA1 (Gandhi, et al. (1998) J. Biol. Chem. 273:32096-32101); human CLCA1, hCLCA1 (Gruber, et al. (1998) Genomics 54:200-214); murine Gob-5, mGob-5, also known as murine CLCA3, mCLCA3 (Komiya, et al. (1999) Biochem. Biophys. Res. Comm. 255:347-351, Zhou et al. (2002) Am J. Respir. Cell Mol. Biol. 25:486-491); and human CLCA2, hCLCA2 (Gruber, et al. (1999) Am. J. Physiol. 276(Cell Physiol. 45): C1261-C1270.) Recently, Holroyd, et al., PCT publication No. WO 99/44620, described a calcium activated chloride channel that is induced by IL-9.

mCLCA3 is a 913 amino acid, approximately 110 kDa, glycosylated protein which is processed to an approximately 90 kDa amino terminal cleavage product and additional smaller fragments. mCLCA3 has been shown, through in situ hybridization, to be expressed in the mucus-secreting cells of the stomach, small intestine, colon, and uterus, along with slight expression in the trachea. (Komiya, et al. supra.)

The three human CLCA homologs (hCLCA1, hCLCA2, and hCLCA3) thus far cloned, isolated, and partially characterized, all retain sequence homology, similar cDNA length, and are all located on the short arm of chromosome 1 (1p22-p31). Human CLCA proteins show a restricted pattern of expression in differing secretory tissues. Human CLCA1 was the first reported calcium activated chloride channel in humans. The 31,902-bp hCLCA1 gene is located on chromosome 1p22-p31, contains 14 introns, and is preceded by a canonic promoter region that contains an LI transposable element. Expression of hCLCA1 is predominant in intestinal basal crypt epithelia and goblet cells. Expression has been detected in small intestine, colon, appendix, and rectal mucosa. (Ritzka et al. (2004) Hum. Genet. 115:483-491)

A protein processing model has been proposed for hCLCA1 in which the primary translation product (125-kDa) is cleaved to a 90-kDa and a group of 37- to 41-kDa proteins, the latter apparently representing different glycosylation products of the same polypeptide (Gruber et al., supra). Transient expression of hCLCA1 cDNA in HEK 293 cells is associated with an increase in whole-cell $Ca^{2+}$-activated Cl conductance that is susceptible to inhibition with anion channel blocking compounds. Cell attached patch recordings of transfected cells in this study revealed single channels with a slope conductance of 13.4 pS (Gruber et al., supra). It has further been suggested that expression of hCLCA1 is associated with chloride ion flux across the plasma membrane and that non-selective chloride channel inhibitors such as niflumic acid, 4,4'-diisothiocyanatostilbene-2,2'-disulfonic acid, and dithiothreitol will abrogate this effect. (Gruber et al., supra).

hCLCA1, and its proposed murine homolog, mCLCA3, are putative calcium activated chloride channels (WO 99/44620). Both have been implicated in the pathology associated with asthma. Asthma is characterized by a hypersensitivity to environmental allergens which is associated with an inflammatory response and the increased production of mucin (WO 01/54685; WO 99/44620). Expression of hCLCA1 and mCLCA3 is up-regulated in response to allergen challenge. Expression has also been linked to mucin overproduction (Hoshino et al. (2002) Am J Respir Crit. Care Med 165:1132-1136). Over expression of hCLCA1 and mCLCA3 has been shown to induce expression of MUC5AC, a mucin gene, in a muco-epidermal cell line. Expression of hCLCA1 was shown to be upregulated in patients with bronchial asthma compared with control subjects (Hoshino et al., supra; Toda et al. (2002) J. Allergy Clin. Immunol. 109:246-250). Additionally, adenovirus mediated antisense therapy has abrogated the effects of mCLCA3 hyper-responsiveness and mucin production in an in vivo mouse model (Nakanishi et al. (2001) Proc Natl Acad Sci USA 98:5175-5180).

Hegab et al. (2004; J. Med. Genet. 41:e27) have suggested a role for hCLCA1 in chronic obstructive pulmonary disease. Both hCLCA1 and mCLCA3 are proposed to have roles in regulating antigen-stimulated epithelial cell functions in allergen-induced disease (Zhou et al., supra).

PDZ domains are regions of signaling proteins that function to modulate protein-protein interactions such as protein-protein recognition. Proteins containing PDZ domains have roles in many cell functions, including cell signaling, cell adhesion, ion transport, and formation of tight junctions. Structurally, PDZ domains are 80-90 amino acid modular domains that comprise six beta-strands (betaA to betaF) and two alpha-helices, A and B, compactly arranged in a globular structure. Peptide binding of the ligand takes place in an elongated surface groove as an anti-parallel beta-strand interacts with the betaB strand and the B helix. The structure of PDZ domains allows binding to a free carboxylate group at the end of a peptide through a carboxylate-binding loop between the betaA and betaB strands. PDZ domains bind to the last four to six carboxy-terminal amino acids in a target protein, with different classes of PDZ proteins recognizing different characteristic sequence motifs. Some PDZ domains can also recognize internal motifs present in beta-hairpin structures. (Ponting, C. P. et al. (1997) Bioessays 19:469-479; Doyle et al. (1996) Cell 85:1067-1076; Songyang, Z. et al. (1997) Science 275:73-77; Bezprozvanny, I. and Maximov, A. (2001) FEBS Lett. 509:457-462; and Jelen, F. et al. (2003) Acta Biochimica Polonica 50:985-1017).

The majority of PDZ proteins are associated with the clustering and localization of proteins at the plasma membrane. Interestingly, PDZ proteins have been shown to be involved in the control of sorting, localization, and release from the secretory pathway (Scott, D. B. et al. (2001) J. Neurosci. 21:3063-3072; Greger, I. H. (2002) Neuron 34:75-772).

Modulators of interactions between PDZ proteins and CLCA1 proteins are useful in the treatment of pulmonary diseases including asthma, chronic obstructive pathway disease, including emphysema and chronic bronchitis, and disorders associated with improper mucus secretion. PDZ proteins are useful in the detection of CLCA1 proteins and in the diagnosis of pulmonary diseases including asthma, chronic obstructive pathway disease, including emphysema and chronic bronchitis, and disorders associated with improper mucus secretion.

BRIEF SUMMARY OF THE INVENTION

The present invention relates to the treatment of pulmonary disorders such as asthma, chronic obstructive pathway disease, including emphysema and chronic bronchitis, and disorders associated with improper mucus secretion by modulating specific protein:protein interactions including, but not limited to, PDZ domain:PDZ Ligand (PL) interactions that involve, directly or indirectly, the CLCA1 calcium activated chloride channel, and are involved in mediating these clinical disorders. Methods for identifying specific therapeutics that modulate the specific protein:protein interactions involved in these disorders are also provided. Compounds and compositions for treating these pulmonary disorders are also disclosed.

The present invention relates to the discovery that human PDZ proteins bind to both human CLCA1 and the mouse homolog CLCA3. This finding was unexpected because although the human CLCA1 protein has a canonical PL motif at the C-terminus, the mouse homolog does not. The mCLCA3 protein is the first known example of a PDZ ligand protein having a histidine residue at its C-terminus, and represents a novel class of PDZ ligands. The finding that both human CLCA1 and mCLCA3 bind to a shared set of PDZ protein domains despite the lack of similarity at the C-terminal sequences of these two proteins suggests that interactions of the CLCA1 protein with PDZ domain proteins play a role in important cellular pathways that are conserved from mouse to man. Because these protein interactions are conserved, potential therapeutics directed towards disrupting these interactions can be tested in mouse models, such as the mouse model for airway hyperrsesponsiveness (Corry, D. B. et al. (1996) J. Exp. Med. 183:109-117).

The invention provides PDZ proteins that are bound by both the human CLCA1 protein and the mouse protein mCLCA3, which is the mouse homolog of human CLCA1. Methods are also provided to identify inhibitors that are high affinity for CLCA1-specific interactions as well as CLCA1-associated protein interactions. Other methods are provided to determine selectivity of inhibition, both against the different CLCA channels, CLCA1-associated proteins and the PDZs that can bind them. Methods for delivering peptide inhibitors to cells are also disclosed.

One class of pharmaceutical compositions that are provided include a pharmaceutical composition comprising an isolated, recombinant or synthetic polypeptide inhibitor that inhibits binding between a CLCA1 protein and a PDZ protein with a physiologically acceptable carrier, diluent or excipient, wherein the polypeptide comprises a C-terminal amino acid sequence of a protein selected from those listed in Table 5 or Table 6. In certain embodiments, the C-terminal amino acid sequence of the polypeptide is selected from the group consisting of SIA, SIV, SIL, SWA, SLA, GWH, SWH, TIA, and TLH. These compositions can be used to inhibit binding between a CLCA1 protein and various PDZ proteins, including, for example, but not limited to, GORASP1, KIAA0313, and KIAA1284.

The polypeptides in these compositions can be of varying lengths. In a certain embodiment such polypeptides are 3-20 amino acids in length. In other embodiments, the polypeptides are fusion polypeptides, which include the C-terminal amino acid sequence of the PL polypeptide and a segment of a transmembrane transporter sequence that is effective to facilitate transport of the polypeptide into the desired cell type, for example, a lung cell (also known as a cell-membrane transduction domain).

Another class of pharmaceutical compositions may also include an isolated, recombinant or synthetic polypeptide and a physiologically acceptable carrier, diluent or excipient, wherein the polypeptide is 3-20 amino acids in length and inhibits binding between a CLCA1 protein and a PDZ protein. The polypeptides in some of these compositions are 3-8 amino acids in length. Exemplary sequences of such polypeptides include SIA, SIV, SWA, SLA, GWH, SWH, TIA, and TLH.

Still other pharmaceutical compositions include a fusion polypeptide that inhibits binding between a CLCA1 protein and a PDZ protein and a physiologically acceptable carrier, diluent or excipient. In certain embodiments, the fusion polypeptide inhibitor in these compositions is a fusion of (i) a 9 amino acid segment that has a C-terminal sequence and (ii) an amino acid segment of a transmembrane transporter that is effective to transport the polypeptide into a lung cell or other affected cell. In other embodiments the fusion polypeptide inhibitor comprises (i) a 3-8 amino acid segment that has a C-terminal sequence and (ii) an amino acid segment of a transmembrane transporter that is effective to transport the polypeptide into a lung cell or other affected cell. In yet other embodiments the fusion polypeptide inhibitor comprises (i) a 9-20 amino acid segment that has a C-terminal sequence and (ii) an amino acid segment of a transmembrane transporter that is effective to transport the polypeptide into a lung cell or other affected cell.

The polypeptide inhibitors in the foregoing pharmaceutical compositions can be used in a variety of therapies, including treatment of a number of pulmonary disorders. Examples of such disorders include, but are not limited to, asthma, chronic obstructive pathway disease, emphysema, and chronic bronchitis, and pulmonary pathologies such as airway hyperresponsiveness, goblet cell metaplasia, and mucus overproduction. The inhibitors can also be used in the preparation of medicaments for use in the treatment of pulmonary disorders.

Also provided are methods for determining whether a test compound modulates binding between a PDZ protein and a CLCA1 protein. Certain of these methods involve contacting a PDZ-domain containing polypeptide and a PDZ-Ligand ("PL") containing peptide having at least the C-terminal 3 amino acids of the CLCA1 protein in the presence of the test compound. In certain embodiments, the PDZ proteins in these screening methods may be selected from the group consisting of GORASP1, KIAA0313, and KIAA1284. The amount of complex formed between the PDZ-domain polypeptide and the PL peptide is then determined. The test compound is identified as a potential inhibitor of binding between the PDZ protein and the CLCA1 protein if a lower amount of the complex is detected in the presence of the test compound relative to the concentration of the complex in the absence of the test compound. Another assay can be conducted using compounds identified in the initial screen to determine whether the identified compound mitigates against a condition associated with a pulmonary disorder. Such assays may be conducted, for example, using a mouse model for airway hyperresponsiveness.

BRIEF DESCRIPTION OF THE TABLES

TABLE 1 shows classifications of genetically encoded and non-encoded amino acids. Column 1 shows the classification, column 2 shows genetically encoded amino acids, and column 3 shows genetically non-encoded amino acids.

TABLE 2 shows the sequences some of PDZ domains cloned to produce GST-PDZ fusion proteins. Column 1 shows the gene name, column 2 shows alternative names by which the gene is known, column 3 shows the sequence fused to the GST construct and column 4 shows the GenBank GI or Accession number.

TABLE 3 shows PDZs demonstrated to interact with the Tat-hCLCA1 and Tat-CLCA3 peptides.

TABLE 4 shows the results of titrations of the Tat-hCLCA1 and Tat-CLCA3 peptides with selected PDZ domains.

TABLE 5 shows peptides that have been found to interact with PDZ domains that also bind to the Tat-hCLCA1 and Tat-CLCA3 peptides.

TABLE 6 shows peptides that are potential inhibitors of the interactions of CLCA1 proteins with PDZ domains.

DETAILED DESCRIPTION OF THE INVENTION

I. Definitions

"Polypeptide," "protein" and "peptide" are used interchangeably herein and include a molecular chain of amino acids linked through peptide bonds. The terms do not refer to a specific length of the product. Thus, "peptides," "oligopeptides," and "proteins" are included within the definition of polypeptide. The terms include post-translational modifications of the polypeptide, for example, glycosylations, acetylations, phosphorylations and the like. In addition, protein fragments, analogs, mutated or variant proteins, fusion proteins and the like are included within the meaning of polypeptide. The polypeptide, protein and peptides may be in cyclic form or they may be in linear form (Piserchio et al. Chem. Biol. (2004) 111:469-473; Li et al., Bioorg. Med. Chem. Lett. (2004) 14:13855-1388; Baruch et al. Biochemistry (2003) 42:2797-2805; Harris et al., Biochemistry (2001) 40:5921-5930).

A "fusion protein" or "fusion polypeptide" as used herein refers to a composite protein, i.e., a single contiguous amino acid sequence, made up of two (or more) distinct, heterologous polypeptides which are not normally fused together in a single amino acid sequence. Thus, a fusion protein can include a single amino acid sequence that contains two entirely distinct amino acid sequences or two similar or identical polypeptide sequences, provided that these sequences are not normally found together in the same configuration in a single amino acid sequence found in nature. Fusion proteins can generally be prepared using either recombinant nucleic acid methods, i.e., as a result of transcription and translation of a recombinant gene fusion product, which fusion comprises a segment encoding a polypeptide of the invention and a segment encoding a heterologous protein, or by chemical synthesis methods well known in the art.

A "fusion protein construct" as used herein is a polynucleotide encoding a fusion protein.

As used herein, the term "PDZ domain" refers to protein sequence (i.e., modular protein domain) of approximately 90 amino acids, characterized by homology to the brain synaptic protein PSD-95, the *Drosophila* septate junction protein Discs-Large (DLG), and the epithelial tight junction protein ZO1 (ZO1). PDZ domains are also known as Discs-Large homology repeats ("DHRs") and GLGF repeats. PDZ domains generally appear to maintain a core consensus sequence (Doyle, D. A., 1996, Cell 85: 1067-76). PDZ domains are found in diverse membrane-associated proteins including members of the MAGUK family of guanylate kinase homologs, several protein phosphatases and kinases, neuronal nitric oxide synthase, and several dystrophin-associated proteins, collectively known as syntrophins.

Exemplary PDZ domain-containing proteins and PDZ domain sequences are shown in TABLE 5. The term "PDZ domain" also encompasses variants (e.g., naturally occurring variants) of the sequences of TABLE 5 (e.g., polymorphic variants, variants with conservative substitutions, and the like). Typically, PDZ domains are substantially identical to those shown in TABLE 5, e.g., at least about 70%, at least about 80%, or at least about 90% amino acid residue identity when compared and aligned for maximum correspondence.

As used herein, the term "PDZ protein" refers to a naturally occurring protein containing a PDZ domain. Exemplary PDZ proteins include, but are not limited to, GORASP1, KIAA0313, KIAA1284, as shown in TABLE 2.

As used herein, the term "PDZ-domain polypeptide" refers to a polypeptide containing a PDZ domain, such as a fusion protein including a PDZ domain sequence, a naturally occurring PDZ protein, or an isolated PDZ domain peptide. Optionally, the instant non-natural PDZ domain polypeptides useful in screening assays may contain e.g. a PDZ domain that is smaller than a natural PDZ domain. For example a non-natural PDZ domain may optionally contain a "GLGF"

motif, i.e., a motif having the GLGF amino acid sequence, which typically resides proximal, e.g. usually within about 10-20 amino acids N-terminal, to an PDZ domain. The latter GLGF motif, and the 3 amino acids immediately N-terminal to the GLGF motif are often required for PDZ binding activity. Similarly, non-natural PDZ domains may be constructed that lack the β-sheet at the C-terminus of a PDZ domain, i.e., this region may often be deleted from the natural PDZ domain without affecting the binding of a PL.

As used herein, the term "PL protein" or "PDZ Ligand protein" refers to a naturally occurring protein that forms a molecular complex with a PDZ-domain, or to a protein whose carboxy-terminus, when expressed separately from the full length protein (e.g., as a peptide fragment of 4-25 residues, e.g., 8, 10, 12, 14 or 16 residues), forms such a molecular complex. The molecular complex can be observed in vitro using the A assay or G assay described infra, or in vivo. This definition is not intended to include anti-PDZ antibodies and the like.

As used herein, the terms "CLCA1" or "CLCA1 protein" refer to the human calcium activated chloride channel CLCA1, the mouse homolog mCLCA3, or the homologs from other mammalian species.

As used herein, the term "CLCA1-PL" or CLCA1 protein that forms a molecular complex with a PDZ domain or to a CLCA protein whose carboxy-terminus, when expressed separately from the full length protein (e.g., as a peptide fragment of 4-25 residues, e.g., 8, 10, 12, 14 or 16 residues), forms such a molecular complex.

As used herein, the term "CLCA1 associated proteins" refers to proteins that interact physically or functionally with CLCA1 proteins.

As used herein, the term "ion channel" refers to an ion channel protein, which could refer singularly or collectively to different ion channels, including CLCA1 proteins or other ion channels.

As used herein, a "PL sequence" refers to the amino acid sequence of the C-terminus of a PL protein (e.g., the C-terminal 2, 3, 4, 5, 6, 7, 8, 9, 10, 12, 14, 16, 20 or 25 residues) ("C-terminal PL sequence") or to an internal sequence known to bind a PDZ domain ("internal PL sequence").

As used herein, a "PL peptide" is a peptide having a sequence from, or based on, the sequence of the C-terminus of a PL protein. Exemplary PL peptides (biotinylated) are listed in TABLE 3 and TABLE 5.

As used herein, a "PL fusion protein" is a fusion protein that has a PL sequence as one domain, typically as the C-terminal domain of the fusion protein. An exemplary PL fusion protein is a tat-PL sequence fusion.

As used herein, the term "PL inhibitor peptide sequence" refers to PL peptide amino acid sequence that (in the form of a peptide or PL fusion protein) inhibits the interaction between a PDZ domain polypeptide and a PL peptide (e.g., in an A assay or a G assay).

As used herein, a "PDZ-domain encoding sequence" means a segment of a polynucleotide encoding a PDZ domain. In various embodiments, the polynucleotide is DNA, RNA, single stranded or double stranded.

As used herein, the terms "antagonist" and "inhibitor," when used in the context of modulating a binding interaction (such as the binding of a PDZ domain sequence to a PL sequence), are used interchangeably and refer to an agent that reduces the binding of the, e.g., PL sequence (e.g., PL peptide) and the, e.g., PDZ domain sequence (e.g., PDZ protein, PDZ domain peptide).

As used herein, the terms "agonist" and "enhancer," when used in the context of modulating a binding interaction (such as the binding of a PDZ domain sequence to a PL sequence), are used interchangeably and refer to an agent that increases the binding of the, e.g., PL sequence (e.g., PL peptide) and the, e.g., PDZ domain sequence (e.g., PDZ protein, PDZ domain peptide).

The terms "isolated" or "purified" means that the object species (e.g., a polypeptide) has been purified from contaminants that are present in a sample, such as a sample obtained from natural sources that contain the object species. If an object species is isolated or purified it is the predominant macromolecular (e.g., polypeptide) species present in a sample (i.e., on a molar basis it is more abundant than any other individual species in the composition), and preferably the object species comprises at least about 50 percent (on a molar basis) of all macromolecular species present. Generally, an isolated, purified or substantially pure composition comprises more than 80 to 90 percent of all macromolecular species present in a composition. Most preferably, the object species is purified to essential homogeneity (i.e., contaminant species cannot be detected in the composition by conventional detection methods), wherein the composition consists essentially of a single macromolecular species.

The term "recombinant" when used with respect to a polypeptide refers to a polypeptide that has been prepared be expressing a recombinant nucleic acid molecule in which different nucleic acid segments have been joined together using molecular biology techniques.

The term "synthesized" when used with respect to a polypeptide generally means that the polypeptide has been prepared by means other than simply purifying the polypeptide from naturally occurring sources. A synthesized polypeptide can thus be prepared by chemical synthesis, recombinant means, or by a combination of chemical synthesis and recombinant means. Segments of a synthesized polypeptide, however, may be obtained from naturally occurring sources.

The term "biological function" or "biological activity" in the context of a cell, refers to a detectable biological activity normally carried out by the cell, e.g., a phenotypic change such as proliferation, cell activation, excitotoxicity responses, neurotransmitter release, cytokine release, degranulation, tyrosine phosphorylation, ion (e.g., calcium) flux, metabolic activity, apoptosis, changes in gene expression, maintenance of cell structure, cell migration, adherence to a substrate, signal transduction, cell-cell interactions, and others described herein or known in the art.

As used herein, the terms "peptide mimetic," "peptidomimetic," and "peptide analog" are used interchangeably and refer to a synthetic chemical compound which has substantially the same structural and/or functional characteristics of a PL inhibitory or PL binding peptide of the invention. The mimetic can be either entirely composed of synthetic, non-natural analogues of amino acids, or is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or inhibitory or binding activity. As with polypeptides of the invention which are conservative variants, routine experimentation will determine whether a mimetic is within the scope of the invention, i.e., that its structure and/or function is not substantially altered. Thus, a mimetic composition is within the scope of the invention if it is capable of binding to a PDZ domain and/or inhibiting a PL-PDZ interaction.

Polypeptide mimetic compositions can contain any combination of nonnatural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like.

A polypeptide can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N=-dicyclohexylcarbodiimide (DCC) or N,N=-diisopropylcarbodiimide (DIC). Linking groups that can be an alternative to the traditional amide bond ("peptide bond") linkages include, e.g., ketomethylene (e.g., —C(=O)—CH$_2$— for —C(=O)—NH—), aminomethylene (CH$_2$—NH), ethylene, olefin (CH=CH), ether (CH$_2$—O), thioether (CH$_2$—S), tetrazole (CN$_4$—), thiazole, retroamide, thioamide, or ester (see, e.g., Spatola (1983) in *Chemistry and Biochemistry of Amino Acids, Peptides and Proteins*, Vol. 7, pp 267-357, *A Peptide Backbone Modifications*, Marcel Dekker, NY).

A polypeptide can also be characterized as a mimetic by containing all or some non-natural residues in place of naturally occurring amino acid residues. Nonnatural residues are well described in the scientific and patent literature; a few exemplary nonnatural compositions useful as mimetics of natural amino acid residues and guidelines are described below.

Mimetics of aromatic amino acids can be generated by replacing by, e.g., D- or L-naphylalanine; D- or L-phenylglycine; D- or L-2 thieneylalanine; D- or L-1, -2,3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluorophenylalanine; D- or L-p-biphenylphenylalanine; K- or L-p-methoxybiphenylphenylalanine; D- or L-2-indole(alkyl)alanines; and, D- or L-alkylainines, where alkyl can be substituted or unsubstituted methyl, ethyl, propyl, hexyl, butyl, pentyl, isopropyl, iso-butyl, sec-isotyl, iso-pentyl, or a non-acidic amino acids. Aromatic rings of a nonnatural amino acid include, e.g., thiazolyl, thiophenyl, pyrazolyl, benzimidazolyl, naphthyl, furanyl, pyrrolyl, and pyridyl aromatic rings.

Mimetics of acidic amino acids can be generated by substitution by, e.g., non-carboxylate amino acids while maintaining a negative charge; (phosphono)alanine; sulfated threonine. Carboxyl side groups (e.g., aspartyl or glutamyl) can also be selectively modified by reaction with carbodiimides (R=—N—C—N—R=) such as, e.g., 1-cyclohexyl-3 (2-morpholinyl-(4-ethyl)carbodiimide or 1-ethyl-3(4-azonia-4,4-dimetholpentyl)carbodiimide. Aspartyl or glutamyl can also be converted to asparaginyl and glutaminyl residues by reaction with ammonium ions.

Mimetics of basic amino acids can be generated by substitution with, e.g., (in addition to lysine and arginine) the amino acids ornithine, citrulline, or (guanidino)-acetic acid, or (guanidino)alkyl-acetic acid, where alkyl is defined above. Nitrile derivative (e.g., containing the CN-moiety in place of COOH) can be substituted for asparagine or glutamine. Asparaginyl and glutaminyl residues can be deaminated to the corresponding aspartyl or glutamyl residues.

Arginine residue mimetics can be generated by reacting arginyl with, e.g., one or more conventional reagents, including, e.g., phenylglyoxal, 2,3-butanedione, 1,2-cyclohexanedione, or ninhydrin, preferably under alkaline conditions.

Tyrosine residue mimetics can be generated by reacting tyrosyl with, e.g., aromatic diazonium compounds or tetranitromethane. N-acetylimidizol and tetranitromethane can be used to form O-acetyl tyrosyl species and 3-nitro derivatives, respectively.

Cysteine residue mimetics can be generated by reacting cysteinyl residues with, e.g., alpha-haloacetates such as 2-chloroacetic acid or chloroacetamide and corresponding amines; to give carboxymethyl or carboxyamidomethyl derivatives. Cysteine residue mimetics can also be generated by reacting cysteinyl residues with, e.g., bromo-trifluoroacetone, alpha-bromo-beta-(5-imidozoyl)propionic acid; chloroacetyl phosphate, N-alkylmaleimides, 3-nitro-2-pyridyl disulfide; methyl 2-pyridyl disulfide; p-chloromercuribenzoate; 2-chloromercuri-4 nitrophenol; or, chloro-7-nitrobenzo-oxa-1,3-diazole.

Lysine mimetics can be generated (and amino terminal residues can be altered) by reacting lysinyl with, e.g., succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitrobenzenesulfonic acid, O-methylisourea, 2,4, pentanedione, and transamidase-catalyzed reactions with glyoxylate.

Mimetics of methionine can be generated by reaction with, e.g., methionine sulfoxide. Mimetics of proline include, e.g., pipecolic acid, thiazolidine carboxylic acid, 3- or 4-hydroxy proline, dehydroproline, 3- or 4-methylproline, or 3,3,-dimethylproline. Histidine residue mimetics can be generated by reacting histidyl with, e.g., diethylprocarbonate or para-bromophenacyl bromide.

Other mimetics include, e.g., those generated by hydroxylation of proline and lysine; phosphorylation of the hydroxyl groups of seryl or threonyl residues; methylation of the alpha-amino groups of lysine, arginine and histidine; acetylation of the N-terminal amine; methylation of main chain amide residues or substitution with N-methyl amino acids; or amidation of C-terminal carboxyl groups.

A component of a natural polypeptide (e.g., a PL polypeptide or PDZ polypeptide) can also be replaced by an amino acid (or peptidomimetic residue) of the opposite chirality. Thus, any amino acid naturally occurring in the L-configuration (which can also be referred to as the R or S, depending upon the structure of the chemical entity) can be replaced with the amino acid of the same chemical structural type or a peptidomimetic, but of the opposite chirality, generally referred to as the D-amino acid, but which can additionally be referred to as the R- or S-form.

The mimetics of the invention can also include compositions that contain a structural mimetic residue, particularly a residue that induces or mimics secondary structures, such as a beta turn, beta sheet, alpha helix structures, gamma turns, and the like. For example, substitution of natural amino acid residues with D-amino acids; N-alpha-methyl amino acids; C-alpha-methyl amino acids; or dehydroamino acids within a peptide can induce or stabilize beta turns, gamma turns, beta sheets or alpha helix conformations. Beta turn mimetic structures have been described, e.g., by Nagai (1985) Tet. Lett. 26:647-650; Feigl (1986) J. Amer. Chem. Soc. 108:181-182; Kahn (1988) J. Amer. Chem. Soc. 110:1638-1639; Kemp (1988) Tet. Lett. 29:5057-5060; Kahn (1988) J. Molec. Recognition 1:75-79. Beta sheet mimetic structures have been described, e.g., by Smith (1992) J. Amer. Chem. Soc. 114: 10672-10674. For example, a type VI beta turn induced by a cis amide surrogate, 1,5-disubstituted tetrazol, is described by Beusen (1995) Biopolymers 36:181-200. Incorporation of achiral omega-amino acid residues to generate polymethylene units as a substitution for amide bonds is described by Banerjee (1996) Biopolymers 39:769-777. Secondary structures of polypeptides can be analyzed by, e.g., high-field 1H NMR or 2D NMR spectroscopy, see, e.g., Higgins (1997) J. Pept. Res. 50:421-435. See also, Hruby (1997) Biopolymers 43:219-266, Balaji, et al., U.S. Pat. No. 5,612,895.

As used herein, "peptide variants" and "conservative amino acid substitutions" refer to peptides that differ from a reference peptide (e.g., a peptide having the sequence of the carboxy-terminus of a specified PL protein) by substitution of an amino acid residue having similar properties (based on size, polarity, hydrophobicity, and the like). Thus, insofar as the compounds that are encompassed within the scope of the invention are partially defined in terms of amino acid residues of designated classes, the amino acids may be generally categorized into three main classes: hydrophilic amino acids, hydrophobic amino acids and cysteine-like amino acids, depending primarily on the characteristics of the amino acid side chain. These main classes may be further divided into subclasses. Hydrophilic amino acids include amino acids having acidic, basic or polar side chains and hydrophobic amino acids include amino acids having aromatic or apolar side chains. Apolar amino acids may be further subdivided to include, among others, aliphatic amino acids. The definitions of the classes of amino acids as used herein are as follows:

"Hydrophobic Amino Acid" refers to an amino acid having a side chain that is uncharged at physiological pH and that is repelled by aqueous solution. Examples of genetically encoded hydrophobic amino acids include Ile, Leu and Val. Examples of non-genetically encoded hydrophobic amino acids include t-BuA.

"Aromatic Amino Acid" refers to a hydrophobic amino acid having a side chain containing at least one ring having a conjugated electron system (aromatic group). The aromatic group may be further substituted with groups such as alkyl, alkenyl, alkynyl, hydroxyl, sulfanyl, nitro and amino groups, as well as others. Examples of genetically encoded aromatic amino acids include Phe, Tyr and Trp. Commonly encountered non-genetically encoded aromatic amino acids include phenylglycine, 2-naphthylalanine, (3-2-thienylalanine, 1,2,3,4-tetrahydroisoquinoline-3-carboxylic acid, 4-chloro-phenylalanine, 2-fluorophenyl-alanine, 3-fluorophenylalanine and 4-fluorophenylalanine.

"Apolar Amino Acid" refers to a hydrophobic amino acid having a side chain that is generally uncharged at physiological pH and that is not polar. Examples of genetically encoded apolar amino acids include Gly, Pro and Met. Examples of non-encoded apolar amino acids include Cha.

"Aliphatic Amino Acid" refers to an apolar amino acid having a saturated or unsaturated straight chain, branched or cyclic hydrocarbon side chain. Examples of genetically encoded aliphatic amino acids include Ala, Leu, Val and Ile. Examples of non-encoded aliphatic amino acids include Nle.

"Hydrophilic Amino Acid" refers to an amino acid having a side chain that is attracted by aqueous solution. Examples of genetically encoded hydrophilic amino acids include Ser and Lys. Examples of non-encoded hydrophilic amino acids include Cit and hCys.

"Acidic Amino Acid" refers to a hydrophilic amino acid having a side chain pK value of less than 7. Acidic amino acids typically have negatively charged side chains at physiological pH due to loss of a hydrogen ion. Examples of genetically encoded acidic amino acids include Asp and Glu.

"Basic Amino Acid" refers to a hydrophilic amino acid having a side chain pK value of greater than 7. Basic amino acids typically have positively charged side chains at physiological pH due to association with hydronium ion. Examples of genetically encoded basic amino acids include Arg, Lys and His. Examples of non-genetically encoded basic amino acids include the non-cyclic amino acids ornithine, 2,3-diaminopropionic acid, 2,4-diaminobutyric acid and homoarginine.

"Polar Amino Acid" refers to a hydrophilic amino acid having a side chain that is uncharged at physiological pH, but which has a bond in which the pair of electrons shared in common by two atoms is held more closely by one of the atoms. Examples of genetically encoded polar amino acids include Asx and Glx. Examples of non-genetically encoded polar amino acids include citrulline, N-acetyl lysine and methionine sulfoxide.

"Cysteine-Like Amino Acid" refers to an amino acid having a side chain capable of forming a covalent linkage with a side chain of another amino acid residue, such as a disulfide linkage. Typically, cysteine-like amino acids generally have a side chain containing at least one thiol (SH) group. Examples of genetically encoded cysteine-like amino acids include Cys. Examples of non-genetically encoded cysteine-like amino acids include homocysteine and penicillamine.

As will be appreciated by those having skill in the art, the above classification are not absolute—several amino acids exhibit more than one characteristic property, and can therefore be included in more than one category. For example, tyrosine has both an aromatic ring and a polar hydroxyl group. Thus, tyrosine has dual properties and can be included in both the aromatic and polar categories. Similarly, in addition to being able to form disulfide linkages, cysteine also has apolar character. Thus, while not strictly classified as a hydrophobic or apolar amino acid, in many instances cysteine can be used to confer hydrophobicity to a peptide.

Certain commonly encountered amino acids which are not genetically encoded of which the peptides and peptide analogues of the invention may be composed include, but are not limited to, β-alanine (b-Ala) and other omega-amino acids such as 3-aminopropionic acid (Dap), 2,3-diaminopropionic acid (Dpr), 4-aminobutyric acid and so forth; α-aminoisobutyric acid (Aib); ε-aminohexanoic acid (Aha); δ-aminovaleric acid (Ava); N-methylglycine or sarcosine (MeGly); ornithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle); 2-naphthylalanine (2-Nal); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); (3-2-thienylalanine (Thi); methionine sulfoxide (MSO); homoarginine (hArg); N-acetyl lysine (AcLys); 2,3-diaminobutyric acid (Dab); 2,3-diaminobutyric acid (Dbu); p-aminophenylalanine (Phe(pNH$_2$)); N-methyl valine (MeVal); homocysteine (hCys) and homoserine (hSer). These amino acids also fall conveniently into the categories defined above.

The classifications of the above-described genetically encoded and non-encoded amino acids are summarized in TABLE 1, below. It is to be understood that TABLE 1 is for illustrative purposes only and does not purport to be an exhaustive list of amino acid residues which may comprise the peptides and peptide analogues described herein. Other amino acid residues which are useful for making the peptides and peptide analogues described herein can be found, e.g., in Fasman, 1989, *CRC Practical Handbook of Biochemistry and Molecular Biology*, CRC Press, Inc., and the references cited therein. Amino acids not specifically mentioned herein can be conveniently classified into the above-described categories on the basis of known behavior and/or their characteristic chemical and/or physical properties as compared with amino acids specifically identified.

TABLE 1

| Classification | Genetically Encoded | Genetically Non-Encoded |
|---|---|---|
| Hydrophobic | | |
| Aromatic | F, Y, W | Phg, Nal, Thi, Tic, Phe(4-Cl), Phe(2-F), Phe(3-F), Phe(4-F), Pyridyl Ala, |
| Apolar | M, G, P | Benzothienyl Ala |
| Aliphatic | A, V, L, I | t-BuA, t-BuG, MeIle, Nle, MeVal, Cha, bAla, MeGly, Aib |
| Hydrophilic | | |
| Acidic | D, E | |
| Basic | H, K, R | Dpr, Orn, hArg, Phe(p-$NH_2$), DBU, $A_2$BU |
| Polar | Q, N, S, T, Y | Cit, AcLys, MSO, hSer |
| Cysteine-Like | C | Pen, hCys, p-methyl Cys |

As used herein, a "detectable label" has the ordinary meaning in the art and refers to an atom (e.g., radionuclide), molecule (e.g., fluorescein), or complex, that is or can be used to detect (e.g., due to a physical or chemical property), indicate the presence of a molecule or to enable binding of another molecule to which it is covalently bound or otherwise associated. The term "label" also refers to covalently bound or otherwise associated molecules (e.g., a biomolecule such as an enzyme) that act on a substrate to produce a detectable atom, molecule or complex. Detectable labels suitable for use in the present invention include any composition detectable by spectroscopic, photochemical, biochemical, immunochemical, electrical, optical or chemical means. Labels useful in the present invention include biotin for staining with labeled streptavidin conjugate, magnetic beads (e.g., Dynabeads™), fluorescent dyes (e.g., fluorescein, Texas red, rhodamine, green fluorescent protein, enhanced green fluorescent protein, and the like), radiolabels (e.g., $^3$H, $^{125}$I, $^{35}$S, $^{14}$C, or $^{32}$P), enzymes (e.g., hydrolases, particularly phosphatases such as alkaline phosphatase, esterases and glycosidases, or oxidoreductases, particularly peroxidases such as horseradish peroxidase, and others commonly used in ELISAs), substrates, cofactors, inhibitors, chemiluminescent groups, chromogenic agents, and colorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241. Means of detecting such labels are well known to those of skill in the art. Thus, for example, radiolabels and chemiluminescent labels may be detected using photographic film or scintillation counters, fluorescent markers may be detected using a photodetector to detect emitted light (e.g., as in fluorescence-activated cell sorting). Enzymatic labels are typically detected by providing the enzyme with a substrate and detecting the reaction product produced by the action of the enzyme on the substrate, and colorimetric labels are detected by simply visualizing the colored label. Thus, a label is any composition detectable by spectroscopic, photochemical, biochemical, immunochemical, electrical, optical or chemical means. The label may be coupled directly or indirectly to the desired component of the assay according to methods well known in the art. Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal generating system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody. The molecules can also be conjugated directly to signal generating compounds, e.g., by conjugation with an enzyme or fluorophore. Means of detecting labels are well known to those of skill in the art. Thus, for example, where the label is a radioactive label, means for detection include a scintillation counter, photographic film as in autoradiography, or storage phosphor imaging. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Also, simple colorimetric labels may be detected by observing the color associated with the label. It will be appreciated that when pairs of fluorophores are used in an assay, it is often preferred that they have distinct emission patterns (wavelengths) so that they can be easily distinguished.

As used herein, the term "substantially identical" in the context of comparing amino acid sequences, means that the sequences have at least about 70%, at least about 80%, or at least about 90% amino acid residue identity when compared and aligned for maximum correspondence. An algorithm that is suitable for determining percent sequence identity and sequence similarity is the FASTA algorithm, which is described in Pearson, W. R. & Lipman, D. J., 1988, *Proc. Natl. Acad. Sci. U.S.A.* 85: 2444. See also W. R. Pearson, 1996, *Methods Enzymol.* 266: 227-258. Preferred parameters used in a FASTA alignment of DNA sequences to calculate percent identity are optimized, BL50 Matrix 15: −5, k-tuple=2; joining penalty=40, optimization=28; gap penalty −12, gap length penalty=−2; and width=16.

As used herein, the terms "test compound" or "test agent" are used interchangeably and refer to a candidate agent that may have enhancer/agonist, or inhibitor/antagonist activity, e.g., inhibiting or enhancing an interaction such as PDZ-PL binding. The candidate agents or test compounds may be any of a large variety of compounds, both naturally occurring and synthetic, organic and inorganic, and including polymers (e.g., oligopeptides, polypeptides, oligonucleotides, and polynucleotides), small molecules, antibodies (as broadly defined herein), sugars, fatty acids, nucleotides and nucleotide analogs, analogs of naturally occurring structures (e.g., peptide mimetics, nucleic acid analogs, and the like), and numerous other compounds. In certain embodiment, test agents are prepared from diversity libraries, such as random or combinatorial peptide or non-peptide libraries. Many libraries are known in the art that can be used, e.g., chemically synthesized libraries, recombinant (e.g., phage display libraries), and in vitro translation-based libraries. Examples of chemically synthesized libraries are described in Fodor et al., 1991, *Science* 251:767-773; Houghten et al., 1991, *Nature* 354:84-86; Lam et al., 1991, *Nature* 354:82-84; Medynski, 1994, *Bio/Technology* 12:709-710; Gallop et al., 1994, *J. Medicinal Chemistry* 37(9):1233-1251; Ohlmeyer et al., 1993, *Proc. Natl. Acad. Sci. USA* 90:10922-10926; Erb et al., 1994, *Proc. Natl. Acad. Sci. USA* 91:11422-11426; Houghten et al., 1992, *Biotechniques* 13:412; Jayawickreme et al., 1994,

*Proc. Natl. Acad. Sci. USA* 91:1614-1618; Salmon et al., 1993, *Proc. Natl. Acad. Sci. USA* 90:11708-11712; PCT Publication No. WO 93/20242; and Brenner and Lerner, 1992, *Proc. Natl. Acad. Sci. USA* 89:5381-5383. Examples of phage display libraries are described in Scott and Smith, 1990, *Science* 249:386-390; Devlin et al., 1990, *Science,* 249:404-406; Christian, R. B., et al., 1992, *J. Mol. Biol.* 227:711-718); Lenstra, 1992, *J. Immunol. Meth.* 152:149-157; Kay et al., 1993, *Gene* 128:59-65; and PCT Publication No. WO 94/18318 dated Aug. 18, 1994. In vitro translation-based libraries include but are not limited to those described in PCT Publication No. WO 91/05058 dated Apr. 18, 1991; and Mattheakis et al., 1994, *Proc. Natl. Acad. Sci. USA* 91:9022-9026. By way of examples of nonpeptide libraries, a benzodiazepine library (see e.g., Bunin et al., 1994, *Proc. Natl. Acad. Sci. USA* 91:4708-4712) can be adapted for use. Peptoid libraries (Simon et al., 1992, *Proc. Natl. Acad. Sci. USA* 89:9367-9371) can also be used. Another example of a library that can be used, in which the amide functionalities in peptides have been permethylated to generate a chemically transformed combinatorial library, is described by Ostresh et al. (1994, *Proc. Natl. Acad. Sci. USA* 91:11138-11142).

The term "specific binding" refers to binding between two molecules, for example, a ligand and a receptor, characterized by the ability of a molecule (ligand) to associate with another specific molecule (receptor) even in the presence of a plurality of other diverse molecules, i.e., to show preferential binding of one molecule for another in a heterogeneous mixture of molecules. Specific binding of a ligand to a receptor is also evidenced by reduced binding of a detectably labeled ligand to the receptor in the presence of excess unlabeled ligand (i.e., a binding competition assay).

As used herein, a "plurality" of PDZ proteins (or corresponding PDZ domains or PDZ fusion polypeptides) has its usual meaning. In some embodiments, (Susan our US associate has cautioned us to remove phrases such as "in one embodiment" as the applicant may be required to include all of these features as limitations in the claims. I am not sure if you agree, it is now our practice to use the phrase "in certain embodiments" OK with me the plurality is at least 5, and often at least 25, at least 40, or at least 60 different PDZ proteins. In some embodiments, the plurality is selected from the list of PDZ polypeptides listed in TABLE 2. In some embodiments, the plurality of different PDZ proteins are from (i.e., expressed in) a particular specified tissue or a particular class or type of cell. In some embodiments, the plurality of different PDZ proteins represents a substantial fraction (e.g., typically at least 50%, more often at least 80%) of all of the PDZ proteins known to be, or suspected of being, expressed in the tissue or cell(s), e.g., all of the PDZ proteins known to be present in neurons. In some embodiments, the plurality is at least 50%, usually at least 80%, at least 90% or all of the PDZ proteins disclosed herein as being expressed in a particular cell.

When referring to PL peptides (or the corresponding proteins, e.g., corresponding to those listed in TABLE 3, TABLE 5, TABLE 6, or elsewhere herein) a "plurality" may refer to at least 5, at least 10, and often at least 25 PLs such as those specifically listed herein, or to the classes and percentages set forth supra for PDZ domains.

A difference in general is typically considered to be "statistically significant" if the difference is less than experimental error. Thus a difference is considered statistically significant if the probability of the observed difference occurring by chance (the p-value) is less than some predetermined level. As used herein a "statistically significant difference" can refer to a p-value that is <0.05, preferably <0.01 and most preferably <0.001.

II. General

The present inventors have identified interactions between PDZ proteins and proteins that contain a PL motif that are involved in various biological functions in different types of cells. Some of these interactions involve PDZ:PL protein interactions between proteins that have important roles in lung cells. As such, modulation of these interactions has direct implications for the treatment of various pulmonary disorders, including but not limited to including asthma, chronic obstructive pathway disease, including emphysema and chronic bronchitis, and disorders associated with improper mucus secretion.

The inventors have identified distinct strategies for treating various pulmonary disorders based on PDZ:PL interactions. The inventors have determined common structural features of a class of polypeptides that are effective in disrupting the interaction between a CLCA1 protein and PDZ domain-containing polypeptides. The current inventors have thus identified compounds that inhibit the interactions between these different proteins, as well as developed methods for designing additional compounds.

One general class of inhibitors is those that mimic the carboxy terminus of a PL protein and thus interfere with the ability of the carboxy terminus of the PL protein to bind its cognate PDZ protein. Another general class of inhibitors includes the PDZ domain from a PDZ protein that is involved in an interaction that is to be disrupted. These inhibitors bind the PL protein that is the cognate ligand for the PDZ protein of interest and thus prevent binding between the PL protein and PDZ protein. Because the PDZ:PL protein interactions that are described herein are involved in the biological activity of mammalian, and especially lung cells, the inhibitors that are provided can be used to inhibit PDZ:PL protein interactions for the treatment of pulmonary disorders such as asthma, chronic obstructive pathway disease, including emphysema and chronic bronchitis, and disorders associated with improper mucus secretion. Methods for determining whether a test compound acts a modulator of a particular PDZ protein and PL protein binding pair are also described.

For those PDZ proteins containing multiple PDZ domains, the methods that are provided can be utilized to determine to which specific domain(s) a particular PL protein of interest binds. The methods can thus be utilized to identify or design inhibitors that have increased selectivity for a particular PDZ domain. The methods that are disclosed can also be used to identify inhibitors with high binding affinity.

Although the foregoing classes of inhibitors are based upon the C-terminal sequences of PL proteins that bind a PDZ protein, as alluded to above, another class of inhibitors includes polypeptides that include all or a part of a PDZ domain that binds to the PL sequence of a CLCA1 protein. Because inhibitors in this class typically include most or the entire PDZ domain, polypeptide inhibitors in this class typically are at least 50-70 amino acids in length.

The various classes of polypeptide inhibitors just described can also be fusion proteins. These generally include a PL inhibitor peptide sequence that is fused to another sequence that encodes a separate protein domain. One specific example of an inhibitory fusion protein is one in which a PL sequence (e.g., one of those listed in TABLE 5 or TABLE 6) is coupled to a transmembrane transporter peptide. As described in greater detail infra, a variety of different transmembrane transporter peptides can be utilized.

Although certain classes of inhibitors such as those just described are polypeptides, other inhibitors are peptide mimetics or variants of these polypeptides as described in greater detail infra. Regardless of type, the inhibitors typically had $IC_{50}$ values less than 50 µM, 25 µM, 10 µM, 0.1 µM or 0.01 µM. In general the inhibitors typically have an $IC_{50}$ value of between 0.1-1 µM. These inhibitors can be formulated as pharmaceutical compositions and then used in the treatment of various neurological disorders such as those listed above.

The following sections provide additional details regarding the identification of PDZ:PL interactions in lung cells, the structural characteristics of inhibitors that disrupt these interactions and treatment methods utilizing such inhibitors.

III. Identification of Candidate PL Proteins and Synthesis of Peptides

A PL protein (short for PDZ Ligand protein), such as the CACL proteins described herein, is a protein (or a C-terminal fragment thereof) that can bind PDZ proteins via its carboxy terminus. PDZ proteins, in turn, are proteins with PDZ domains, which are domains common to three prototypical proteins: post synaptic density protein -95 (PSD-95), *Drosophila* large disc protein and Zonula Occludin 1 protein (see, e.g., Gomperts et al., 1996, *Cell* 84:659-662; see also, Songyang et al., 1997, *Science* 275:73; and Doyle et al., 1996, *Cell* 88:1067-1076). As described in greater detail herein, PL proteins have certain carboxy terminal motifs that enable these proteins to functions as ligands to PDZ proteins. When these carboxy terminal regions are referred to, the positioning of the carboxy terminal residues are sometimes referred to herein by a numbered position, which is illustrated in the following scheme:

| Position: | −3 | −2 | −1 | 0 (C- terminal) |
| --- | --- | --- | --- | --- |

Certain PDZ domains are bound by the C-terminal residues of PDZ-binding proteins.

A. Preparation of Peptides

1) Chemical Synthesis

Technique for the preparation of peptides and peptide analogues of the current invention are well known in the art. For example, the peptides may be prepared in linear form using conventional solution or solid phase peptide syntheses and cleaved from the resin followed by purification procedures (Creighton, 1983, *Protein Structures And Molecular Principles*, W.H. Freeman and Co., N.Y.). Suitable procedures for synthesizing the peptides described herein are well known in the art. The composition of the synthetic peptides may be confirmed by amino acid analysis or sequencing (e.g., the Edman degradation procedure and mass spectroscopy).

In addition, analogues and derivatives of the peptides can be chemically synthesized. The linkage between each amino acid of the peptides of the invention may be an amide, a substituted amide or an isostere of amide. Nonclassical amino acids or chemical amino acid analogues can be introduced as a substitution or addition into the sequence. Non-classical amino acids include, but are not limited to, the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogues in general. Furthermore, the amino acid can be D (dextrorotary) or L (levorotary).

Synthetic peptides of defined sequence (e.g., corresponding to the carboxyl-termini of the indicated proteins) can be synthesized by any standard resin-based method (see, e.g., U.S. Pat. No. 4,108,846; see also, Caruthers et al., 1980, *Nucleic Acids Res. Symp. Ser.*, 215-223; Horn et al., 1980, *Nucleic Acids Res. Symp. Ser.*, 225-232; Roberge, et al., 1995, *Science* 269:202). The peptides used in the assays described herein were prepared by the FMOC (see, e.g., Guy and Fields, 1997, *Meth. Enz.* 289:67-83; Wellings and Atherton, 1997, *Meth. Enz.* 289:44-67). In some cases (e.g., for use in the A and G assays of the invention), peptides were labeled with biotin at the amino-terminus by reaction with a four-fold excess of biotin methyl ester in dimethylsulfoxide with a catalytic amount of base. The peptides were cleaved from the resin using a halide containing acid (e.g. trifluoroacetic acid) in the presence of appropriate antioxidants (e.g. ethanedithiol) and excess solvent lyophilized.

2) Recombinant Synthesis

If the peptide is composed entirely of gene-encoded amino acids, or a portion of it is so composed, the peptide or the relevant portion may also be synthesized using conventional recombinant genetic engineering techniques. For recombinant production, a polynucleotide sequence encoding a linear form of the peptide is inserted into an appropriate expression vehicle, i.e., a vector which contains the necessary elements for the transcription and translation of the inserted coding sequence, or in the case of an RNA viral vector, the necessary elements for replication and translation. The expression vehicle is then transfected into a suitable target cell which will express the peptide. Depending on the expression system used, the expressed peptide is then isolated by procedures well-established in the art. Methods for recombinant protein and peptide production are well known in the art (see, e.g., Maniatis et al., 1989, *Molecular Cloning A Laboratory Manual*, Cold Spring Harbor Laboratory, N.Y.; and Ausubel et al., 1989, *Current Protocols in Molecular Biology*, Greene Publishing Associates and Wiley Interscience, N.Y.).

A variety of host-expression vector systems may be utilized to express the peptides described herein. These include, but are not limited to, microorganisms such as bacteria transformed with recombinant bacteriophage DNA or plasmid DNA expression vectors containing an appropriate coding sequence; yeast or filamentous fungi transformed with recombinant yeast or fungi expression vectors containing an appropriate coding sequence; insect cell systems infected with recombinant virus expression vectors (e.g., baculovirus) containing an appropriate coding sequence; plant cell systems infected with recombinant virus expression vectors (e.g., cauliflower mosaic virus or tobacco mosaic virus) or transformed with recombinant plasmid expression vectors (e.g., Ti plasmid) containing an appropriate coding sequence; or animal cell systems.

The expression elements of the expression systems vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage =, plac, ptrp, ptac (ptrp-lac hybrid promoter) and the like may be used; when cloning in insect cell systems, promoters such as the baculovirus polyhedron promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5 K promoter) may be used; when generating cell lines that contain multiple copies of expression product, SV40-, BPV- and EBV-based vectors may be used with an appropriate selectable marker.

In cases where plant expression vectors are used, the expression of sequences encoding the peptides of the invention may be driven by any of a number of promoters. For example, viral promoters such as the 35S RNA and 19S RNA promoters of CaMV (Brisson et al., 1984, Nature 310:511-514), or the coat protein promoter of TMV (Takamatsu et al., 1987, EMBO J. 6:307-311) may be used; alternatively, plant promoters such as the small subunit of RUBISCO (Coruzzi et al., 1984, EMBO J. 3:1671-1680; Broglie et al., 1984, Science 224:838-843) or heat shock promoters, e.g., soybean hsp17.5-E or hsp17.3-B (Gurley et al., 1986, Mol. Cell. Biol. 6:559-565) may be used. These constructs can be introduced into planleukocytes using Ti plasmids, Ri plasmids, plant virus vectors, direct DNA transformation, microinjection, electroporation, etc. For reviews of such techniques see, e.g., Weissbach & Weissbach, 1988, *Methods for Plant Molecular Biology*, Academic Press, NY, Section VIII, pp. 421-463; and Grierson & Corey, 1988, *Plant Molecular Biology*, 2d Ed., Blackie, London, Ch. 7-9.

In one insect expression system that may be used to produce the peptides of the invention, *Autographa californica* nuclear polyhidrosis virus (AcNPV) is used as a vector to express the foreign genes. The virus grows in *Spodoptera frugiperda* cells. A coding sequence may be cloned into nonessential regions (for example the polyhedron gene) of the virus and placed under control of an AcNPV promoter (for example, the polyhedron promoter). Successful insertion of a coding sequence will result in inactivation of the polyhedron gene and production of non-occluded recombinant virus (i.e., virus lacking the proteinaceous coat coded for by the polyhedron gene). These recombinant viruses are then used to infect *Spodoptera frugiperda* cells in which the inserted gene is expressed. (e.g., see Smith et al., 1983, J. Virol. 46:584; Smith, U.S. Pat. No. 4,215,051). Further examples of this expression system may be found in *Current Protocols in Molecular Biology*, Vol. 2, Ausubel et al., eds., Greene Publish. Assoc. & Wiley Interscience.

In mammalian host cells, a number of viral based expression systems may be utilized. In cases where an adenovirus is used as an expression vector, a coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing peptide in infected hosts. (e.g., See Logan & Shenk, 1984, Proc. Natl. Acad. Sci. USA 81:3655-3659). Alternatively, the vaccinia 7.5 K promoter may be used, (see, e.g., Mackett et al., 1982, Proc. Natl. Acad. Sci. USA 79:7415-7419; Mackett et al., 1984, J. Virol. 49:857-864; Panicali et al., 1982, Proc. Natl. Acad. Sci. USA 79:4927-4931).

Other expression systems for producing linear peptides of the invention will be apparent to those having skill in the art.

B. Purification of Peptides and Peptide Analogues

The peptides and peptide analogues of the invention can be purified by art-known techniques such as high performance liquid chromatography, ion exchange chromatography, gel electrophoresis, affinity chromatography and the like. The actual conditions used to purify a particular peptide or analogue will depend, in part, on factors such as net charge, hydrophobicity, hydrophilicity, etc., and will be apparent to those having skill in the art. The purified peptides can be identified by assays based on their physical or functional properties, including radioactive labeling followed by gel electrophoresis, radioimmuno-assays, ELISA, bioassays, and the like.

For affinity chromatography purification, any antibody which specifically binds the peptides or peptide analogues may be used. For the production of antibodies, various host animals, including but not limited to rabbits, mice, rats, etc., may be immunized by injection with a peptide. The peptide may be attached to a suitable carrier, such as BSA or KLH, by means of a side chain functional group or linkers attached to a side chain functional group. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette-Guerin) and *Corynebacterium parvum*.

Monoclonal antibodies to a peptide may be prepared using any technique which provides for the production of antibody molecules by continuous cell lines in culture. These include but are not limited to the hybridoma technique originally described by Koehler and Milstein, 1975, Nature 256:495-497, the human B-cell hybridoma technique, Kosbor et al., 1983, Immunology Today 4:72; Cote et al., 1983, Proc. Natl. Acad. Sci. U.S.A. 80:2026-2030 and the EBV-hybridoma technique (Cole et al., 1985, *Monoclonal Antibodies and Cancer Therapy*, Alan R. Liss, Inc., pp. 77-96 (1985)). In addition, techniques developed for the production of "chimeric antibodies" (Morrison et al., 1984, Proc. Natl. Acad. Sci. U.S.A. 81:6851-6855; Neuberger et al., 1984, Nature 312:604-608; Takeda et al., 1985, Nature 314:452-454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce peptide-specific single chain antibodies.

Antibody fragments which contain deletions of specific binding sites may be generated by known techniques. For example, such fragments include but are not limited to F(ab')$_2$ fragments, which can be produced by pepsin digestion of the antibody molecule and Fab fragments, which can be generated by reducing the disulfide bridges of the F(ab')$_2$ fragments. Alternatively, Fab expression libraries may be constructed (Huse et al., 1989, Science 246:1275-1281) to allow rapid and easy identification of monoclonal Fab fragments with the desired specificity for the peptide of interest.

The antibody or antibody fragment specific for the desired peptide can be attached, for example, to agarose, and the antibody-agarose complex is used in immunochromatography to purify peptides of the invention. See, Scopes, 1984, *Protein Purification: Principles and Practice*, Springer-Verlag New York, Inc., NY, Livingstone, 1974, Methods Enzymology: Immunoaffinity Chromatography of Proteins 34:723-731.

For the peptides used in the present invention, cleavage from resin and lyophilization was followed by peptides being redissolved and purified by reverse phase high performance liquid chromatography (HPLC). One appropriate HPLC solvent system involves a Vydac C-18 semi-preparative column running at 5 ml per minute with increasing quantities of acetonitrile plus 0.1% trifluoroacetic acid in a base solvent of water plus 0.1% trifluoroacetic acid. After HPLC purification, the identities of the peptides are confirmed by MALDI cation-mode mass spectrometry. As noted, exemplary biotinylated peptides are provided in TABLE 3 and TABLE 5.

V. PDZ Protein and PL Protein Interactions

TABLE 3 lists PDZ proteins and other PL proteins which the current inventors have identified as binding to one another.

TABLE 2 lists the sequences of the PDZ domains cloned into a vector (PGEX-3X vector) for production of GST-PDZ fusion proteins (Pharmacia). Column 1 shows the gene name, column 2 shows alternative names by which the gene is known, column 3 shows the sequence fused to the GST construct and column 4 shows the GenBank GI or Accession number.

TABLE 2

| | | PDZ domains binding hCLCA1/mCLCA3 | |
|---|---|---|---|
| Name | Alternates | Sequence for testing | GI # |
| KIAA0313 | PDZ-GEF1, RA-GEF | HLRLLNIACAAKAKRRLMTLTKPSREAPLPFILLGGSEK GFGIFVDSVDSGSKATEAGLKRGDQILEVNGQNFENIQ LSKAMEILRNNTHLSITVKTNLFVFKELLTRLSEEKRNG AP (SEQ ID NO: 1) | 40788210 34395737 |
| GRASP1 | GRASP65 GORASP, GOLPH5 | MGLGVSAEQPAGGAEGFHLHGVQENSPAQQAGLEPY FDFIITIGHSRLNKENDTLKALLKANVEKPVKLEVFNMKT MRVREVEVVPSNMWGGQGLLGASVRFCSFRRASE (SEQ ID NO: 2) | 1428626 51316077 |
| KIAA1284 | PDZK6 | LNVYVNPKKLTVIKAKEQLKLLEVLVGIIHQTKWSWRRT GKQGDGERLVVHGLLPGGSAMKSGQVLIGDVLVAVND VDVTTENIERVLSCIPGPMQVKLTFENAYDVKRE (SEQ ID NO: 3) | 6331370 44888833 |

KIAA0313 was originally identified on the basis of its expression in human brain tissues. Since that time, it has been demonstrated to function as a guanine nucleotide exchange factor (GEF) for Rap1 and Rap2 GTPases (Rebhun et al, J. Biol. Chem. 275(45):34901-8 (2000); de Rooij et al, J. Biol. Chem. 274(53):38125-30 (1999)). KIAA0313 contains a single PDZ domain as well as a Ras associating domain and a Ras-GEF domain. It is highly expressed in the brain, but shows expression in the lung, kidney, heart and placenta.

Rap1 and 2 proteins are implicated in Ras signaling, and have been associated with leukocyte migration (Basoni, C et al., FASEB J. 2005 PMID:15746186), Leukocyte adhesion control (Etzioni, A et al., Curr Opin. Allergy Clin. Immunol. 2004 4(6):485-90) and activation of macrophage integrins in inflammation (Caron, E. et al., Curr. Biol. 2000, 10(16):974-8). These suggest a logical association with inflammatory responses such as asthma, and KIAA0313 is likely to regulate the complex formation between hCLCA1 and the Rap/Ras kinase pathways. Thus, blocking the interaction between calcium activated chloride channels and KIAA0313 will uncouple the kinase activation cascade and be useful in treating inflammatory disorders such as asthma, inhalation inflammation, and inflammation of the small intestine.

GRASP1 is a protein that is associated with organizing proteins in the stacking of golgi cisternae. It is also referred to GRASP65, GOLPH5 and GoRASP1. GRASP1 has been described as a stacking factor involved in the postmitotic assembly of Golgi stacks from mitotic Golgi fragments. It is a key structural protein required for the maintenance of the Golgi apparatus integrity: its caspase-mediated cleavage is required for fragmentation of the Golgi during apoptosis. One function is as an effector complex that links golgi structure to membrane traffic. It can also mediate, via its interaction with GM 130, the docking of transport vesicles with the Golgi membranes. It is generally present as a homodimer, and forms higher order oligomers under interphase but not mitotic conditions. Dimers of the protein on one membrane might be able to interact with dimers on another and so stack cisternae. GRASP1 interacts with the C-terminus of GM130 under both mitotic and non-mitotic conditions. The interaction is critical for the correct targeting of both proteins to the cis-Golgi. The complex binds to the vesicle docking protein p115 (By similarity). Localization of GRASP1 has been described in the golgi, as a peripheral membrane protein tightly associated with the cytoplasmic face of the membrane. Several alternatively spliced isoforms have been identified. GRASP1 can be phosphorylated by CDC2/B1 and PLK kinases during mitosis, and the phosphorylation cycle correlates with the cisternal stacking cycle. Phosphorylation of the homodimer prevents the association of dimers into higher order oligomers, leading to cisternal unstacking. GRASP1 is a target for caspase-3 cleavage during apoptosis. The cleavage contributes to Golgi fragmentation and occurs very early in the execution phase of apoptosis. One report has also demonstrated that GRASP1 is a target of polo-like kinase (Plk) and Cdc2, indicating a regulatory link to the cell cycle as well (Hort, B. et al. J. Cell Biol 155(4):557-70 (2001); Wang, Y et al., EMBO J. 22(13):3279-90 (2003); Lin, C et al. Proc. Natl. Acad. Sci. 97(23):12589-94 (2000)).

GRASP 1 is widely expressed, and expression in human lung is demonstrated by the expressed sequence tag (EST) 6571606. Disruption of the interaction between CLCA1 and GRASP could lead to the mislocalization of CLCA1 or inappropriate complex formation and thus disrupt CLCA1 function. This could be useful for the treatment of inflammatory diseases, disorders or responses including, but not limited to, asthma and airway hyperresponsiveness.

KIAA 1284 was identified as a protein expressed in brain. It is also called PDZK6 or PDZ domain containing protein 6. EST expression has demonstrated that KIAA 1284 is present in several tissues including ovary and endometrial tissues.

KIAA1284 interacts with hCLCA1, and disruption of this interaction could lead to a treatment for asthma or inflammation.

As discussed in detail herein, the PDZ proteins listed in TABLE 2 are naturally occurring proteins containing a PDZ domain. Thus, one aspect of the present invention is directed to the detection and modulation of interactions between a PDZ protein and PL protein pair listed in TABLE 3. As used herein the phrase "protein pair" or 'protein binding pair" when used in reference to a PDZ protein and PL protein refers to a PL protein and PDZ protein such as those listed in TABLE 3 which bind to one another. It should be understood that TABLE 3 is set up to show that certain PL proteins bind to a plurality of PDZ proteins.

The interactions like those summarized in TABLE 3 can occur in a wide variety of cell types. Examples of such cells include neuronal, hematopoietic, stem, muscle, epidermal, epithelial, endothelial, and cells from essentially any tissue such as liver, lung, placenta, uterus, kidney, ovaries, testes, stomach, colon and intestine. Because the interactions disclosed herein can occur in such a wide variety of cell types, these interactions can also play an important role in a variety of biological functions.

Thus, for example, in certain embodiments of the invention, the PL proteins and/or the PDZ protein to which it binds are expressed in the pulmonary system (e.g., in lung cells). In an embodiment, the PL proteins of the invention bind a PDZ protein that is expressed in lung cells. In various embodiments, the PL protein is highly expressed in lung cells. In still other instances the PL proteins and/or the PDZ protein to which it binds are expressed in non-pulmonary cells (e.g., in hematopoietic cells).

In various embodiments of the invention, the PL protein is expressed or up-regulated upon cell activation upon entry into mitosis (e.g., up-regulation in rapidly proliferating cell populations), or in association with cell death.

A. Detection of PDZ Domain-Containing Proteins

As noted supra, the present inventors have identified a number of PDZ protein and CACL1 PL protein interactions that can play a role in modulation of a number of biological functions in a variety of cell types. A comprehensive list of PDZ domain-containing proteins was retrieved from the Sanger Centre database (Pfam) searching for the keyword, "PDZ". The corresponding cDNA sequences were retrieved from GenBank using the NCBI "entrez" database (hereinafter, "GenBank PDZ protein cDNA sequences"). The DNA portion encoding PDZ domains was identified by alignment of cDNA and protein sequence using CLUSTALW. Based on the DNA/protein alignment information, primers encompassing the PDZ domains were designed. The expression of certain PDZ-containing proteins in cells was detected by polymerase chain reaction ("PCR") amplification of cDNAs obtained by reverse transcription ("RT") of cell-derived RNA (i.e., "RT-PCR"). PCR, RT-PCR and other methods for analysis and manipulation of nucleic acids are well known and are described generally in Sambrook et al., (1989) Molecular Cloning: A Laboratory Manual, 2nd Ed., Vols. 1-3, Cold Spring Harbor Laboratory hereinafter, "Sambrook"); and Ausubel et al., *Current Protocols in Molecular Biology*, Greene Publishing and Wiley-Interscience, New York (1997), as supplemented through January 1999 (hereinafter "Ausubel").

Samples of cDNA for those sequences identified through the foregoing search were obtained and then amplified. In general a sample of the cDNA (typically, ⅕ of a 20 µl reaction) was used to conduct PCR. PCR was conducted using primers designed to amplify specifically PDZ domain-containing regions of PDZ proteins of interest. Oligonucleotide primers were designed to amplify one or more PDZ-encoding domains. The DNA sequences encoding the various PDZ domains of interest were identified by inspection (i.e., conceptual translation of the PDZ protein cDNA sequences obtained from GenBank, followed by alignment with the PDZ domain amino acid sequence). TABLE 2 shows the PDZ-encoded domains amplified, and the GenBank accession number of the polynucleotides encoding the PDZ-domain containing proteins. To facilitate subsequent cloning of PDZ domains, the PCR primers included endonuclease restriction sequences at their ends to allow ligation with pGEX-3X cloning vector (Pharmacia, GenBank XXI13852) in frame with glutathione-S transferase (GST).

TABLE 2 lists the proteins isolated for use in the aforementioned assays.

B. Production of Fusion Proteins Containing PDZ-Domains

GST-PDZ domain fusion proteins were prepared for use in the assays of the invention. PCR products containing PDZ encoding domains (as described supra) were subcloned into an expression vector to permit expression of fusion proteins containing a PDZ domain and a heterologous domain (i.e., a glutathione-S transferase sequence, "GST"). PCR products (i.e., DNA fragments) representing PDZ domain encoding DNA was extracted from agarose gels using the "sephaglas" gel extraction system (Pharmacia) according to the manufacturer's recommendations.

As noted supra, PCR primers were designed to include endonuclease restriction sites to facilitate ligation of PCR fragments into a GST gene fusion vector (pGEX-3X; Pharmacia, GenBank accession # XXU13852) in-frame with the glutathione-S transferase coding sequence. This vector contains a IPTG inducible lacZ promoter. The pGEX-3× vector was linearized using Barn HI and Eco RI or, in some cases, Eco RI or Sma I, and dephosphorylated. For most cloning approaches, double digestion with Barn HI and Eco RI was performed, so that the ends of the PCR fragments to clone were Barn HI and Eco RI. In some cases, restriction endonuclease combinations used were Bgl II and Eco RI, Barn HI and Mfe I, or Eco RI only, Sma I only, or BamHI only. When more than one PDZ domain was cloned, the DNA portion cloned represents the PDZ domains and the cDNA portion located between individual domains. DNA linker sequences between the GST portion and the PDZ domain containing DNA portion vary slightly, dependent on which of the above described cloning sites and approaches were used. As a consequence, the amino acid sequence of the GST-PDZ fusion protein varies in the linker region between GST and PDZ domain. Protein linker sequences corresponding to different cloning sites/approaches are shown below. Linker sequences (vector DNA encoded) are bold, PDZ domain containing gene derived sequences are in italics.
1) GST-BamHI/BamHI-PDZ domain insert
   Gly-Ile-PDZ domain insert
GST-BamHI/BglII-PDZ domain insert
   Gly-Ile-PDZ domain insert
3) GST-EcoRI/EcoI-PDZ domain insert
   Gly-Ile-Pro-Gly-Asn-PDZ domain insert (SEQ ID NO:4)
4) GST-SmaI/SmaI-PDZ domain insert
   Gly-Ile-Pro-PDZ domain insert The PDZ-encoding PCR fragment and linearized pGEX-3× vector were ethanol precipitated and resuspended in 10 µl standard ligation buffer. Ligation was performed for 4-10 hours at 7° C. using T4 DNA ligase. It will be understood that some of the resulting constructs include very short linker sequences and that, when multiple PDZ domains were cloned, the constructs included some DNA located between individual PDZ domains.

The ligation products were transformed in DH5α or BL-21 *E. coli* bacteria strains. Colonies were screened for presence and identity of the cloned PDZ domain containing DNA as well as for correct fusion with the glutathione S-transferase encoding DNA portion by PCR and by sequence analysis. Positive clones were tested in a small scale assay for expression of the GST/PDZ domain fusion protein and, if expressing, these clones were subsequently grown up for large scale preparations of GST/PDZ fusion protein.

GST-PDZ domain fusion protein was overexpressed following addition of IPTG to the culture medium and purified. Detailed procedure of small scale and large scale fusion protein expression and purification are described in "GST Gene Fusion System" (second edition, revision 2; published by Pharmacia). In brief, a small culture (3-5 ml) containing a bacterial strain (DH5α, BL21 or JM109) with the fusion protein construct was grown overnight in LB-media at 37° C. with the appropriate antibiotic selection (100 µg/ml ampicillin; a.k.a. LB-amp). The overnight culture was poured into a fresh preparation of LB-amp (typically 250-500 ml) and grown until the optical density (OD) of the culture was between 0.5 and 0.9 (approximately 2.5 hours). IPTG (isopropyl β-D-thiogalactopyranoside) was added to a final concentration of 1.0 mM to induce production of GST fusion protein, and culture was grown an additional 1.5-2.5 hours. Bacteria were collect by centrifugation (4500 g) and resuspended in Buffer A– (50 mM Tris, pH 8.0, 50 mM dextrose, 1 mM EDTA, 200 µM phenylmethylsulfonylfluoride). An equal volume of Buffer A+ (Buffer A–, 4 mg/ml lysozyme) was added and incubated on ice for 3 min to lyse bacteria. An equal volume of Buffer B (10 mM Tris, pH 8.0, 50 mM KCl, 1 mM EDTA. 0.5% Tween-20, 0.5% NP40 (a.k.a. IGEPAL CA-630), 200 µM phenylmethylsulfonylfluoride) was added and incubated for an additional 20 minutes. The bacterial cell lysate was centrifuged (×20,000 g), and supernatant was added to glutathione SEPHAROSE 4B beads (Pharmacia, Cat. # 17-0765-01) previously swelled (rehydrated) in 1× phosphate-buffered saline (PBS). The supernatant-glutathione SEPHAROSE bead slurry was poured into a column and washed with at least 20 bed volumes of 1×PBS. GST fusion protein was eluted off the glutathione SEPHAROSE beads by applying 0.5-1.0 ml aliquots of 5 mM glutathione and collected as separate fractions. Concentrations of fractions were determined using BioRad Protein Assay (Cat. # 500-0006) according to manufacturer's specifications. Those fractions containing the highest concentration of fusion protein were pooled and dialyzed against 1×PBS/35% glycerol. Fusion proteins were assayed for size and quality by SDS gel electrophoresis (PAGE) as described in "Sambrook." Fusion protein aliquots were stored at minus 80° C. and at minus 20° C.

C. Assays for Detection of Interactions Between PDZ-Domain Polypeptides and TRP PL Proteins and TRP Associated Proteins Two complementary assays, termed A and G, were developed to detect binding between a PDZ-domain polypeptide and candidate PDZ ligand. In each of the two different assays, binding is detected between a peptide having a sequence corresponding to the C-terminus of a protein anticipated to bind to one or more PDZ domains (i.e. a candidate PL peptide) and a PDZ-domain polypeptide (typically a fusion protein containing a PDZ domain). In the A assay, the candidate PL peptide is immobilized and binding of a soluble PDZ-domain polypeptide to the immobilized peptide is detected (the A assay is named for the fact that in one embodiment an avidin surface is used to immobilize the peptide). In the G assay, the PDZ-domain polypeptide is immobilized and binding of a soluble PL peptide is detected (The G assay is named for the fact that in one embodiment a GST-binding surface is used to immobilize the PDZ-domain polypeptide). Preferred embodiments of these assays are described in detail infra. However, it will be appreciated by ordinarily skilled practitioners that these assays can be modified in numerous ways while remaining useful for the purposes of the present invention.

1) A Assay Detection of PDZ-Ligand Binding Using Immobilized PL Peptide.

In one aspect, the invention provides an assay in which biotinylated candidate PL peptides are immobilized on an avidin coated surface. The binding of PDZ-domain fusion protein to this surface is then measured. In a preferred embodiment, the PDZ-domain fusion protein is a GST/PDZ fusion protein and the assay is carried out as follows:

(1) Avidin is bound to a surface, e.g. a protein binding surface. In one embodiment, avidin is bound to a polystyrene 96 well plate (e.g., Nunc Polysorb (Cat. #475094) by addition of 100 µl per well of 20 µg/ml of avidin (Pierce) in phosphate buffered saline without calcium and magnesium, pH 7.4 ("PBS", GibcoBRL) at 4° C. for 12 hours. The plate is then treated to block nonspecific interactions by addition of 200 µl per well of PBS containing 2 g per 100 ml protease-free bovine serum albumin ("PBS/BSA") for 2 hours at 4° C. The plate is then washed 3 times with PBS by repeatedly adding 200 µl per well of PBS to each well of the, plate and then dumping the contents of the plate into a waste container and tapping the plate gently on a dry surface.

(2) Biotinylated PL peptides (or candidate PL peptides, e.g. see TABLE 2 and TABLE 4) are immobilized on the surface of wells of the plate by addition of 50 µA per well of 0.4 µM peptide in PBS/BSA for 30 minutes at 4° C. Usually, each different peptide is added to at least eight different wells so that multiple measurements (e.g. duplicates and also measurements using different (GST/PDZ-domain fusion proteins and a GST alone negative control) can be made, and also additional negative control wells are prepared in which no peptide is immobilized. Following immobilization of the PL peptide on the surface, the plate is washed 3 times with PBS.

(3) GST/PDZ-domain fusion protein (prepared as described supra) is allowed to react with the surface by addition of 50 µl per well of a solution containing 5 µg/ml GST/PDZ-domain fusion protein in PBS/BSA for 2 hours at 4° C. As a negative control, GST alone (i.e. not a fusion protein) is added to specified wells, generally at least 2 wells (i.e. duplicate measurements) for each immobilized peptide. After the 2 hour reaction, the plate is washed 3 times with PBS to remove unbound fusion protein.

(4) The binding of the GST/PDZ-domain fusion protein to the avidin-biotinylated peptide surface can be detected using a variety of methods, and detectors known in the art. In one embodiment, 50 µl per well of an anti-GST antibody in PBS/BSA (e.g. 2.5 µg/ml of polyclonal goat-anti-GST antibody, Pierce) is added to the plate and allowed to react for 20 minutes at 4° C. The plate is washed 3 times with PBS and a second, detectably labeled antibody is added. In one embodiment, 50 µl per well of 2.5 µg/ml of horseradish peroxidase (HRP)-conjugated polyclonal rabbit anti-goat immunoglobulin antibody is added to the plate and allowed to react for 20 minutes at 4° C. The plate is washed 5 times with 50 mM Tris pH 8.0 containing 0.2% Tween 20, and developed by addition of 100 µl per well of HRP-substrate solution (TMB, Dako) for 20 minutes at room temperature (RT). The reaction of the HRP and its substrate is terminated by the addition of 100 μl per well of 1 M sulfuric acid and the optical density (O.D.) of each well of the plate is read at 450 nm.

(5) Specific binding of a PL peptide and a PDZ-domain polypeptide is detected by comparing the signal from the well(s) in which the PL peptide and PDZ domain polypeptide are combined with the background signal(s). The background signal is the signal found in the negative controls. Typically a specific or selective reaction will be at least twice background signal, more typically more than 5 times background, and most typically 10 or more times the background signal. In addition, a statistically significant reaction will involve multiple measurements of the reaction with the signal and the background differing by at least two standard errors, more typically four standard errors, and most typically six or more standard errors. Correspondingly, a statistical test (e.g. a T-test) comparing repeated measurements of the signal with repeated measurements of the background will result in a p-value <0.05, more typically a p-value <0.01, and most typically a p-value <0.001 or less.

As noted, in an embodiment of the A assay, the signal from binding of a GST/PDZ-domain fusion protein to an avidin surface not exposed to (i.e. not covered with) the PL peptide is one suitable negative control (sometimes referred to as B1). The signal from binding of GST polypeptide alone (i.e. not a fusion protein) to an avidin-coated surface that has been exposed to (i.e. covered with) the PL peptide is a second suitable negative control (sometimes referred to as B2. Because all measurements are done in multiples (i.e. at least duplicate) the arithmetic mean (or, equivalently, average) of several measurements is used in determining the binding, and the standard error of the mean is used in determining the probable error in the measurement of the binding. The standard error of the mean of N measurements equals the square root of the following: the sum of the squares of the difference between each measurement and the mean, divided by the product of (N) and (N−1). Thus, in one embodiment, specific binding of the PDZ protein to the plate-bound PL peptide is determined by comparing the mean signal ("mean S") and standard error of the signal ("SE") for a particular PL-PDZ combination with the mean B1 and/or mean B2.

2) G Assay-Detection of PDZ-Ligand Binding Using Immobilized PDZ-Domain Fusion Polypeptide In one aspect, the invention provides an assay in which a GST/PDZ fusion protein is immobilized on a surface (G assay). The binding of labeled PL peptide (e.g., as listed in TABLE 3 and TABLE 5) to this surface is then measured. In a preferred embodiment, the assay is carried out as follows:
(1) A PDZ-domain polypeptide is bound to a surface, e.g. a protein binding surface. In a preferred embodiment, a GST/PDZ fusion protein containing one or more PDZ domains is bound to a polystyrene 96-well plate. The GST/PDZ fusion protein can be bound to the plate by any of a variety of standard methods known to one of skill in the art, although some care must be taken that the process of binding the fusion protein to the plate does not alter the ligand-binding properties of the PDZ domain. In one embodiment, the GST/PDZ fusion protein is bound via an anti-GST antibody that is coated onto the 96-well plate. Adequate binding to the plate can be achieved when:
a. 100 μl per well of 5 μg/ml goat anti-GST polyclonal antibody (Pierce) in PBS is added to a polystyrene 96-well plate (e.g., Nunc Polysorp) at 4° C. for 12 hours.
b. The plate is blocked by addition of 200 μl per well of PBS/BSA for 2 hours at 4° C.
c. The plate is washed 3 times with PBS.
d. 50 μl per well of 5 μg/ml GST/PDZ fusion protein) or, as a negative control, GST polypeptide alone (i.e. not a fusion protein) in PBS/BSA is added to the plate for 2 hours at 4° C.
e. the plate is again washed 3 times with PBS.
(2) Biotinylated PL peptides are allowed to react with the surface by addition of 50 μl per well of 20 μM solution of the biotinylated peptide in PBS/BSA for 10 minutes at 4° C., followed by an additional 20 minute incubation at 25° C. The plate is washed 3 times with ice cold PBS.
(3) The binding of the biotinylated peptide to the GST/PDZ fusion protein surface can be detected using a variety of methods and detectors known to one of skill in the art. In one embodiment, 100 μl per well of 0.5 μg/ml streptavidin-horseradish peroxidase (HRP) conjugate dissolved in BSA/PBS is added and allowed to react for 20 minutes at 4° C. The plate is then washed 5 times with 50 mM Tris pH 8.0 containing 0.2% Tween 20, and developed by addition of 100 μl per well of HRP-substrate solution (TMB, Dako) for 20 minutes at room temperature (RT). The reaction of the HRP and its substrate is terminated by addition of 100 μl per well of 1 M sulfuric acid, and the optical density (O.D.) of each well of the plate is read at 450 um.
(4) Specific binding of a PL peptide and a PDZ domain polypeptide is determined by comparing the signal from the well(s) in which the PL peptide and PDZ domain polypeptide are combined, with the background signal(s). The background signal is the signal found in the negative control(s). Typically a specific or selective reaction will be at least twice background signal, more typically more than 5 times background, and most typically 10 or more times the background signal. In addition, a statistically significant reaction will involve multiple measurements of the reaction with the signal and the background differing by at least two standard errors, more typically four standard errors, and most typically six or more standard errors. Correspondingly, a statistical test (e.g. a T-test) comparing repeated measurements of the signal with −repeated measurements of the background will result in a p-value <0.05, more typically a p-value <0.01, and most typically a p-value <0.001 or less. As noted, in an embodiment of the G assay, the signal from binding of a given PL peptide to immobilized (surface bound) GST polypeptide alone is one suitable negative control (sometimes referred to as B1). Because all measurement are done in multiples (i.e. at least duplicate) the arithmetic mean (or, equivalently, average.) of several measurements is used in determining the binding, and the standard error of the mean is used in determining the probable error in the measurement of the binding. The standard error of the mean of N measurements equals the square root of the following: the sum of the squares of the difference between each measurement and the mean, divided by the product of (N) and (N−1). Thus, in one embodiment, specific binding of the PDZ protein to the platebound peptide is determined by comparing the mean signal ("mean S") and standard error of the signal ("SE") for a particular PL-PDZ combination with the mean B1.

i) G1 assay, G2 assay, and G3 assay

Three specific modifications of the specific conditions described supra for the G assay are particularly useful. The modified assays use lesser quantities of labeled PL peptide and have slightly different biochemical requirements for detection of PDZ-ligand binding compared to the specific assay conditions described supra. For convenience, the assay conditions described in this section are referred to as the G1 assay, the G2 assay, and the G3 assay, with the specific conditions described in the preceding section on G assays being referred to as the G0 assay. The G1 assay is identical to the G0 assay except at step (2) the peptide concentration is 10 μM instead of 20 µM. This results in slightly lower sensitivity for detection of interactions with low affinity and/or rapid dissociation rate. Correspondingly, it slightly increases the certainty that detected interactions are of sufficient affinity and half-life to be of biological importance and useful therapeutic targets.

The G2 assay is identical to the G0 assay except that at step (2) the peptide concentration is 1 µM instead of 20 µM and the incubation is performed for 60 minutes at 25° C. (rather than, e.g., 10 minutes at 4° C. followed by 20 minutes at 25° C.). This results in lower sensitivity for interactions of low affinity, rapid dissociation rate, and/or affinity that is less at 25° C. than at 4° C. Interactions will have lower affinity at 25° C. than at 4° C. if (as we have found to be generally true for PDZ-ligand binding) the reaction entropy is negative (i.e. the entropy of the products is less than the entropy of the reactants). In contrast, the PDZ-PL binding signal may be similar in the G2 assay and the G0 assay for interactions of slow association and dissociation rate, as the PDZ-PL complex will accumulate during the longer incubation of the G2 assay. Thus comparison of results of the G2 assay and the G0 assay can be used to estimate the relative entropies, enthalpies, and kinetics of different PDZ-PL interactions. (Entropies and enthalpies are related to binding affinity by the equations delta G=RT ln (Kd)=delta H−T delta S where delta G, H, and S are the reaction free energy, enthalpy, and entropy respectively, T is the temperature in degrees Kelvin, R is the gas constant, and Kd is the equilibrium dissociation constant).

In particular, interactions that are detected only or much more strongly in the G0 assay generally have a rapid dissociation rate at 25° C. ($t_{1/2}$<10 minutes) and a negative reaction entropy, while interactions that are detected similarly strongly in the G2 assay generally have a slower dissociation rate at 25° C. ($t_{1/2}$>10 minutes). Rough estimation of the thermodynamics and kinetics of PDZ-PL interactions (as can be achieved via comparison of results of the G0 assay versus the G2 assay as outlined supra) can be used in the design of efficient inhibitors of the interactions. For example, a small molecule inhibitor based on the chemical structure of a PL that dissociates slowly from a given PDZ domain (as evidenced by similar binding in the G2 assay as in the G0 assay) may itself dissociate slowly and thus be of high affinity.

The G3 assay is identical to the G0 assay with the following exceptions. The peptides are typically present at 0.1 µM rather than 20 µM. The peptides are also pre-incubated with the HRP-streptavidin prior to adding to the assay plate. In the G0 assay, free peptide is incubated with the PDZ proteins prior to the addition of the HRP-streptavidin. Thus, for the G0 assay one can lose signal if the bound peptide dissociates from the PDZ protein prior to the addition of the HRP-streptavidin. In the G3 modified assay the HRP-streptavidin/peptide complex is added to the plate in one step, thus increasing the likelihood that all the bound peptide will be bound to HRP-streptavidin. The G3 modified assay increases the chance of observing weak interactions.

In this manner, variation of the temperature and duration of step (2) of the G assay can be used to provide insight into the kinetics and thermodynamics of the PDZ-ligand binding reaction and into design of inhibitors of the reaction.

With any of the assays, peptides should be titrated to find the optimal concentration for which the signal to noise ratio is in the appropriate range over the entire collection of PDZ domains tested.

3) Assay Variations

As discussed supra, it will be appreciated that many of the steps in the above-described assays can be varied, for example, various substrates can be used for binding the PL and PDZ-containing proteins; different types of PDZ containing fusion proteins can be used; different labels for detecting PDZ/PL interactions can be employed; and different ways of detection can be used.

The PL protein used in the assay is not intended to be limited to a 20 amino acid peptide. Full length or partial protein may be used, either alone or as a fusion protein. For example, a GST-PL protein fusion may be bound to the anti-GST antibody, with PDZ protein added to the bound PL protein or peptide.

The PDZ-PL detection assays can employ a variety of surfaces to bind the PL and PDZ-containing proteins. For example, a surface can be an "assay plate" which is formed from a material (e.g. polystyrene) which optimizes adherence of either the PL protein or PDZ-containing protein thereto. Generally, the individual wells of the assay plate will have a high surface area to volume ratio and therefore a suitable shape is a flat bottom well (where the proteins of the assays are adherent). Other surfaces include, but are not limited to, polystyrene or glass beads, polystyrene or glass slides, and the like.

For example, the assay plate can be a multiwell plate. The term multiwell plate when used herein refers to a multiwell assay plate, e.g., having between about 30 to 200 individual wells, usually 96 wells. Alternatively, high density arrays can be used. Often, the individual wells of the multiwell plate will hold a maximum volume of about 250 Conveniently, the assay plate is a 96 well polystyrene plate (such as that sold by Becton Dickinson Labware, Lincoln Park, N.J.), which allows for automation and high throughput screening. Other surfaces include polystyrene multiwell ELISA plates such as that sold by Nunc Maxisorp, Inter Med, Denmark. Often, about 50 µl to 300 µl, more preferably 100 µl to 200 µl of an aqueous sample comprising buffers suspended therein will be added to each well of the assay plate.

The detectable labels of the invention can be any detectable compound or composition which is conjugated directly or indirectly with a molecule (such as described above). The label can be detectable by itself (e.g., radioisotope labels or fluorescent labels) or, in the case of an enzymatic label, can catalyze a chemical alteration of a substrate compound or composition which is detectable. The preferred label is an enzymatic one which catalyzes a color change of a non-radioactive color reagent.

Sometimes, the label is indirectly conjugated with the antibody. One of skill is aware of various techniques for indirect conjugation. For example, the antibody can be conjugated with biotin and any of the categories of labels mentioned above can be conjugated with avidin, or vice versa (see also A and G assay above). Biotin binds selectively to avidin and thus, the label can be conjugated with the antibody in this indirect manner. See, Ausubel, supra, for a review of techniques involving biotin-avidin conjugation and similar assays. Alternatively, to achieve indirect conjugation of the label with the antibody, the antibody is conjugated with a small hapten (e.g. digoxin) and one of the different types of labels mentioned above is conjugated with an anti-hapten antibody (e.g. anti-digoxin antibody). Thus, indirect conjugation of the label with the antibody can be achieved.

Assay variations can include different washing steps. By "washing" is meant exposing the solid phase to an aqueous solution (usually a buffer or cell culture media) in such a way that unbound material (e.g., non-adhering cells, non-adhering capture agent, unbound ligand, receptor, receptor construct, cell lysate, or HRP antibody) is removed therefrom. To reduce background noise, it is convenient to include a detergent (e.g., Triton X) in the washing solution. Usually, the aqueous washing solution is decanted from the wells of the assay plate following washing. Conveniently, washing can be achieved using an automated washing device. Sometimes, several washing steps (e.g., between about 1 to 10 washing steps) can be required.

Various buffers can also be used in PDZ-PL detection assays. For example, various blocking buffers can be used to reduce assay background. The term "blocking buffer" refers to an aqueous, pH buffered solution containing at least one blocking compound which is able to bind to exposed surfaces of the substrate which are not coated with a PL or PDZ-containing protein. The blocking compound is normally a protein such as bovine serum albumin (BSA), gelatin, casein or milk powder and does not cross-react with any of the reagents in the assay. The block buffer is generally provided at a pH between about 7 to 7.5 and suitable buffering agents include phosphate and TRIS.

Various enzyme-substrate combinations can also be utilized in detecting PDZ-PL interactions. Examples of enzyme-substrate combinations include, for example:
(i) Horseradish peroxidase (HRPO) with hydrogen peroxidase as a substrate, wherein the hydrogen peroxidase oxidizes a dye precursor (e.g. orthophenylene diamine [OPD] or 3,3', 5,5'-tetramethyl benzidine hydrochloride [TMB]) (as described above).
(ii) alkaline phosphatase (AP) with para-Nitrophenyl phosphate as chromogenic substrate.
(iii) β-D-galactosidase (β D-Gal) with a chromogenic substrate (e.g. p-nitrophenyl-β-D-galactosidase) or fluorogenic substrate 4-methylumbelliferyl-B-D-galactosidase.

Numerous other enzyme-substrate combinations are available to those skilled in the art. For a general review of these, see U.S. Pat. Nos. 4,275,149 and 4,318,980, both of which are herein incorporated by reference.

Further, it will be appreciated that, although, for convenience, the present discussion primarily refers antagonists of PDZ-PL interactions, agonists of PDZ-PL interactions can be identified using the methods disclosed herein or readily apparent variations thereof.

E. Detecting PDZ-PL Interactions

The present inventors were able in part to identify the interactions summarized in TABLE 3 by developing new high throughput screening assays which are described supra. Various other assay formats known in the art can be used to select ligands that are specifically reactive with a particular protein. For example, solid-phase ELISA immunoassays, immuno-precipitation, Biacore, Fluorescence Polarization (FP), Fluorescence Resonance Energy Transfer (FRET) and western blot assays can be used to identify peptides that specifically bind PDZ-domain polypeptides. As discussed supra, two different, complementary assays were developed to detect PDZ-PL interactions. In each, one binding partner of a PDZ-PL pair is immobilized, and the ability of the second binding partner to bind is determined. These assays, which are described supra, can be readily used to screen for hundreds to thousands of potential PDZ-ligand interactions in a few hours. Thus these assays can be used to identify yet more novel PDZ-PL interactions in neuronal cells. In addition, they can be used to identify antagonists of PDZ-PL interactions (see infra).

In various embodiments, fusion proteins are used in the assays and devices of the invention. Methods for constructing and expressing fusion proteins are well known. Fusion proteins generally are described in Ausubel et al., supra, Kroll et al., 1993, DNA Cell. Biol. 12:441, and Imai et al., 1997, Cell 91:521-30. Usually, the fusion protein includes a domain to facilitate immobilization of the protein to a solid substrate ("an immobilization domain"). Often, the immobilization domain includes an epitope tag (i.e., a sequence recognized by a antibody, typically a monoclonal antibody) such as poly-histidine (Bush et al, 1991, *J. Biol Chem* 266:13811-14), SEAP (Berger et al, 1988, *Gene* 66:1-10), or M1 and M2 flag (see, e.g., U.S. Pat. Nos. 5,011,912; 4,851,341; 4,703,004; 4,782,137). In an embodiment, the immobilization domain is a GST coding region. It will be recognized that, in addition to the PDZ-domain and the particular residues bound by an immobilized antibody, protein A, or otherwise contacted with the surface, the protein (e.g., fusion protein), will contain additional residues. In some embodiments these are residues naturally associated with the PDZ-domain (i.e., in a particular PDZ-protein) but they may include residues of synthetic (e.g., poly(alanine)) or heterologous origin (e.g., spacers of, e.g., between 10 and 300 residues). PDZ domain-containing polypeptide used in the methods of the invention (e.g., PDZ fusion proteins) of the invention are typically made by (1) constructing a vector (e.g., plasmid, phage or phagemid) comprising a polynucleotide sequence encoding the desired polypeptide, (2) introducing the vector into an suitable expression system (e.g., a prokaryotic, insect, mammalian, or cell free expression system), (3) expressing the fusion protein and (4) optionally purifying the fusion protein.

In one embodiment, expression of the protein comprises inserting the coding sequence into an appropriate expression vector (i.e., a vector that contains the necessary elements for the transcription and translation of the inserted coding sequence required for the expression system employed, e.g., control elements including enhancers, promoters, transcription terminators, origins of replication, a suitable initiation codon (e.g., methionine), open reading frame, and translational regulatory signals (e.g., a ribosome binding site, a termination codon and a polyadenylation sequence. Depending on the vector system and host utilized, any number of suitable transcription and translation elements, including constitutive and inducible promoters, can be used.

The coding sequence of the fusion protein includes a PDZ domain and an immobilization domain as described elsewhere herein. Polynucleotides encoding the amino acid sequence for each domain can be obtained in a variety of ways known in the art; typically the polynucleotides are obtained by PCR amplification of cloned plasmids, cDNA libraries, and cDNA generated by reverse transcription of RNA, using primers designed based on sequences determined by the practitioner or, more often, publicly available (e.g., through GenBank). The primers include linker regions (e.g., sequences including restriction sites) to facilitate cloning and manipulation in production of the fusion construct. The polynucleotides corresponding to the PDZ and immobilization regions are joined in-frame to produce the fusion protein-encoding sequence.

The fusion proteins of the invention may be expressed as secreted proteins (e.g., by including the signal sequence encoding DNA in the fusion gene; see, e.g., Lui et al, 1993, *PNAS USA*, 90:8957-61) or as nonsecreted proteins.

In some embodiments, the PDZ-containing proteins are immobilized on a solid surface. The substrate to which the polypeptide is bound may in any of a variety of forms, e.g., a multiwell dish, a test tube, a dipstick, a microcentrifuge tube, a bead, a spinnable disk, and the like. Suitable materials include glass, plastic (e.g., polyethylene, PVC, polypropylene, polystyrene, and the like), protein, paper, carbohydrate, lipid monolayer or supported lipid bilayer, and other solid supports. Other materials that may be employed include ceramics, metals, metalloids, semiconductive materials, cements and the like.

In some embodiments, the fusion proteins are organized as an array. The term "array," as used herein, refers to an ordered arrangement of immobilized fusion proteins, in which particular different fusion proteins (i.e., having different PDZ domains) are located at different predetermined sites on the substrate. Because the location of particular fusion proteins on the array is known, binding at that location can be correlated with binding to the PDZ domain situated at that location. Immobilization of fusion proteins on beads (individually or in groups) is another particularly useful approach. In one embodiment, individual fusion proteins are immobilized on beads. In one embodiment, mixtures of distinguishable beads are used. Distinguishable beads are beads that can be separated from each other on the basis of a property such as size, magnetic property, color (e.g., using FACS) or affinity tag (e.g., a bead coated with protein A can be separated from a bead not coated with protein A by using IgG affinity methods). Binding to particular PDZ domain may be determined; similarly, the effect of test compounds (i.e., agonists and antagonists of binding) may be determined.

Methods for immobilizing proteins are known, and include covalent and non-covalent methods. One suitable immobilization method is antibody-mediated immobilization. According to this method, an antibody specific for the sequence of an "immobilization domain" of the PDZ-domain containing protein is itself immobilized on the substrate (e.g., by adsorption). One advantage of this approach is that a single antibody may be adhered to the substrate and used for immobilization of a number of polypeptides (sharing the same immobilization domain). For example, an immobilization domain consisting of poly-histidine (Bush et al, 1991, *J. Biol Chem* 266:13811-14) can be bound by an anti-histidine monoclonal antibody (R&D Systems, Minneapolis, Minn.); an immobilization domain consisting of secreted alkaline phosphatase ("SEAP") (Berger et al, 1988, *Gene* 66:1-10) can be bound by anti-SEAP (Sigma Chemical Company, St. Louis, Mo.); an immobilization domain consisting of a FLAG epitope can be bound by anti-FLAG. Other ligand-antiligand immobilization methods are also suitable (e.g., an immobilization domain consisting of protein A sequences (Harlow and Lane, 1988, Antibodies A Laboratory Manual, Cold Spring Harbor Laboratory; Sigma Chemical Co., St. Louis, Mo.) can be bound by IgG; and an immobilization domain consisting of streptavidin can be bound by biotin (Harlow & Lane, supra; Sigma Chemical Co., St. Louis, Mo.). In a preferred embodiment, the immobilization domain is a GST moiety, as described herein.

When antibody-mediated immobilization methods are used, glass and plastic are especially useful substrates. The substrates may be printed with a hydrophobic (e.g., Teflon) mask to form wells. Preprinted glass slides with 3, 10 and 21 wells per 14.5 cm² slide "working area" are available from, e.g., SPI Supplies, West Chester, Pa.; also see U.S. Pat. No. 4,011,350). In certain applications, a large format (12.4 cm×8.3 cm) glass slide is printed in a 96 well format is used; this format facilitates the use of automated liquid handling equipment and utilization of 96 well format plate readers of various types (fluorescent, colorimetric, scintillation). However, higher densities may be used (e.g., more than 10 or 100 polypeptides per cm²). See, e.g., MacBeath et al, 2000, *Science* 289:1760-63.

Typically, antibodies are bound to substrates (e.g., glass substrates) by adsorption. Suitable adsorption conditions are well known in the art and include incubation of 0.5-50 µg/ml (e.g., 10 µg/ml) mAb in buffer (e.g., PBS, or 50 to 300 mM Tris, MOPS, HEPES, PIPES, acetate buffers, pHs 6.5 to 8, at 4° C.) to 37° C. and from 1 hr to more than 24 hours. Proteins may be covalently bound or noncovalently attached through nonspecific bonding. If covalent bonding between the fusion protein and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature.

F. Measurement of PDZ-Ligand Binding Affinity

The A and G assays of the invention can be used to determine the "apparent affinity" of binding of a PDZ ligand peptide to a PDZ-domain polypeptide. Apparent affinity is determined based on the concentration of one molecule required to saturate the binding of a second molecule (e.g., the binding of a ligand to a receptor). Two particularly useful approaches for quantitation of apparent affinity of PDZ-ligand binding are provided infra.

Approach 1:

(1) A GST/PDZ fusion protein, as well as GST alone as a negative control, are bound to a surface (e.g., a 96-well plate) and the surface blocked and washed as described supra for the G assay.

(2) 50 µl per well of a solution of biotinylated PL peptide (e.g. as shown in TABLE 2) is added to the surface in increasing concentrations in PBS/BSA (e.g. at 0.1 µM, 0.33 µM, 1 µM, 3.3 µM, 10 µM, 33 µM, and 100 µM). In one embodiment, the PL peptide is allowed to react with the bound GST/PDZ fusion protein (as well as the GST alone negative control) for 10 minutes at 4° C. followed by 20 minutes at 25° C. The plate is washed 3 times with ice cold PBS to remove unbound labeled peptide.

(3) The binding of the PL peptide to the immobilized PDZ-domain polypeptide is detected as described supra for the G assay.

(4) For each concentration of peptide, the net binding signal is determined by subtracting the binding of the peptide to GST alone from the binding of the peptide to the GST/PDZ fusion protein. The net binding signal is then plotted as a function of ligand concentration and the plot is fit (e.g. by using the Kaleidagraph Synergy Software, Reading, Pa.) software package curve fitting algorithm) to the following equation, where "Signal$_{[ligand]}$" is the net binding signal at PL peptide concentration "[ligand]," "$K_d$" is the apparent affinity of the binding event, and "Saturation Binding" is a constant determined by the curve fitting algorithm to optimize the fit to the experimental data:

Signal$_{[ligand]}$=Saturation Binding×([ligand]/ ([ligand]+$K_d$))

For reliable application of the above equation it is necessary that the highest peptide ligand concentration successfully tested experimentally be greater than, or at least similar to, the calculated $K_d$ (equivalently, the maximum observed binding should be similar to the calculated saturation binding). In cases where satisfying the above criteria proves difficult, an alternative approach (infra) can be used.

Approach 2:

(1) A fixed concentration of a PDZ-domain polypeptide and increasing concentrations of a labeled PL peptide (labeled with, for example, biotin or fluorescein, see TABLE 2 and TABLE 4 for representative peptide amino acid sequences) are mixed together in solution and allowed to react. In one embodiment, preferred peptide concentrations are 0.1 µM, 1 µM, 10 µM, 100 µM, 1 mM. In various embodiments, appropriate reaction times can range from 10 minutes to 2 days at temperatures ranging from 4° C. to 37° C. In some embodiments, the identical reaction can also be carried out using a non-PDZ domain-containing protein as a control (e.g., if the PDZ-domain polypeptide is fusion protein, the fusion partner can be used).

2) PDZ-ligand complexes can be separated from unbound labeled peptide using a variety of methods known in the art. For example, the complexes can be separated using high performance size-exclusion chromatography (HPSEC, gel filtration) (Rabinowitz et al., 1998, Immunity 9:699), affinity chromatography (e.g. using glutathione SEPHAROSE beads), and affinity absorption (e.g., by binding to an anti-GST-coated plate as described supra).

(3) The PDZ-ligand complex is detected based on presence of the label on the peptide ligand using a variety of methods and detectors known to one of skill in the art. For example, if the label is fluorescein and the separation is achieved using HPSEC, an in-line fluorescence detector can be used. The binding can also be detected as described supra for the G assay.

(4) The PDZ-ligand binding signal is plotted as a function of ligand concentration and the plot is fit. (e.g., by using the Kaleidagraph software package curve fitting algorithm) to the following equation, where "Signal$_{[ligand]}$" is the binding signal at PL peptide concentration "[ligand]," "$K_d$" is the apparent affinity of the binding event, and "Saturation Binding" is a constant determined by the curve fitting algorithm to optimize the fit to the experimental data:

$$\text{Signal}_{[Ligand]} = \text{Saturation Binding} \times ([ligand]/([ligand]+K_d])$$

Measurement of the affinity of a labeled peptide ligand binding to a PDZ-domain polypeptide is useful because knowledge of the affinity (or apparent affinity) of this interaction allows rational design of inhibitors of the interaction with known potency. The potency of inhibitors in inhibition would be similar to (i.e. within one-order of magnitude of) the apparent affinity of the labeled peptide ligand binding to the PDZ-domain.

Thus, in one aspect, the invention provides a method of determining the apparent affinity of binding between a PDZ domain and a ligand by immobilizing a polypeptide comprising the PDZ domain and a non-PDZ domain on a surface, contacting the immobilized polypeptide with a plurality of different concentrations of the ligand, determining the amount of binding of the ligand to the immobilized polypeptide at each of the concentrations of ligand, and calculating the apparent affinity of the binding based on that data. Typically, the polypeptide comprising the PDZ domain and a non-PDZ domain is a fusion protein. In one embodiment, the e.g., fusion protein is GST-PDZ fusion protein, but other polypeptides can also be used (e.g., a fusion protein including a PDZ domain and any of a variety of epitope tags, biotinylation signals and the like) so long as the polypeptide can be immobilized in an orientation that does not abolish the ligand binding properties of the PDZ domain, e.g, by tethering the polypeptide to the surface via the non-PDZ domain via an anti-domain antibody and leaving the PDZ domain as the free end. It was discovered, for example, reacting a PDZ-GST fusion polypeptide directly to a plastic plate provided suboptimal results. The calculation of binding affinity itself can be determined using any suitable equation (e.g., as shown supra; also see Cantor and Schimmel (1980) Biophysical Chemistry WH Freeman & Co., San Francisco) or software.

Thus, in a preferred embodiment, the polypeptide is immobilized by binding the polypeptide to an immobilized immunoglobulin that binds the non-PDZ domain (e.g., an anti-GST antibody when a GST-PDZ fusion polypeptide is used). In a preferred embodiment, the step of contacting the ligand and PDZ-domain polypeptide is carried out under the conditions provided supra in the description of the G assay. It will be appreciated that binding assays are conveniently carried out in multiwell plates (e.g., 24-well, 96-well plates, or 384 well plates).

The present method has considerable advantages over other methods for measuring binding affinities PDZ-PL affinities, which typically involve contacting varying concentrations of a GST-PDZ fusion protein to a ligand-coated surface. For example, some previously described methods for determining affinity (e.g., using immobilized ligand and GST-PDZ protein in solution) did not account for oligomerization state of the fusion proteins used, resulting in potential errors of more than an order of magnitude.

Although not sufficient for quantitative measurement of PDZ-PL binding affinity, an estimate of the relative strength of binding of different PDZ-PL pairs can be made based on the absolute magnitude of the signals observed in the G assay. This estimate will reflect several factors, including biologically relevant aspects of the interaction, including the affinity and the dissociation rate. For comparisons of different ligands binding to a given PDZ domain-containing protein, differences in absolute binding signal likely relate primarily to the affinity and/or dissociation rate of the interactions of interest.

G. Assays to Identify Novel PDZ Domain Binding Moieties and to Identify Modulators of PDZ Protein-PL Protein Binding Although described supra primarily in terms of identifying interactions between PDZ-domain polypeptides and PL proteins, the assays described supra and other assays can also be used to identify the binding of other molecules (e.g., peptide mimetics, small molecules, and the like) to PDZ domain sequences. For example, using the assays disclosed herein, combinatorial and other libraries of compounds can be screened, e.g., for molecules that specifically bind to PDZ domains. Screening of libraries can be accomplished by any of a variety of commonly known methods. See, e.g., the following references, which disclose screening of peptide libraries: Parmley and Smith, 1989, Adv. Exp. Med. Biol. 251:215-218; Scott and Smith, 1990, Science 249:386-390; Fowlkes et al., 1992; BioTechniques 13:422-427; Oldenburg et al., 1992, Proc. Natl. Acad. Sci. USA 89:5393-5397; Yu et al., 1994, Cell 76:933-945; Staudt et al., 1988, Science 241: 577-580; Bock et al., 1992, Nature 355:564-566; Tuerk et al., 1992, Proc. Natl. Acad. Sci. USA 89:6988-6992; Ellington et al., 1992, Nature 355:850-852; U.S. Pat. No. 5,096,815, U.S. Pat. No. 5,223,409, and U.S. Pat. No. 5,198,346, all to Ladner et al.; Rebar and Pabo, 1993, Science 263:671-673; and PCT Publication No. WO 94/18318.

In a specific embodiment, screening can be carried out by contacting the library members with a PDZ-domain polypeptide immobilized on a solid support (e.g. as described supra in the G assay) and harvesting those library members that bind to the protein. Examples of such screening methods, termed "panning" techniques are described by way of example in Parmley and Smith, 1988, Gene 73:305-318; Fowlkes et al., 1992, BioTechniques 13:422-427; PCT Publication No. WO 94/18318; and in references cited hereinabove.

In another embodiment, the two-hybrid system for selecting interacting proteins in yeast (Fields and Song, 1989, Nature 340:245-246; Chien et al., 1991, Proc. Natl. Acad. Sci. USA 88:9578-9582) can be used to identify molecules that specifically bind to a PDZ domain-containing protein. Furthermore, the identified molecules are further tested for their ability to inhibit transmembrane receptor interactions with a PDZ domain.

In one aspect of the invention, antagonists of an interaction between a PDZ protein and a PL protein are identified. In one embodiment, a modification of the A assay described supra is used to identify antagonists. In one embodiment, a modification of the G assay described supra is used to identify antagonists.

In certain embodiments, screening assays are used to detect molecules that specifically bind to PDZ domains. Such molecules are useful as agonists or antagonists of PDZ-protein-mediated cell function (e.g., cell activation, e.g., T cell activation, vesicle transport, cytokine release, growth factors, transcriptional changes, cytoskeleton rearrangement, cell movement, chemotaxis, intercellular signaling, regulation of synaptic function, neuronal excitation, cytoskeletal integrity, and neurotransmitter release). In one embodiment, such assays are performed to screen for leukocyte activation inhibitors for drug development. The invention thus provides assays to detect molecules that specifically bind to PDZ domain-containing proteins. For example, recombinant cells expressing PDZ domain-encoding nucleic acids can be used to produce PDZ domains in these assays and to screen for molecules that bind to the domains. Molecules are contacted with the PDZ domain (or fragment thereof) under conditions conducive to binding, and then molecules that specifically bind to such domains are identified. Methods that can be used to carry out the foregoing are commonly known in the art.

Any of the compounds, modulators, inhibitors and compositions identified herein can be screened using the in vitro or in vivo methods (cellular or animal model). Natural products to be screened can be obtained from the National Cancer Institute's Natural Product Repository, Bethesda, Md. Known drugs for pulmonary diseases or other diseases can also be screened. Random libraries of peptides or other compounds can also be screened for suitability. Combinatorial libraries can be produced for many types of compounds that can be synthesized in a step-by-step fashion. Such compounds include polypeptides, beta-turn mimetics, polysaccharides, phospholipids, hormones, prostaglandins, steroids, aromatic compounds, heterocyclic compounds, benzodiazepines, oligomeric N-substituted glycines and oligocarbamates. Large combinatorial libraries of the compounds can be constructed by the encoded synthetic libraries (ESL) method described in Affymax, WO 95/12608, Affymax, WO 93/06121, Columbia University, WO 94/08051, Pharmacopeia, WO 95/35503 and Scripps, WO 95/30642 (each of which is incorporated herein by reference for all purposes). Peptide libraries can also be generated by phage display methods. See, e.g., Devlin, WO 91/18980. Combinatorial libraries and other compounds can initially be screened for suitability by determining their capacity to bind to PDZ or PL proteins.

It will be appreciated by the ordinarily skilled practitioner that, in one embodiment, antagonists are identified by conducting the A or G assays in the presence and absence of a known or candidate antagonist. When decreased binding is observed in the presence of a compound, that compound is identified as an antagonist. Increased binding in the presence of a compound signifies that the compound is an agonist.

For example, in one assay, a test compound can be identified as an inhibitor (antagonist) of binding between a PDZ protein and a PL protein by contacting a PDZ domain polypeptide and a PL peptide or protein in the presence and absence of the test compound, under conditions in which they would (but for the presence of the test compound) form a complex, and detecting the formation of the complex in the presence and absence of the test compound. It will be appreciated that less complex formation in the presence of the test compound than in the absence of the compound indicates that the test compound is an inhibitor of a PDZ protein—PL protein binding.

In one embodiment, the G assay is used in the presence or absence of an candidate inhibitor. In one embodiment, the A assay is used in the presence or absence of a candidate inhibitor.

In one embodiment (in which a G assay is used), one or more PDZ domain-containing GST-fusion proteins are bound to the surface of wells of a 96-well plate as described supra (with appropriate controls including nonfusion GST protein). All fusion proteins are bound in multiple wells so that appropriate controls and statistical analysis can be done. A test compound in BSA/PBS (typically at multiple different concentrations) is added to wells. Immediately thereafter, 30 µl of a detectably labeled (e.g., biotinylated) PL peptide or protein known to bind to the relevant PDZ domain (see, e.g., TABLE 3) is added in each of the wells at a final concentration of, e.g., between about 2 µM and about 40 µM, typically 5 µM, 15 µM, or 25 µM. This mixture is then allowed to react with the PDZ fusion protein bound to the surface for 10 minutes at 4° C. followed by 20 minutes at 25° C. The surface is washed free of unbound PL polypeptide three times with ice cold PBS and the amount of binding of the polypeptide in the presence and absence of the test compound is determined. Usually, the level of binding is measured for each set of replica wells (e.g. duplicates) by subtracting the mean GST alone background from the mean of the raw measurement of polypeptide binding in these wells.

In an alternative embodiment, the A assay is carried out in the presence or absence of a test candidate to identify inhibitors of PL-PDZ interactions.

If assays are conducted in the presence of test compound and compared against binding in the absence of test compound, then the assay can be conducted to determine if the difference between binding in the presence and absence of the test compound is a statistically significant difference.

In certain screening assays, assays are conducted to identify compounds that can inhibit a binding interaction between a CACL1 protein and a PDZ listed in TABLE 2. In other screening assays involve screening to identify an inhibitor that interferes with binding between CACL1 and a PDZ listed in TABLE 2.

In one embodiment, a test compound is determined to be a specific inhibitor of the binding of the PDZ domain (P) and a PL (L) sequence when, at a test compound concentration of less than or equal to 1 mM (e.g., less than or equal to: 500 µM, 100 µM, 10 µM, 1 µM, 100 µM or 1 µM) the binding of P to L in the presence of the test compound less than about 50% of the binding in the absence of the test compound (in various embodiments, less than about 25%, less than about 10%, or less than about 1%). Preferably, the net signal of binding of P to L in the presence of the test compound plus six (6) times the standard error of the signal in the presence of the test compound is less than the binding signal in the absence of the test compound.

In one embodiment, assays for an inhibitor are carried out using a single PDZ protein-PL protein pair (e.g., a PDZ domain fusion protein and a PL peptide or protein). In a related embodiment, the assays are carried out using a plurality of pairs, such as a plurality of different pairs listed in TABLES 3 or 5.

In some embodiments, it is desirable to identify compounds that, at a given concentration, inhibit the binding of one PL-PDZ pair, but do not inhibit (or inhibit to a lesser degree) the binding of a specified second PL-PDZ pair. These antagonists can be identified by carrying out a series of assays using a candidate inhibitor and different PL-PDZ pairs (e.g., as shown in TABLES 3 and 5) and comparing the results of the assays. All such pairwise combinations are contemplated by the invention (e.g., test compound inhibits binding of $PL_1$ to $PDZ_1$ to a greater degree than it inhibits binding of $PL_1$ to $PDZ_2$ or $PL_2$ to $PDZ_2$). Importantly, it will be appreciated that, based on the data provided in TABLES 3 and 5 and disclosed herein (and additional data that can be generated using the methods described herein) inhibitors with different specificities can readily be designed.

For example, according to the invention, the $K_i$ ("potency") of an inhibitor of a PDZ-PL interaction can be determined. $K_i$ is a measure of the concentration of an inhibitor required to have a biological effect. For example, administration of an inhibitor of a PDZ-PL interaction in an amount sufficient to result in an intracellular inhibitor concentration of at least between about 1 and about 100 $K_i$ is expected to inhibit the biological response mediated by the target PDZ-PL interaction. In one aspect of the invention, the $K_d$ measurement of PDZ-PL binding as determined using the methods supra is used in determining $K_i$.

Thus, in one aspect, the invention provides a method of determining the potency ($K_i$) of an inhibitor or suspected inhibitor of binding between a PDZ domain and a ligand by immobilizing a polypeptide comprising the PDZ domain and a non-PDZ domain on a surface, contacting the immobilized polypeptide with a plurality of different mixtures of the ligand and inhibitor, wherein the different mixtures comprise a fixed amount of ligand and different concentrations of the inhibitor, determining the amount of ligand bound at the different concentrations of inhibitor, and calculating the $K_i$ of the binding based on the amount of ligand bound in the presence of different concentrations of the inhibitor. In an embodiment, the polypeptide is immobilized by binding the polypeptide to an immobilized immunoglobulin that binds the non-PDZ domain. This method, which is based on the G assay described supra, is particularly suited for high-throughput analysis of the $K_i$ for inhibitors of PDZ-ligand interactions. Further, using this method, the inhibition of the PDZ-ligand interaction itself is measured, without distortion of measurements by avidity effects.

Typically, at least a portion of the ligand is detectably labeled to permit easy quantitation of ligand binding.

It will be appreciated that the concentration of ligand and concentrations of inhibitor are selected to allow meaningful detection of inhibition. Thus, the concentration of the ligand whose binding is to be blocked is close to or less than its binding affinity (e.g., preferably less than the $5 \times K_d$ of the interaction, more preferably less than $2 \times K_d$, most preferably less than $1 \times K_d$). Thus, the ligand is typically present at a concentration of less than $2 \times K_d$ (e.g., between about 0.01 $K_d$ and about 2 $K_d$) and the concentrations of the test inhibitor typically range from 1 nM to 100 µM (e.g. a 4-fold dilution series with highest concentration 10 µM or 1 mM). In a preferred embodiment, the $K_d$ is determined using the assay disclosed supra.

The $K_i$ of the binding can be calculated by any of a variety of methods routinely used in the art, based on the amount of ligand bound in the presence of different concentrations of the inhibitor. In an illustrative embodiment, for example, a plot of labeled ligand binding versus inhibitor concentration is fit to the equation:

$$S_{inhibitor} = S_0 * K_i / ([I] + K_i)$$

where $S_{inhibitor}$ is the signal of labeled ligand binding to immobilized PDZ domain in the presence of inhibitor at concentration [I] and $S_0$ is the signal in the absence of inhibitor (i.e., [I]=0). Typically [I] is expressed as a molar concentration.

In another aspect of the invention, an enhancer (sometimes referred to as, augmentor or agonist) of binding between a PDZ domain and a ligand is identified by immobilizing a polypeptide comprising the PDZ domain and a non-PDZ domain on a surface, contacting the immobilized polypeptide with the ligand in the presence of a test agent and determining the amount of ligand bound, and comparing the amount of ligand bound in the presence of the test agent with the amount of ligand bound by the polypeptide in the absence of the test agent. At least two-fold (often at least 5-fold) greater binding in the presence of the test agent compared to the absence of the test agent indicates that the test agent is an agent that enhances the binding of the PDZ domain to the ligand. As noted supra, agents that enhance PDZ-ligand interactions are useful for disruption (dysregulation) of biological events requiring normal PDZ-ligand function (e.g., cancer cell division and metastasis, and activation and migration of immune cells, intercellular communication, neurotransmitter release, membrane receptor turnover, second messenger signaling responsible for cell homeostasis and function).

The invention also provides methods for determining the "potency" or "$K_{enhancer}$" of an enhancer of a PDZ-ligand interaction. For example, according to the invention, the $K_{enhancer}$ of an enhancer of a PDZ-PL interaction can be determined, e.g., using the Kd of PDZ-PL binding as determined using the methods described supra. $K_{enhancer}$ is a measure of the concentration of an enhancer expected to have a biological effect. For example, administration of an enhancer of a PDZ-PL interaction in an amount sufficient to result in an intracellular inhibitor concentration of at least between about 0.1 and about 100 $K_{enhancer}$ (e.g., between about 0.5 and about 50 $K_{enhancer}$) is expected to disrupt the biological response mediated by the target PDZ-PL interaction.

Thus, in one aspect the invention provides a method of determining the potency ($K_{enhancer}$) of an enhancer or suspected enhancer of binding between a PDZ domain and a ligand by immobilizing a polypeptide comprising the PDZ domain and a non-PDZ domain on a surface, contacting the immobilized polypeptide with a plurality of different mixtures of the ligand and enhancer, wherein the different mixtures comprise a fixed amount of ligand, at least a portion of which is detectably labeled, and different concentrations of the enhancer, determining the amount of ligand bound at the different concentrations of enhancer, and calculating the potency ($K_{enhancer}$) of the enhancer from the binding based on the amount of ligand bound in the presence of different concentrations of the enhancer. Typically, at least a portion of the ligand is detectably labeled to permit easy quantitation of ligand binding. This method, which is based on the G assay described supra, is particularly suited for high-throughput analysis of the $K_{enhancer}$ for enhancers of PDZ-ligand interactions.

It will be appreciated that the concentration of ligand and concentrations of enhancer are selected to allow meaningful detection of enhanced binding. Thus, the ligand is typically present at a concentration of between about 0.01 $K_d$ and about 0.5 $K_d$ and the concentrations of the test agent/enhancer typically range from 1 nM to 1 mM (e.g. a 4-fold dilution series with highest concentration 10 µM or 1 mM). In a preferred embodiment, the $K_d$ is determined using the assay disclosed supra.

The potency of the binding can be determined by a variety of standard methods based on the amount of ligand bound in the presence of different concentrations of the enhancer or augmentor. For example, a plot of labeled ligand binding versus enhancer concentration can be fit to the equation:

$$S([E])=S(0)+(S(0)*(D_{enhancer}-1)*[E]/([E]+K_{enhancer})$$

where "$K_{enhancer}$" is the potency of the augmenting compound, and "$D_{enhancer}$" is the fold-increase in binding of the labeled ligand obtained with addition of saturating amounts of the enhancing compound, [E] is the concentration of the enhancer. It will be understood that saturating amounts are the amount of enhancer such that further addition does not significantly increase the binding signal. Knowledge of "$K_{enhancer}$" is useful because it describes a concentration of the augmenting compound in a target cell that will result in a biological effect due to dysregulation of the PDZ-PL interaction. Typical therapeutic concentrations are between about 0.1 and about 100 $K_{enhancer}$.

V. Determination of PDZ-PL Interaction Profiles

As described supra, the present invention provides powerful methods for analysis of PDZ-ligand interactions, including high-throughput methods such as the G assay and affinity assays described supra. In one embodiment of the invention, the affinity is determined for a particular ligand and a plurality of PDZ proteins. Typically the plurality is at least 5, and often at least 25, or at least 40 different PDZ proteins. In a preferred embodiment, the plurality of different PDZ proteins are from a particular tissue (e.g., central nervous system) or a particular class or type of cell, (e.g., a neuron) and the like. In a most preferred embodiment, the plurality of different PDZ proteins represents a substantial fraction (e.g., typically a majority, more often at least 80%) of all of the PDZ proteins known to be, or suspected of being, expressed in the tissue or cell(s), e.g., all of the PDZ proteins known to be present in lung cells. In an embodiment, the plurality is at least 50%, usually at least 80%, at least 90% or all of the PDZ proteins disclosed herein as being expressed in lung cells.

In one embodiment of the invention, the binding of a ligand to the plurality of PDZ proteins is determined. Using this method, it is possible to identify a particular PDZ domain bound with particular specificity by the ligand. The binding may be designated as "specific" if the affinity of the ligand to the particular PDZ domain is at least 2-fold that of the binding to other PDZ domains in the plurality (e.g., present in that cell type). The binding is deemed "very specific" if the affinity is at least 10-fold higher than to any other PDZ in the plurality or, alternatively, at least 10-fold higher than to at least 90%, more often 95% of the other PDZs in a defined plurality. Similarly, the binding is deemed "exceedingly specific" if it is at least 100-fold higher. For example, a ligand could bind to 2 different PDZs with an affinity of 1 µM and to no other PDZs out of a set 40 with an affinity of less than 100 µM. This would constitute specific binding to those 2 PDZs. Similar measures of specificity are used to describe binding of a PDZ to a plurality of PLs.

It will be recognized that high specificity PDZ-PL interactions represent potentially more valuable targets for achieving a desired biological effect. The ability of an inhibitor or enhancer to act with high specificity is often desirable. In particular, the most specific PDZ-ligand interactions are also the best therapeutic targets, allowing specific inhibition of the interaction.

Thus, in one embodiment, the invention provides a method of identifying a high specificity interaction between a particular PDZ domain and a ligand known or suspected of binding at least one PDZ domain, by providing a plurality of different immobilized polypeptides, each of said polypeptides comprising a PDZ domain and a non-PDZ domain; determining the affinity of the ligand for each of said polypeptides, and comparing the affinity of binding of the ligand to each of said polypeptides, wherein an interaction between the ligand and a particular PDZ domain is deemed to have high specificity when the ligand binds an immobilized polypeptide comprising the particular PDZ domain with at least 2-fold higher affinity than to immobilized polypeptides not comprising the particular PDZ domain.

In a related aspect, the affinity of binding of a specific PDZ domain to a plurality of ligands (or suspected ligands) is determined. For example, in one embodiment, the invention provides a method of identifying a high specificity interaction between a PDZ domain and a particular ligand known or suspected of binding at least one PDZ domain, by providing an immobilized polypeptide comprising the PDZ domain and a non-PDZ domain; determining the affinity of each of a plurality of ligands for the polypeptide, and comparing the affinity of binding of each of the ligands to the polypeptide, wherein an interaction between a particular ligand and the PDZ domain is deemed to have high specificity when the ligand binds an immobilized polypeptide comprising the PDZ domain with at least 2-fold higher affinity than other ligands tested. Thus, the binding may be designated as "specific" if the affinity of the PDZ to the particular PL is at least 2-fold that of the binding to other PLs in the plurality (e.g., present in that cell type). The binding is deemed "very specific" if the affinity is at least 10-fold higher than to any other PL in the plurality or, alternatively, at least 10-fold higher than to at least 90%, more often 95% of the other PLs in a defined plurality. Similarly, the binding is deemed "exceedingly specific" if it is at least 100-fold higher. Typically the plurality is at least 5 different ligands, more often at least 10.

1. Use of Array for Determination of PDZ-PL Interaction Profiles

One discovery of the present inventors relates to the important and extensive roles played by interactions between PDZ proteins and PL proteins, particularly in the biological function of neuronal cells. Further, it has been discovered that valuable information can be ascertained by analysis (e.g., simultaneous analysis) of a large number of PDZ-PL interactions. In a preferred embodiment, the analysis encompasses all of the PDZ proteins expressed in a particular tissue (e.g., brain) or type or class of cell (e.g., neuron). Alternatively, the analysis encompasses at least about 5, or at least about 10, or at least about 12, or at least about 15 and often at least 50 different polypeptides, up to about 60, about 80, about 100, about 150, about 200, or even more different polypeptides; or a substantial fraction (e.g., typically a majority, more often at least 80%) of all of the PDZ proteins known to be, or suspected of being, expressed in the tissue or cell(s), (e.g., all of the PDZ proteins known to be present in lungs).

It will be recognized that the arrays and methods of the invention are directed to analyze of PDZ and PL interactions, and involve selection of such proteins for analysis. While the devices and methods of the invention may include or involve a small number of control polypeptides, they typically do not include significant numbers of proteins or fusion proteins that do not include either PDZ or PL domains (e.g., typically, at least about 90% of the arrayed or immobilized polypeptides in a method or device of the invention is a PDZ or PL sequence protein, more often at least about 95%, or at least about 99%).

It will be apparent from this disclosure that analysis of the relatively large number of different interactions preferably takes place simultaneously. In this context, "simultaneously" means that the analysis of several different PDZ-PL interactions (or the effect of a test agent on such interactions) is assessed at the same time. Typically the analysis is carried out in a high throughput (e.g., robotic) fashion. One advantage of this method of simultaneous analysis is that it permits rigorous comparison of multiple different PDZ-PL interactions. For example, as explained in detail elsewhere herein, simultaneous analysis (and use of the arrays described infra) facilitates, for example, the direct comparison of the effect of an agent (e.g., a potential interaction inhibitor) on the interactions between a substantial portion of PDZs and/or PLs in a tissue or cell.

Accordingly, in one aspect, the invention provides an array of immobilized polypeptide comprising the PDZ domain and a non-PDZ domain on a surface. Typically, the array comprises at least about 5, or at least about 10, or at least about 12, or at least about 15 and often at least 50 different polypeptides. In one preferred embodiment, the different PDZ proteins are from a particular tissue (e.g., central nervous system) or a particular class or type of cell, (e.g., a neuron) and the like. In a more preferred embodiment, the plurality of different PDZ proteins represents a substantial fraction (e.g., typically a majority, more often at least 60%, 70% or 80%) of all of the PDZ proteins known to be, or suspected of being, expressed in the tissue or cell(s), (e.g., all of the PDZ proteins known to be present in lung).

Certain embodiments are arrays which include a plurality, usually at least 5, 10, 25, or 50 PDZ proteins present in a particular cell of interest. In this context, "array" refers to an ordered series of immobilized polypeptides in which the identity of each polypeptide is associated with its location. In some embodiments the plurality of polypeptides are arrayed in a "common" area such that they can be simultaneously exposed to a solution (e.g., containing a ligand or test agent). For example, the plurality of polypeptides can be on a slide, plate or similar surface, which may be plastic, glass, metal, silica, beads or other surface to which proteins can be immobilized. In a different embodiment, the different immobilized polypeptides are situated in separate areas, such as different wells of multi-well plate (e.g., a 24-well plate, a 96-well plate, a 384 well plate, and the like). It will be recognized that a similar advantage can be obtained by using multiple arrays in tandem.

2. Analysis of PDZ-PL Inhibition Profile

In one aspect, the invention provides a method for determining if a test compound inhibits any PDZ-ligand interaction in large set of PDZ-ligand interaction (e.g., a plurality of the PDZ-ligand interactions described in TABLE 3 and TABLE 5; a majority of the PDZ-ligands identified in a particular cell or tissue as described supra (e.g., lung) and the like. In one embodiment, the PDZ domains of interest are expressed as GST-PDZ fusion proteins and immobilized as described herein. For each PDZ domain, a labeled ligand that binds to the domain with a known affinity is identified as described herein.

For any known or suspected modulator (e.g., inhibitor) of a PDL-PL interaction(s), it is useful to know which interactions are inhibited (or augmented). For example, an agent that inhibits all PDZ-PL interactions in a cell (e.g., a lung cell) will have different uses than an agent that inhibits only one, or a small number, of specific PDZ-PL interactions. The profile of PDZ interactions inhibited by a particular agent is referred to as the "inhibition profile" for the agent, and is described in detail below. The profile of PDZ interactions enhanced by a particular agent is referred to as the "enhancement profile" for the agent. It will be readily apparent to one of skill guided by the description of the inhibition profile how to determine the enhancement profile for an agent. The present invention provides methods for determining the PDZ interaction (inhibition/enhancement) profile of an agent in a single assay.

In one aspect, the invention provides a method for determining the PDZ-PL inhibition profile of a compound by providing (i) a plurality of different immobilized polypeptides, each of said polypeptides comprising a PDZ domain and a non-PDZ domain and (ii) a plurality of corresponding ligands, wherein each ligand binds at least one PDZ domain in (i), then contacting each of said immobilized polypeptides in (i) with a corresponding ligand in (ii) in the presence and absence of a test compound, and determining for each polypeptide-ligand pair whether the test compound inhibits binding between the immobilized polypeptide and the corresponding ligand.

Typically the plurality is at least 5, and often at least 25, or at least 40 different PDZ proteins. In a preferred embodiment, the plurality of different ligands and the plurality of different PDZ proteins are from the same tissue or a particular class or type of cell, (e.g., a neuron). In a most preferred embodiment, the plurality of different PDZs represents a substantial fraction (e.g., at least 80%) of all of the PDZs known to be, or suspected of being, expressed in the tissue or cell(s), e.g., all of the PDZs known to be present in neurons (for example, at least 80%, at least 90% or all of the PDZs disclosed herein as being expressed in lung cells).

In one embodiment, the inhibition profile is determined as follows: A plurality (e.g., all known) PDZ domains expressed in a cell (e.g., lung cells) are expressed as GST-fusion proteins and immobilized without altering their ligand binding properties as described supra. For each PDZ domain, a labeled ligand that binds to this domain with a known affinity is identified. If the set of PDZ domains expressed in neurons is denoted by {P1 . . . Pn}, any given PDZ domain Pi binds a (labeled) ligand Li with affinity $K_di$. To determine the inhibition profile for a test agent "compound X" the G assay (supra) can be performed as follows in 96-well plates with rows A-H and columns 1-12. Column 1 is coated with P1 and washed. The corresponding ligand L1 is added to each washed coated well of column 1 at a concentration 0.5 $K_d1$ with (rows B, D, F, H) or without (rows A, C, E, F) between about 1 and about 1000 µM) of test compound X. Column 2 is coated with P2, and L2 (at a concentration 0.5 $K_d2$) is added with or without inhibitor X. Additional PDZ domains and ligands are similarly tested.

Compound X is considered to inhibit the binding of Li to Pi if the average signal in the wells of column i containing X is less than half the signal in the equivalent wells of the column lacking X. Thus, in this single assay one determines the full set of neural PDZs that are inhibited by compound X.

In some embodiments, the test compound X is a mixture of compounds, such as the product of a combinatorial chemistry synthesis as described supra. In some embodiments, the test compound is known to have a desired biological effect, and the assay is used to determine the mechanism of action (i.e., if the biological effect is due to modulating a PDZ-PL interaction).

It will be apparent that an agent that modulates only one, or a few PDZ-PL interactions, in a panel (e.g., a panel of all known PDZs in neurons, a panel of at least 10, at least 20 or at least 50 PDZ domains) is a more specific modulator than an agent that modulate many or most interactions. Typically, an agent that modulates less than 20% of PDZ domains in a panel is deemed a "specific" inhibitor, less than 6% a "very specific" inhibitor, and a single PDZ domain a "maximally specific" inhibitor.

It will be recognized that high specificity modulators of PDZ-PL interactions represent potentially more valuable drug targets for achieving a desired biological effect. The ability of an inhibitor or enhancer to act with "maximal specificity" is most desirable. In one embodiment, the assays of the invention can be used to determine a maximally specific modulator of the interaction between a CLCA channel and a PDZ domain.

In a preferred embodiment, the assays of the invention are used to identify a maximally specific modulator of the interaction between CLCA1 and a PDZ domain.

It will also be appreciated that "compound X" may be a composition containing mixture of compounds (e.g., generated using combinatorial chemistry methods) rather than a single compound.

Several variations of this assay are contemplated:

In some alternative embodiments, the assay above is performed using varying concentrations of the test compound X, rather than fixed concentration. This allows determination of the Ki of the X for each PDZ as described above. In an alternative embodiment, instead of pairing each PDZ Pi with a specific labeled ligand Li, a mixture of different labeled ligands is created that such that for every PDZ at least one of the ligands in the mixture binds to this PDZ sufficiently to detect the binding in the G assay. This mixture is then used for every PDZ domain.

In one embodiment, compound X is known to have a desired biological effect, but the chemical mechanism by which it has that effect is unknown. The assays of the invention can then be used to determine if compound X has its effect by binding to a PDZ domain.

In one embodiment, PDZ-domain containing proteins are classified in to groups based on their biological function, e.g. into those that regulate apoptosis versus those that regulate transcription. An optimal inhibitor of a particular function (e.g., including but not limited to an anti-apoptotic agent, an anti-T cell activation agent, cell-cycle control, vesicle transport, etc.) will inhibit multiple PDZ-ligand interactions involved in the function (e.g., apoptosis, activation) but few other interactions. Thus, the assay is used in one embodiment in screening and design of a drug that specifically blocks a particular function. For example, an agent designed to block apoptosis might be identified because, at a given concentration, the agent inhibits 2 or more PDZs involved in apoptosis but fewer than 3 other PDZs, or that inhibits PDZs involved in apoptosis with a $K_i$>10-fold better than for other PDZs. Thus, the invention provides a method for identifying an agent that inhibits a first selected PDZ-PL interaction or plurality of interactions but does not inhibit a second selected PDZ-PL interaction or plurality of interactions. The two (or more) sets of interactions can be selected on the basis of the known biological function of the PDZ proteins, the tissue specificity of the PDZ proteins, or any other criteria. Moreover, the assay can be used to determine effective doses (i.e., drug concentrations) that result in desired biological effects while avoiding undesirable effects.

3. Side Effects of PDZ-PL Modulator Interactions

In a related embodiment, the invention provides a method for determining likely side effects of a therapeutic that inhibits PDZ-ligand interactions. The method entails identifying those target tissues, organs or cell types that express PDZ proteins and ligands that are disrupted by a specified inhibitor. If, at a therapeutic dosage, a drug intended to have an effect in one organ system (e.g., pulmonary system) disrupts PDZ-PL interactions in a different system (e.g., hematopoietic system) it can be predicted that the drug will have effects ("side effects") on the second system. It will be apparent that the information obtained from this assay will be useful in the rational design and selection of drugs that do not have the side-effect.

In one embodiment, for example, a comprehensive PDZ protein set is obtained. A "perfectly comprehensive" PDZ protein set is defined as the set of all PDZ proteins expressed in the subject animal (e.g., humans). A comprehensive set may be obtained by analysis of, for example, the human genome sequence. However, a "perfectly comprehensive" set is not required and any reasonably large set of PDZ domain proteins (e.g., the set of all known PDZ proteins; or the set listed in TABLE 5) will provide valuable information.

In one embodiment, the method involves some of all of the following steps:

a) For each PDZ protein, determine the tissues in which it is highly expressed. This can be done experimentally although the information generally will be available in the scientific literature;

b) For each PDZ protein (or as many as possible), identify the cognate PL(s) bound by the PDZ protein;

c) Determine the $K_i$ at which the test agent inhibits each PDZ-PL interaction, using the methods described supra;

d) From this information it is possible to calculate the pattern of PDZ-PL interactions disrupted at various concentrations of the test agent.

By correlating the set of PDZ-PL interactions disrupted with the expression pattern of the members of that set, it will be possible to identify the tissues likely affected by the agent.

Additional steps can also be carried out, including determining whether a specified tissue or cell type is exposed to an agent following a particular route of administration. This can be determined using basis pharmacokinetic methods and principles.

4. Modulation of Activities

The PDZ binding moieties and inhibitors described herein that disrupt PDZ:PL protein interactions can be used to modulate biological activities or functions of cells (e.g., lung cells). These agents can also be utilized to treat diseases and conditions in human and nonhuman animals (e.g., experimental models).

When administered to patients, the compounds of the invention (e.g., PL-PDZ interaction inhibitors) are useful for treating (ameliorating symptoms of) a variety of pulmonary diseases including asthma, chronic obstructive pathway disease, including emphysema and chronic bronchitis, and disorders associated with improper mucus secretion.

VII. Screening and Testing Using Cell Based Assays and Animal Models

Any of the compounds and/or compositions herein or they can be tested for their ability to prevent, effect prophylaxis, ameliorate or treat symptoms associated with pulmonary diseases including asthma, chronic obstructive pathway disease, emphysema, chronic bronchitis, and disorders associated with improper mucus secretion. Preferably, the compounds and/or compositions can be tested for their ability to prevent, effect prophylaxis, ameliorate or treat symptoms associated with asthma. Cell-based systems can be useful for identifying agents that ameliorate symptoms associated with pulmonary diseases. Cell-based systems include cells that express one or more of the exhibit cellular phenotypes associated with pulmonary disorders, such as improper mucus secretion. Cell-based systems include recombinant transgenic cell lines derived from animal models of pulmonary diseases. Preferably, such cells provide a continuous cell line. Cell-based systems also include non-recombinant cell lines preferably from primary tissues of patients having pulmonary diseases. Controls can be included to identify a statistically significance difference between the compound being tested and the control in the absence of the compound.

A cell-based system having a phenotype of a pulmonary disease can be exposed to an agent identified as modulating the interaction between a CLCA protein and a PDZ protein as identified in the screening methods described herein. The cell-based system can be exposed to the compound and/or composition at a sufficient concentration and for a time sufficient to elicit such an amelioration response in the exposed cells. After exposure, the cells can be examined to determine whether the phenotypic states have been altered such that the phenotype has been eliminated and the cells resemble normal phenotypes.

Animal models can be used to further screen compounds identified to modulate the interaction between a CLCA protein and a PDZ protein to determine if the compounds act in vivo to prevent, ameliorate or treat symptoms associated with a pulmonary disease. The animal models can be used to determine toxicity, efficacy and/or mechanism of action of the compounds and/or compositions identified herein.

Many animal models have been developed as models of pulmonary diseases. Such models include mouse models of asthma and airway hyperresponsiveness, and mouse models of emphysema. Examples of such models include, the allergic mouse model of asthma (Wagers, et al. Journal of Applied Physiology 2004, June: 96(6): 2017-2018), the juvenile mouse model of asthma (Hamada, et al. Journal of Toxicology Environmental Health A. 1999 Oct. 15; 58(3):129-143), the Tbx minus mouse model (The Jackson Laboratory mouse database—JAX mice database, Bar Harbor, Me.), a mouse model of asthma and airway hyperresponsiveness (Singer et al. Nat. Med. 2004 February; 10(2):193-6), a mouse model of airway remodeling, (Shinagawa, et al, Am. J. Respir. Crit. Care Medicine 2003 Oct. 15; 168(8):910-1), a mouse model of emphysema (Ito, et al. J. Appl. Physiol. 2005 February; 98(2):503-511. Non-recombinant animal models for pulmonary diseases may also be used.

Any of the animal models disclosed herein can be used to further screen compounds identified as modulating the interaction between a CLCA protein and a PDZ protein. Further, the animal models can be used to identify agents capable of ameliorating, treating or preventing symptoms associated with pulmonary diseases. For example, animal models can be exposed to a compound suspected of exhibiting an ability to ameliorate one or more symptoms associated with pulmonary disease at a sufficient concentration and for a time sufficient to elicit an ameliorating response in the exposed animal. The response of the exposed animal can be monitored by assessing change in symptoms. Any treatments that diminish one or more symptoms associated with pulmonary disease or susceptibility thereto may be considered a candidate for human therapy. Dosages of test agents can be determined by deriving dose-response curves, which are well-known and commonly used in the art. Routes of administration can be any routes commonly used, e.g. intravenous, intramuscular, subcutaneous, or those routes that directly administer the compounds or compositions to the lungs and or respiratory tract.

VIII. Antagonists of PDZ-PL Interactions

As described herein, interactions between PDZ proteins and PL proteins in cells (e.g., lung cells) may be disrupted or inhibited by the administration of inhibitors or antagonists. Inhibitors can be identified using screening assays described herein. In embodiment, the motifs disclosed herein are used to design inhibitors.

The PDZ/PL antagonists and antagonists of the invention can be any of a large variety of compounds, both naturally occurring and synthetic, organic and inorganic, and including polymers (e.g., oligopeptides, polypeptides, oligonucleotides, and polynucleotides), small molecules, antibodies, sugars, fatty acids, nucleotides and nucleotide analogs, analogs of naturally occurring structures (e.g., peptide mimetics, nucleic acid analogs, and the like), and numerous other compounds. Although, for convenience, the present discussion primarily refers antagonists of PDZ-PL interactions, it will be recognized that PDZ-PL interaction agonists can also be use in the methods disclosed herein.

In one aspect, the peptides and peptide mimetics or analogues of the invention contain an amino acid sequence that binds a PDZ domain in a cell of interest. In one embodiment, the antagonists comprise a peptide that has a sequence corresponding to the carboxy-terminal sequence of a PL protein listed in TABLE 3 or TABLE 5 or 6. Typically, the peptide comprises at least the C-terminal two (3), three (3) or four (4) residues of the PL protein, and often the inhibitory peptide comprises more than four residues (e.g., at least five, six, seven, eight, nine, ten, twelve or fifteen residues) from the PL protein C-terminus.

In some embodiments, the inhibitor is a peptide, e.g., having a sequence of a PL C-terminal protein sequence.

In some embodiments, the antagonist is a fusion protein comprising such a sequence. Fusion proteins containing a transmembrane transporter amino acid sequence can be used to facilitate transport of the inhibitor into a cell.

In some embodiments, the inhibitor is conserved variant of the PL C-terminal protein sequence having inhibitory activity.

In some embodiments, the antagonist is a peptide mimetic of a PL C-terminal sequence.

In some embodiments, the inhibitor is a small molecule (i.e., having a molecular weight less than 1 kDa).

A. Polypeptide Antagonists

1. Inhibitors with a PL Sequence

One class of inhibitors or antagonists that are provided comprise a peptide that has a sequence of a PL protein carboxy-terminus listed in TABLE 4. The PL protein carboxy-terminus sequences can be considered as the "core PDZ motif sequence" because of the ability of the short sequence from the carboxy terminus to interact with the PDZ domain. For example, in some inhibitors the "core PDZ motif sequence" or simply the "PL sequence" contains the last 2, 3 or 4 C-terminus amino acids. In other instances, however, the core PDZ motif comprises more than 2-4 residues (e.g., at least 5, 6, 7, 8, 9, 10, 11, 12, 13, 14, 15, 16, 17, 18, 19, or 20 residues) from the PL protein C-terminus. For some inhibitors, the PDZ motif sequence peptide is from 4-15 amino acids in length. Other inhibitors have a PDZ motif sequence that is 6-10 amino acids in length, or 3-8 amino acids in length, or 3-7 amino acids in length. Certain inhibitors have a PDZ motif sequence that is 8 amino acids in length. Although the residues shared by the inhibitory peptide and the PL protein are often found at the C-terminus of the peptide, some inhibitors incorporate a PL sequence that is located in an internal region of a PL protein. Similarly, in some cases, the inhibitory peptide comprises residues from a PL sequence that is near, but not at the C-terminus of a PL protein (see, Gee et al., 1998, J. Biol. Chem. 273:21980-87).

These specific examples should not be considered as limiting but simply illustrative of inhibitors having the general characteristics listed above.

As described in greater detail below, short PL peptides, such as just described, can be used in the rational design of other small molecules with similar properties according to established techniques.

Core PDZ motif sequences/PL sequences such as those just listed can optionally be joined to additional amino acids at their amino terminus to further increase binding affinity and/or stability and/or transportability into cells. These additional sequences located at the amino terminus can be from the natural sequence of a neuronal cell surface receptor or from other sources. The PDZ motif sequence and additional N-terminal sequences can optionally be joined by a linker. The additional amino acids can also be conservatively substituted. The total peptide length (i.e., core PDZ motif sequence plus optional N-terminal segment) can be of a variety of lengths (e.g., at least 2, 3, 4, 5, 6, 8, 10, 15, 20, 25, 30, 40, 50, 60, 70, 80, 90, 100 or more amino acids). Typically, the overall length is in the range of 30-40 amino acids) For those inhibitors in which additional sequences are attached at the N-terminus of the core PDZ motif sequence (PL sequence), the overall structure is thus: N-terminal segment-core PDZ motif sequence (PL sequence), or N-terminal segment-linker-core PDZ motif sequence (PL sequence). As discussed further below, one useful class of proteins that can be fused to the core PDZ motifs or PL sequences are transmembrane transporter peptides. These peptides can be fused to the inhibitory sequences to facilitate transport into a target cell (e.g., neuron). Further details are provided below. Purification tags that are known in the art can also optionally be fused to the N-terminus of the PL sequence.

2. Inhibitors with a PDZ-Domain Polypeptide

Some of the inhibitors that are provided contain all or a portion of a PDZ binding domain rather than containing a PL sequence. The PDZ-domain sequence included in these inhibitors is selected to mimic (i.e., have similar binding characteristics) of the PDZ domain in the PDZ protein of interest (i.e., the PDZ protein whose binding interaction with a PL protein one seeks to disrupt). The PDZ-domain sequence is long enough to include at least enough of the PDZ domain such that the resulting polypeptide inhibitor can effectively bind to the cognate PL protein. This typically means that the PDZ-domain sequence is at least 50, 55, 60, 65, 70, 75, 80, 85, 90 or more amino acids long. But certain inhibitors can include the entire PDZ-domain, or even additional amino acids from the PDZ protein that extend beyond the PDZ-domain.

3. Optional Features of Inhibitors

Polypeptide inhibitors such as those just described can optionally be derivatized (e.g., acetylated, phosphorylated and/or glycoslylated) to improve the binding affinity of the inhibitor, to improve the ability of the inhibitor to be transported across a cell membrane or to improve stability. As a specific example, for inhibitors in which the third residue from the C-terminus is S, T or Y, this residue can be phosphorylated prior to the use of the peptide. The polypeptide inhibitors can also optionally be linked directly or via a linker to a transmembrane transporter peptide. Specific examples of these sequences are described in the section on formulation and administration of the polypeptides of the invention. Certain polypeptide inhibitors, however, do not include a transporter peptide.

B. Peptide Variants

Having identified PDZ binding peptides and PDZ-PL interaction inhibitory sequences, variations of these sequences can be made and the resulting peptide variants can be tested for PDZ domain binding or PDZ-PL inhibitory activity. In embodiments, the variants have the same or a different ability to bind a PDZ domain as the parent peptide. Typically, such amino acid substitutions are conservative, i.e., the amino acid residues are replaced with other amino acid residues having physical and/or chemical properties similar to the residues they are replacing. Preferably, conservative amino acid substitutions are those wherein an amino acid is replaced with another amino acid encompassed within the same designated class.

C. Peptide Mimetics

Having identified PDZ binding peptides and PDZ-PL interaction inhibitory sequences, peptide mimetics can be prepared using routine methods, and the inhibitory activity of the mimetics can be confirmed using the assays of the invention. Thus, in some embodiments, the antagonist is a peptide mimetic of a PL C-terminal sequence. The skilled artisan will recognize that individual synthetic residues and polypeptides incorporating mimetics can be synthesized using a variety of procedures and methodologies, which are well described in the scientific and patent literature, e.g., *Organic Syntheses Collective Volumes*, Gilman et al. (Eds) John Wiley & Sons, Inc., NY. Polypeptides incorporating mimetics can also be made using solid phase synthetic procedures, as described, e.g., by Di Marchi, et al., U.S. Pat. No. 5,422,426. Mimetics of the invention can also be synthesized using combinatorial methodologies. Various techniques for generation of peptide and peptidomimetic libraries are well known, and include, e.g., multipin, tea bag, and split-couple-mix techniques; see, e.g., al-Obeidi (1998) Mol. Biotechnol. 9:205-223; Hruby (1997) Curr. Opin. Chem. Biol. 1:114-119; Ostergaard (1997) Mol. Divers. 3:17-27; Ostresh (1996) Methods Enzymol. 267:220-234.

D. Small Molecules

In some embodiments, the inhibitor is a small molecule (i.e., having a molecular weight less than 1 kDa). Methods for screening small molecules are well known in the art and include those described supra.

E. Binding Affinity

Regardless of type, the inhibitors generally have an $EC_{50}$ of less than 50 μm. Some inhibitors have an $EC_{50}$ of less than 10 μM, others have an $EC_{50}$ of 1 μM, and still others an $EC_{50}$ of less than 100 nM. The inhibitors typically have an $EC_{50}$ value of 20-100 nM.\

IX. Uses of PDZ Domain Binding and Antagonist Compounds

Because the inhibitors that are described herein are useful in interfering with binding between certain PDZ and PL proteins in lung cells (e.g., the CLCA1/PDZ interaction), the inhibitors can be utilized in the treatment of a variety of biological processes in lung cells. For instance, the inhibitors can be utilized to various pulmonary diseases including pulmonary diseases including asthma, chronic obstructive pathway disease, including emphysema and chronic bronchitis, and disorders associated with improper mucus secretion.

Because PDZ proteins are involved in a number of biological functions besides involvement in excitotoxicity responses, some of the inhibitors that are provided can be used in the treatment of other conditions and activities correlated with the PDZ:PL protein interactions described herein. Examples of such activities include, but are not limited to, organization and regulation of multiprotein complexes, vesicular trafficking, tumor suppression, protein sorting, establishment of membrane polarity, apoptosis, regulation of immune response and organization of synapse formation. In general, PDZ proteins have a common function of facilitating the assembly of multi-protein complexes, often serving as a bridge between several proteins, or regulating the function of other proteins. Additionally, as also noted supra, these proteins are found in essentially all cell types.

X. Formulation and Route of Administration

A. Introduction of Antagonists (e.g., Peptides and Fusion Proteins) into Cells

The inhibitors disclosed herein or identified using the screening methods that are provided can be used in the manufacture of a medicament or pharmaceutical composition. These can then be administered according to a number of different methods.

In one aspect, the PDZ-PL antagonists of the invention are introduced into a cell to modulate (i.e., increase or decrease) a biological function or activity of the cell. Many small organic molecules readily cross the cell membranes (or can be modified by one of skill using routine methods to increase the ability of compounds to enter cells, e.g., by reducing or eliminating charge, increasing lipophilicity, conjugating the molecule to a moiety targeting a cell surface receptor such that after interacting with the receptor). Methods for introducing larger molecules, e.g., peptides and fusion proteins are also well known, including, e.g., injection, liposome-mediated fusion, application of a hydrogel, conjugation to a targeting moiety conjugate endocytozed by the cell, electroporation, and the like).

In one embodiment, the antagonist or agent is a fusion polypeptide or derivatized polypeptide. A fusion or derivatized protein may include a targeting moiety that increases the ability of the polypeptide to traverse a cell membrane or causes the polypeptide to be delivered to a specified cell type (e.g., a neuron) preferentially or cell compartment (e.g., nuclear compartment) preferentially. Examples of targeting moieties include lipid tails, amino acid sequences such as antennapoedia peptide or a nuclear localization signal (NLS; e.g., *Xenopus* nucleoplasmin Robbins et al., 1991, *Cell* 64:615).

In one embodiment of the invention, a peptide sequence or peptide analog determined to inhibit a PDZ domain-PL protein binding interaction as described herein is introduced into a cell by linking the sequence to an amino acid sequence that facilitates its transport through the plasma membrane (a "transmembrane transporter sequence"). The peptides of the invention may be used directly or fused to a transmembrane transporter sequence to facilitate their entry into cells. In the case of such a fusion peptide, each peptide may be fused with a heterologous peptide at its amino terminus directly or by using a flexible polylinker such as the pentamer G-G-G-G-S (SEQ ID NO:5) repeated 1 to 3 times. Such linker has been used in constructing single chain antibodies (scFv) by being inserted between $V_H$ and $V_L$ (Bird et al., 1988, *Science* 242: 423-426; Huston et al., 1988, *Proc. Natl. Acad. Sci. U.S.A.* 85:5979-5883). The linker is designed to enable the correct interaction between two beta-sheets forming the variable region of the single chain antibody. Other linkers which may be used include Glu-Gly-Lys-Ser-Ser-Gly-Ser-Gly-Ser-Glu-Ser-Lys-Val-Asp (SEQ ID NO:6) (Chaudhary et al., 1990, *Proc. Natl. Acad. Sci. U.S.A.* 87:1066-1070) and Lys-Glu-Ser-Gly-Ser-Val-Ser-Ser-Glu-Gln-Leu-Ala-Gln-Phe-Arg-Ser-Leu-Asp (SEQ ID NO:7) (Bird et al., 1988, *Science* 242: 423-426).

A number of peptide sequences have been described in the art as capable of facilitating the entry of a peptide linked to these sequences into a cell through the plasma membrane (Derossi et al., 1998, *Trends in Cell Biol.* 8:84). For the purpose of this invention, such peptides are collectively referred to as transmembrane transporter peptides. Examples of these peptides include, but are not limited to, tat derived from HIV (Vives et al., 1997, *J. Biol. Chem.* 272:16010; Nagahara et al., 1998, *Nat. Med.* 4:1449), antennapedia from *Drosophila* (Derossi et al., 1994, *J. Biol. Chem.* 261:10444), VP22 from herpes simplex virus (Elliot and D'Hare, 1997, *Cell* 88:223-233), complementarity-determining regions (CDR) 2 and 3 of anti-DNA antibodies (Avrameas et al., 1998, *Proc. Natl. Acad. Sci. U.S.A.,* 95:5601-5606), 70 kDa heat shock protein (Fujihara, 1999, *EMBO J.* 18:411-419), transportan (Pooga et al., 1998, *FASEB J.* 12:67-77), penetratin, SynB1, SynB3, amphipathic model peptide, signal sequence-based peptides, and Arg, as described in Temsamani et al. (2004) *Drug Discovery Today* 9:1012-1019. In a preferred embodiment of the invention, a truncated HIV tat peptide having the sequence of YGRKKRRQRRR (SEQ ID NO:8) is used.

In some instances, a transmembrane transporter sequence is fused to a CLCA1 carboxyl terminal sequence at its aminoterminus with or without a linker. Generally, the C-terminus of a PDZ motif sequence (PL sequence) is free to interact with a PDZ domain. The transmembrane transporter sequence can be used in whole or in part as long as it is capable of facilitating entry of the peptide into a cell.

In an alternate embodiment of the invention, a CLCA1 C-terminal sequence can be used alone when it is delivered in a manner that allows its entry into cells in the absence of a transmembrane transporter sequence. For example, the peptide may be delivered in a liposome formulation or using a gene therapy approach by delivering a coding sequence for the PDZ motif alone or as a fusion molecule into a target cell.

The compounds of the invention can also be administered via liposomes, which serve to target the conjugates to a particular tissue, such as neural tissue, or targeted selectively to infected cells, as well as increase the half-life of the peptide composition.

Liposomes include emulsions, foams, micelles, insoluble monolayers, liquid crystals, phospholipid dispersions, lamellar layers and the like. In these preparations, the peptide to be delivered is incorporated as part of a liposome, alone or in conjunction with a molecule which binds to, e.g., a receptor prevalent among neural cells, such as monoclonal antibodies which bind to the NMDA Receptor. Thus, liposomes filled with a desired peptide or conjugate of the invention can be directed to the site of neural cells, where the liposomes then deliver the selected inhibitor compositions. Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al., Ann. Rev. Biophys. Bioeng. 9:467 (1980), U.S. Pat. Nos. 4,235, 871, 4,501,728 and 4,837,028.

The targeting of liposomes using a variety of targeting agents is well known in the art (see, e.g., U.S. Pat. Nos. 4,957,773 and 4,603,044). For targeting to the neural cells, a ligand to be incorporated into the liposome can include, e.g., antibodies or fragments thereof specific for cell surface determinants of the desired nervous system cells. A liposome suspension containing a peptide or conjugate may be administered intravenously, locally, topically, etc. in a dose which varies according to, inter alia, the manner of administration, the conjugate being delivered, and the stage of the disease being treated.

In another approach, microspheres of artificial polymers of mixed amino acids (proteinoids) have been used to deliver pharmaceuticals. For example, U.S. Pat. No. 4,925,673 describes drug-containing proteinoid microsphere carriers as well as methods for their preparation and use. These proteinoid microspheres are useful for the delivery of a number of active agents. Also see, U.S. Pat. Nos. 5,907,030 and 6,033,884, which are incorporated herein by reference.

B. Introduction of Polynucleotides into Cells

By introducing gene sequences into cells, gene therapy can be used to treat diseased cells. In one embodiment, a polynucleotide that encodes a PL sequence peptide of the invention is introduced into a cell where it is expressed. The expressed peptide then inhibits the interaction of PDZ proteins and PL proteins in the cell. In another embodiment, the expression of a given protein would be suppressed, thus inhibiting its interactions with other proteins.

In one embodiment, the polypeptides of the invention are expressed in a cell by introducing a nucleic acid (e.g., a DNA expression vector or mRNA) encoding the desired protein or peptide into the cell. Expression can be either constitutive or inducible depending on the vector and choice of promoter. Methods for introduction and expression of nucleic acids into a cell are well known in the art and described herein.

In a specific embodiment, nucleic acids comprising a sequence encoding a peptide disclosed herein, are administered to a human subject. In this embodiment of the invention, the nucleic acid produces its encoded product that mediates a therapeutic effect. Any of the methods for gene therapy available in the art can be used according to the present invention. Exemplary methods are described below.

For general reviews of the methods of gene therapy, see Goldspiel et al., 1993, Clinical Pharmacy 12:488-505; Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May, 1993, TIBTECH 11(5): 155-215. Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

In a preferred embodiment of the invention, the therapeutic composition comprises a coding sequence that is part of an expression vector. In particular, such a nucleic acid has a promoter operably linked to the coding sequence, said promoter being inducible or constitutive, and, optionally, tissue-specific. In another specific embodiment, a nucleic acid molecule is used in which the coding sequence and any other desired sequences are flanked by regions that promote homologous recombination at a desired site in the genome, thus providing for intrachromosomal expression of the nucleic acid (Koller and Smithies, 1989, Proc. Natl. Acad. Sci. USA 86:8932-8935; Zijlstra et al., 1989, Nature 342: 435-438).

Delivery of the nucleic acid into a patient may be either direct, in which case the patient is directly exposed to the nucleic acid or nucleic acid-carrying vector, or indirect, in which case, cells are first transformed with the nucleic acid in vitro, then transplanted into the patient. These two approaches are known, respectively, as in vivo or ex vivo gene therapy.

In a specific embodiment, the nucleic acid is directly administered in vivo, where it is expressed to produce the encoded product. This can be accomplished by any methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286), by direct injection of naked DNA, by use of microparticle bombardment (e.g., a gene gun; Biolistic, DuPont), by coating with lipids or cell-surface receptors or transfecting agents, by encapsulation in liposomes, microparticles, or microcapsules, by administering it in linkage to a peptide which is known to enter the nucleus, or by administering it in linkage to a ligand subject to receptor-mediated endocytosis (see e.g., Wu and Wu, 1987, J. Biol. Chem. 262: 4429-4432) which can be used to target cell types specifically expressing the receptors. In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992; WO 92/22635 dated Dec. 23, 1992; WO92/20316 dated Nov. 26, 1992; WO93/14188 dated Jul. 22, 1993; WO 93/20221 dated Oct. 14, 1993). Alternatively, the nucleic acid can be introduced intracellularly and incorporated within host cell DNA for expression, by homologous recombination (Koller and Smithies, 1989, Proc. Natl. Acad. Sci. USA 86:8932-8935; Zijlstra et al., 1989, Nature 342:435-438).

In a preferred embodiment of the invention, adenoviruses as viral vectors can be used in gene therapy. Adenoviruses have the advantage of being capable of infecting non-dividing cells (Kozarsky and Wilson, 1993, Current Opinion in Genetics and Development 3:499-503). Other instances of the use of adenoviruses in gene therapy can be found in Rosenfeld et al., 1991, Science 252:431-434; Rosenfeld et al., 1992, Cell 68:143-155; and Mastrangeli et al., 1993, J. Clin. Invest. 91:225-234. Furthermore, adenoviral vectors with modified tropism may be used for cell specific targeting (WO98/40508). Adeno-associated virus (AAV) has also been proposed for use in gene therapy (Walsh et al., 1993, Proc. Soc. Exp. Biol. Med. 204:289-300).

In addition, retroviral vectors (see Miller et al., 1993, Meth. Enzymol. 217:581-599) have been modified to delete retroviral sequences that are not necessary for packaging of the viral genome and integration into host cell DNA. The coding sequence to be used in gene therapy is cloned into the vector, which facilitates delivery of the gene into a patient. More detail about retroviral vectors can be found in Boesen et al., 1994, Biotherapy 6:291-302, which describes the use of a retroviral vector to deliver the mdr1 gene to hematopoietic stem cells in order to make the stem cells more resistant to chemotherapy. Other references illustrating the use of retroviral vectors in gene therapy are: Clowes et al., 1994, J. Clin. Invest. 93:644-651; Kiem et al., 1994, Blood 83:1467-1473; Salmons and Gunzberg, 1993, Human Gene Therapy 4:129-141; and Grossman and Wilson, 1993, Curr. Opin. in Genetics and Devel. 3:110-114.

Another approach to gene therapy involves transferring a gene to cells in tissue culture. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, lipofection, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see e.g., Loeffler and Behr, 1993, Meth. Enzymol. 217:599-618; Cohen et al., 1993, Meth. Enzymol. 217:618-644; Cline, 1985, Pharmac. Ther. 29:69-92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny. In a preferred embodiment, the cell used for gene therapy is autologous to the patient.

In a specific embodiment, the nucleic acid to be introduced for purposes of gene therapy comprises an inducible promoter operably linked to the coding sequence, such that expression of the nucleic acid is controllable by controlling the presence or absence of the appropriate inducer of transcription.

Oligonucleotides such as anti-sense RNA and DNA molecules, and ribozymes that function to inhibit the translation of a targeted mRNA, especially its C-terminus, are also within the scope of the invention. Anti-sense RNA and DNA molecules act to directly block the translation of mRNA by binding to targeted mRNA and preventing protein translation. In regard to antisense DNA, oligodeoxyribonucleotides derived from the translation initiation site, e.g., between −10 and +10 regions of a nucleotide sequence, are preferred. The antisense oligonucleotide may comprise at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine.

Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Within the scope of the invention are engineered hammerhead motif ribozyme molecules that specifically and efficiently catalyze endonucleolytic cleavage of target RNA sequences.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features such as secondary structure that may render the oligonucleotide sequence unsuitable. The suitability of candidate targets may also be evaluated by testing their accessibility to hybridization with complementary oligonucleotides, using ribonuclease protection assays.

The anti-sense RNA and DNA molecules and ribozymes of the invention may be prepared by any method known in the art for the synthesis of nucleic acid molecules. These include techniques for chemically synthesizing oligodeoxyribonucleotides well known in the art such as for example solid phase phosphoramidite chemical synthesis. Alternatively, RNA molecules may be generated by in vitro and in vivo transcription of DNA sequences encoding the RNA molecule. Such DNA sequences may be incorporated into a wide variety of vectors which contain suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various modifications to the DNA molecules may be introduced as a means of increasing intracellular stability and half-life. Possible modifications include, but are not limited to, the addition of flanking sequences of ribo- or deoxynucleotides to the 5' and/or 3' ends of the molecule or the use of phosphorothioate or 2' 0-methyl rather than phosphodiesterase linkages within the oligodeoxyribonucleotide backbone.

C. Other Pharmaceutical Compositions

The compounds of the invention, may be administered to a subject per se or in the form of a sterile composition or a pharmaceutical composition. Pharmaceutical compositions comprising the compounds of the invention may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries that facilitate processing of the active peptides or peptide analogues into preparations which can be used pharmaceutically. Proper formulation is dependent upon the route of administration chosen.

For topical administration the compounds of the invention can be formulated as solutions, gels, ointments, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal, oral or pulmonary administration.

For injection, the compounds of the invention can be formulated in aqueous solutions, preferably in physiologically compatible buffers such as Hanks's solution, Ringer's solution, or physiological saline buffer. The solution can contain formulatory agents such as suspending, stabilizing and/or dispersing agents.

Alternatively, the compounds can be in powder form for constitution with a suitable vehicle, e.g., sterile pyrogen-free water, before use.

For transmucosal administration, penetrants appropriate to the barrier to be permeated are used in the formulation. Such penetrants are generally known in the art. This route of administration may be used to deliver the compounds to the nasal cavity.

For oral administration, the compounds can be readily formulated by combining the active peptides or peptide analogues with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate.

If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. Additionally, flavoring agents, preservatives, coloring agents and the like may be added.

For buccal administration, the compounds may take the form of tablets, lozenges, etc. formulated in conventional manner.

For administration by inhalation, the compounds for use according to the present invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems may be employed. Liposomes and emulsions are well known examples of delivery vehicles that may be used to deliver peptides and peptide analogues of the invention. Certain organic solvents such as dimethylsulfoxide also may be employed, although usually at the cost of greater toxicity. Additionally, the compounds may be delivered using a sustained-release system, such as semipermeable matrices of solid polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

As the compounds of the invention may contain charged side chains or termini, they may be included in any of the above-described formulations as the free acids or bases or as pharmaceutically acceptable salts. Pharmaceutically acceptable salts are those salts which substantially retain the biologic activity of the free bases and which are prepared by reaction with inorganic acids. Pharmaceutical salts tend to be more soluble in aqueous and other protic solvents than are the corresponding free base forms.

D. Effective Dosages

The compounds of the invention will generally be used in an amount effective to achieve the intended purpose (e.g., treatment of a neuronal injury). The compounds of the invention or pharmaceutical compositions thereof, are administered or applied in a therapeutically effective amount. By therapeutically effective amount is meant an amount effective ameliorate or prevent the symptoms, or prolong the survival of, the patient being treated. Determination of a therapeutically effective amount is well within the capabilities of those skilled in the art, especially in light of the detailed disclosure provided herein. An "inhibitory amount" or "inhibitory concentration" of a PL-PDZ binding inhibitor is an amount that reduces binding by at least about 40%, preferably at least about 50%, often at least about 70%, and even as much as at least about 90%. Binding can be measured in vitro (e.g., in an A assay or G assay) or in situ.

For systemic administration, a therapeutically effective dose can be estimated initially from in vitro assays. For example, a dose can be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the compounds that are sufficient to maintain therapeutic effect. Usual patient dosages for administration by injection range from about 0.1 to 5 mg/kg/day, preferably from about 0.5 to 1 mg/kg/day. Therapeutically effective serum levels may be achieved by administering multiple doses each day. For usual peptide therapeutic treatment of stroke, acute administration of 0.03 nmol/g to 30 nmol/g within 6 hours of stroke or brain ischemia is typical. In other instances, 0.1 nmol/g to 20 nmol/g within 6 hours are administered. And in still other instances 1 nmol/g to 10 nmol/g is administered with in 6 hours.

In cases of local administration or selective uptake, the effective local concentration of the compounds may not be related to plasma concentration. One having skill in the art will be able to optimize therapeutically effective local dosages without undue experimentation.

The amount of compound administered will, of course, be dependent on the subject being treated, on the subject's weight, the severity of the affliction, the manner of administration and the judgment of the prescribing physician.

The therapy may be repeated intermittently while symptoms detectable or even when they are not detectable. The therapy may be provided alone or in combination with other drugs.

E. Toxicity

Preferably, a therapeutically effective dose of the compounds described herein will provide therapeutic benefit without causing substantial toxicity.

Toxicity of the compounds described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds which exhibit high therapeutic indices are preferred. The data obtained from these cell culture assays and animal studies can be used in formulating a dosage range that is not toxic for use in human. The dosage of the compounds described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, In: *The Pharmacological Basis of Therapeutics*, Ch.1, p. 1).

EXAMPLES

Example 1

Identification of CLCA Interactions with PDZ Domains

GST-PDZ fusions were produced that each contain an entire PDZ domain (or multiple PDZ domains), the collection encompassing approximately 90% of all PDZ domains identified in the human genome. (See Table 5 and Section V (PDZ Proteins and PL Protein Interactions Disclosure). Biotinylated peptide corresponding to 11 residues of Tat coupled to either the C-terminal 9 amino acids of hCLCA1 (Tat-hCLCA1; YGRKKRRQRRRIGELQLSIA (SEQ ID NO:9)) or the C terminal 9 amino acids of mCLCA3 (Tat-CLCA3; YGRKKRRQRRREMQVTLGLH (SEQ ID NO:10)) was synthesized and purified by HPLC.

A modified G assay was used to identify interactions between hCLCA1 and mCLCA3 and PDZ domains. Peptides were synthesized as described supra, corresponding to the C-terminal amino acid sequences of hCLCA and mCLCA3. These peptides were assayed for the ability to bind PDZ domains using PDZ proteins synthesized from the expression constructs described in greater detail in section IV.

The peptides were assayed using a modified G assay as follows:

A Nunc Maxisorp 96 well Immunoplate (Nunc cat#62409-002) was coated with 100 µl of 5 µg/ml goat anti-GST polyclonal antibody (Amersham Pharmacia cat#27-457-01) and incubated overnight at 4° C. The plate was blocked by addition of 200 µl Assay Buffer (2% bovine serum albumin in PBS, pH 7.4) for 1 to 2 hours at room temperature, then washed three times in Assay Buffer.

50 µl per well of GST-PDZ fusion proteins (5 µg/ml in Assay Buffer), or, as a negative control, GST polypeptide alone, was added to the plate, and incubated for 1 to 2 hours at 4° C.

Biotinylated peptides were prepared in Assay Buffer, in half the volume required at 40 µM. HRP-Streptavidin (Zymed cat#43-4323) was diluted 1:1000 in another half volume of Assay Buffer, then mixed with the peptides. The peptide-HRP mixtures were incubated for 20 minutes at room temperature. The plate was washed three times with cold PBS, the peptide-HRP mixtures added at 50 µl per well, and the plate was incubated at room temperature for precisely 30 minutes after the addition of the last peptide.

The plate was then washed five times with room temperature PBS, and developed by addition of 100 µl/well of HRP substrate solution (3,3',5,5', tetramethylbensidine (TMB) (Dako cat#S1600)) for a maximum of 30 minutes in the dark at room temperature. The reaction of HRP and its substrate was terminated by addition of 100 µl of 0.18 M $H_2SO_4$ (Sigma cat#S1526), and the absorbance of each well of the plate was read at 450 nm.

Results of those assays that showed a high binding affinity are shown in TABLE 4. Listed are interactions which reproducibly gave an optical density reading of at least 0.5, at a signal to noise ratio of at least 1.5.

TABLE 3

PDZ Protein Domains that bind to CLCA1

| Peptide | PDZ binding partners | Peptide | PDZ binding partners |
|---------|---------------------|---------|---------------------|
| Tat-hCLCA1 (SIA) | INADL (PDZ #8) GORASP1 (PDZ #1) KIAA0313 NeDLG (PDZ #3) MUPP1 (PDZ #10) KIAA1415 KIAA1284 | Tat-CLCA3 (GLH) | GORASP1 (PDZ #1) KIAA0313 KIAA1284 |

Example 2

Titration Experiments

Using the modified G assay described in Example 1, several GST-PDZ domain proteins were tested to determine their relative binding strength to the C-terminal sequences of hCLCA1 and mCLCA3. The Tat-hCLCA1 and Tat-CLCA3 peptides described in Example 1 were titrated against a constant amount of GST-PDZ domain fusion protein and the results are shown below.

Data was fitted to the equation:

$y=100.0/(1+10^{((log(m1)-log(m0))*m2)})$, where $m1=EC_{50}$, $m2$=Hill coefficient, and $m0$=peptide concentration to calculate the $EC_{50}$ for the binding of the peptides to the PDZ domains.

TABLE 4

| Tat-hCLCA1 | | Tat-CLCA3 | |
|---|---|---|---|
| PDZ domain | EC50 (µM) | PDZ domain | EC50 (µM) |
| GORASP1 d1 | 0.12 | GORASP1 d1 | 0.66 |
| KIAA1284 | 0.074 | KIAA1284 | 0.54 |
| TIP2 | 1.1 | FLJ31349 | 0.60 |
| PSD95 d2 | 3.1 | ZO-3 d1 | 4.1 |

Example 3

Peptide Binding

The G assay or one of the modified variants described supra was used to determine the binding of a range of peptides to the three PDZ domains, GORASP1, KIAA0313, and KIAA1284, shown to interact with CLCA. Peptides demonstrating interactions with any of these three PDZ domains are shown in Table 5. The peptides listed are those which showed an average OD at 450 nm of at least 0.5, at a signal to noise ratio of at least 2.0.

TABLE 5

| PDZ | Peptide Name | Peptide Sequence | |
|---|---|---|---|
| GORASP1 | Tat-CLCA-3 (murine) | YGRKKRRQRRREMQVTLGLH (SEQ ID NO: 11) | 1.735 |
| KIAA0313 | Tat-N-protein-SARS | YGRKKRRQRRRGASADSTQA (SEQ ID NO: 12) | 1.16 |
| KIAA0313 | PAR-2 | KHSRKSSSYSSSSTTVKTSY (SEQ ID NO: 13) | 0.78 |
| KIAA1284 | Tat-M-Protein-SARS | YGRKKRRQRRRNDNIALLVQ (SEQ ID NO: 14) | 2.35 |
| KIAA1284 | Tat-CLCA-3 (murine) | YGRKKRRQRRREMQVTLGLH (SEQ ID NO: 15) | 2.29 |
| KIAA1284 | Tat-E-protein-SARS | YGRKKRRQRRRSEGVPDLLV (SEQ ID NO: 16) | 1.97 |
| KIAA1284 | alpha-2C Adrenergic receptor | DFRPSFKHILFRRARRGFRQ (SEQ ID NO: 17) | 1.55 |
| KIAA1284 | Fas Ligand | SSKSKSSEESQTFFGLYKL (SEQ ID NO: 18) | 1.22 |
| KIAA1284 | HPV E6 #35 (cysteine-free) | GRWTGRAMSAWKPTRRETEV (SEQ ID NO: 19) | 1.12 |
| KIAA1284 | ephrin B2 | ILNSIQVMRAQMNQIQSVEV (SEQ ID NO: 20) | 0.97 |
| KIAA1284 | PAR-2 | KHSRKSSSYSSSSTTVKTSY (SEQ ID NO: 21) | 0.95 |
| KIAA1284 | TATNMDA2B9 | YGRKKRRQRRRKLSSIESDV (SEQ ID NO: 22) | 0.86 |
| KIAA1284 | alpha-2A Adrenergic receptor | HDFRRAFKKILARGDRKRIV (SEQ ID NO: 23) | 0.85 |
| KIAA1284 | KIAA1481 | PIPAGGCTFSGIFPTLTSPL (SEQ ID NO: 24) | 0.79 |
| KIAA1284 | noradrenaline transporter | HHLVAQRDIRQFQLQHWLAI (SEQ ID NO: 25) | 0.66 |
| KIAA1284 | Fibroblast growth factor receptor 3 IIIc isoform 1 | FHSKTAGANTTDKELEVLSL (SEQ ID NO: 26) | 0.66 |
| KIAA1284 | NMDA | LNSCSNRRVYKKMPSIESDV (SEQ ID NO: 27) | 0.63 |
| KIAA1284 | KV1.3 | TTNNNPNSAVNIKKIFTDV (SEQ ID NO: 28) | 0.61 |
| KIAA1284 | CD4 (modified) | LSEKKTSQSPHRFQKTASPI (SEQ ID NO: 29) | 0.56 |
| KIAA1284 | Tat-N-protein-SARS | YGRKKRRQRRRGASADSTQA (SEQ ID NO: 30) | 0.52 |

As these peptides demonstrate binding interactions to the PDZ domains of interest, they are candidates for inhibition of the interaction between these PDZ domains and CLCA1. Additional potential inhibitors include those listed below in TABLE 6.

TABLE 6

| | |
|---|---|
| YGRKKRRQRRRIGELQLSIA | (SEQ ID NO: 31) |
| YGRKKRRQRRRIGELQLSIV | (SEQ ID NO: 32) |
| YGRKKRRQRRRIGELQLSWA | (SEQ ID NO: 33) |
| YGRKKRRQRRREMQVTLGWH | (SEQ ID NO: 34) |
| YGRKKRRQRRREMQVTLSWH | (SEQ ID NO: 35) |
| YGRKKRRQRRRIGELQLSLA | (SEQ ID NO: 36) |
| YGRKKRRQRRRIGELQLTIA | (SEQ ID NO: 37) |
| YGRKKRRQRRREMQVTLTLH | (SEQ ID NO: 38) |
| YGRKKRRQRRRIGELQLSIL | (SEQ ID NO: 39) |
| YGRKKRRQRRREMQVTLSIA | (SEQ ID NO: 40) |

Example 4

CACL Activity Assays

The activity of CACL in the presence or absence of candidate agonists or antagonists may be tested in the following assays.

CACL can be expressed by transforming a mammalian cell line, such as the pneumocyte cell line A549, the embryonic kidney cell line HEK293, or the mouse 3T3 fibroblast cell line, with a eukaryotic expression vector encoding CLCA. Eukaryotic expression vectors are commercially available, and techniques to introduce them into cells are well known in the art. The activity of CACL may be tested by whole cell voltage-clamp studies, as described, for example, in Loewen, M. E. et al. (2002; Am. J. Physiol. Cell. Physiol. 283: C412-C421).

An alternative assay makes use of the fact that CLCA1 has been shown to induce mucin (MUC) gene expression. Mammalian cells, such as A549, HEK293, or 3T3 cells, are co-transfected with both a eukaryotic expression vector encoding CLCA, and a vector comprising the MUC5AC promoter region fused upstream of a reporter gene, such as luciferase. The levels of MUC gene expression induced, as determined by detection of the reporter using methods known in the art, is indicative of CLCA1 activity.

Example 5

Mouse Model of Airway Hyperresponsiveness

A mouse model of airway hyperresesponsiveness is established using mice immunized with ovalbumin and challenged with aerosolized antigen, as described in the literature (Corry, D. B. et al. (1996) J. Exp. Med. 183:109-117; Nakanishi, A. et al. (2001) Proc. Natl. Acad. Sci. USA 98:5175-5180). Briefly, BALB/c mice are immunized by subcutaneous injection of 20-25 ug ovalbumin (OVA; Sigma) administer with 2 mg aluminum hydroxide (Alum). The mice are further sensitized by an interperitoneal injection of 10 ug OVA with 1 mg of Alum. The immunized mice are subsequently exposed to an aerosol of 5% (wt/vol) OVA in 0.5×PBS for 25 minutes each day for 7 consecutive days. Aerosolization of antigens may be performed using a nose-only aerosol chamber adapted for mice (Intox Products, Albuquerque N. Mex.) coupled to a nebulizer (Aerotech H; CIS-US, Bedford Mass.).

Determination of airway physiology is performed as described (Corry, D. B. et al. (1996) J. Exp. Med. 183:109-117; Nakanishi, A. et al. (2001) Proc. Natl. Acad. Sci. USA 98:5175-5180).

This mouse model may be used to test the therapeutic effects of candidate agonists or antagonists of CLCA-PDZ binding interactions.

The present invention is not to be limited in scope by the exemplified embodiments which are intended as illustrations of single aspects of the invention and any sequences which are functionally equivalent are within the scope of the invention.

Indeed, various modifications of the invention in addition to those shown and described herein will become apparent to those skilled in the art from the foregoing description and accompanying drawings. Such modifications are intended to fall within the scope of the appended claims.

All publications, patents and patent applications cited herein are hereby incorporated by reference in their entirety for all purposes to the same extent as if each individual publication, patent or patent application were specifically and individually indicated to be so incorporated by reference.

What is claimed is:

1. An inhibitor comprising an isolated, recombinant or synthetic polypeptide that inhibits binding between a calcium-activated chloride channel (CLCA) protein and a PDZ protein, wherein the polypeptide is from 3 to about 20 amino acids in length and wherein the C-terminal amino acid sequence of polypeptide is selected from the group consisting of SIA, SW, SIL, SWA, SLA, GWH, SWH, TIA, and TLH.

2. The inhibitor of claim 1, wherein the PDZ protein comprising at least one PDZ domain is selected from the group consisting of KIAA0313, GRASP1, KIAA1284 and PICK1.

3. The inhibitor of claim 1, wherein the CLCA protein is human CLCA1 or mouse CLCA3.

4. The inhibitor of claim 1, wherein the C-terminus of the polypeptide comprises a PDZ-Ligand sequence of 3-8 amino acids or about 9-20 amino acids.

5. The inhibitor of claim 4, wherein the PDZ-Ligand sequence comprises the amino acid sequence SIA.

6. The inhibitor of claim 4, wherein the C-terminus of the polypeptide further comprises a cell membrane transduction domain.

7. The inhibitor of claim 6, wherein the cell membrane transduction domain is selected from the group consisting of AMP, HIV tat, *Drosophila* antennapedia, herpes simplex virus VP22, anti-DNA CDR2, anti-DNA CDR3, polyarginine and penetratin.

8. A pharmaceutical composition comprising the inhibitor of claim 1 and a physiologically acceptable carrier, diluent or excipient.

9. The inhibitor of claim 1, wherein the C-terminal amino acid sequence of polypeptide is SIA or GWH.

* * * * *